United States Patent [19]

Shibasaki et al.

[11] Patent Number: 4,837,342
[45] Date of Patent: Jun. 6, 1989

[54] PROSTACYCLIN ANALOGUE, AND BLOOD CIRCULATION IMPROVING AGENT AND ANTI-ULCER COMPOSITION CONTAINING IT AS ACTIVE INGREDIENT

[75] Inventors: Masakatsu Shibasaki, Sapporo; Atsuo Takahashi; Tuyoshi Aoki, both of Sagamihara; Kentaro Kogi, Fukushima; Yozo Nishimiya, Fukushima; Takeshi Nara, Fukushima; Takashi Yamaguchi, Fukushima, all of Japan

[73] Assignees: Sagami Chemical Research Center; Toa Eiyo Ltd., both of Tokyo, Japan

[21] Appl. No.: 14,591

[22] Filed: Feb. 13, 1987

[30] Foreign Application Priority Data

Feb. 28, 1986 [JP] Japan .................................. 61-41691
Feb. 28, 1986 [JP] Japan .................................. 61-41693
Dec. 4, 1986 [JP] Japan .................................. 61-287740
Dec. 4, 1986 [JP] Japan .................................. 61-287732
Dec. 4, 1986 [JP] Japan .................................. 61-287734
Dec. 4, 1986 [JP] Japan .................................. 61-287736
Dec. 4, 1986 [JP] Japan .................................. 61-287737
Dec. 4, 1986 [JP] Japan .................................. 61-287738
Dec. 4, 1986 [JP] Japan .................................. 61-287739

[51] Int. Cl.[4] ............................................. C07C 177/00
[52] U.S. Cl. ................................. 549/422; 556/441; 560/55; 560/121; 562/471; 562/472; 562/503; 514/530; 564/172; 564/188; 564/189
[58] Field of Search ....................... 549/422; 556/441; 560/55, 121; 562/471, 472, 503; 514/530; 564/172, 188, 189

[56] References Cited

FOREIGN PATENT DOCUMENTS 873731 7/1979 Belgium .

Primary Examiner—Paul J. Killos
Attorney, Agent, or Firm—Oblon, Fisher, Spivak, McClelland & Maier

[57] ABSTRACT

A prostacyclin analogue having the formula:

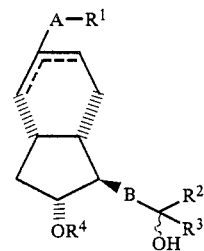

wherein $R^1$ is $-CO_2R^5$ (wherein $R^5$ is a hydrogen atom, a straight chain or branched alkyl group having from 1 to 12 carbon atoms, an aralkyl group having from 7 to 12 carbon atoms, a cycloalkyl group having from 4 to 7 carbon atoms and unsubstituted or substituted by at least one alkyl group having from 1 to 4 carbon atoms, a substituted or unsubstituted phenyl group, or one equivalent of a cation), or $-CONR^6R^7$ (wherein each of $R^6$ and $R^7$ is a hydrogen atom or an alkyl group having from 1 to 10 carbon atoms, or $R^6$ and $R^7$ together with the adjacent nitrogen atom, form a 5- or 6-membered substituted or unsubstituted hetero ring which may contain a hetero atom other than said nitrogen atom); A is $-CH_2CH_2CH_2-$, $CH_2-O-CH_2CH_2-$, $-CH_2CH_2CH_2CH_2-$, $-CH_2CH_2-O-CH_2-$ or $-CH=CHCH_2CH_2-$; B is trans $-CH=CH-$ or $-C\equiv C-$; $R^2$ is a straight chain or branched alkyl group having from 3 to 10 carbon atoms, a cycloalkyl group having from 4 to 7 carbon atoms and unsubstituted or substituted by at least one alkyl group having from 1 to 4 carbon atoms, a straight chain or branched alkenyl group having from 3 to 12 carbon atoms, a straight chain or branched alkynyl group having from 3 to 8 carbon atoms, or an alkyl group having from 1 to 3 carbon atoms substituted by a substituted or unsubstituted phenyl or phenoxy group, by an alkoxy group having from 1 to 6 carbon atoms or by a cycloalkyl group having from 5 to 8 carbon atoms; $R^3$ is a hydrogen atom, a methyl group or a vinyl group; and $R^4$ is a hydrogen atom, an acyl group having from 1 to 7 carbon atoms, a tri-$C_1$-$C_7$ hydrocarbon-silyl group or a group capable of forming an acetal bond together with the oxygen atom of a hydroxyl group; provided that the double bond in a substituent for A is E or Z, or a mixture thereof; the asymmetric center in a substituent for $R^2$ assumes a R-conformation or a S-conformation, or a mixture thereof; and the bonds shown by dotted lines at the 2-3 and 3-4 positions mean that either one of them is a double bond.

4 Claims, No Drawings

PROSTACYCLIN ANALOGUE, AND BLOOD CIRCULATION IMPROVING AGENT AND ANTI-ULCER COMPOSITION CONTAINING IT AS ACTIVE INGREDIENT

The present invention relates to a novel stable prostacyclin analogue, a blood circulation improving agent containing it as an active ingredient and having high selectivity in the blood platelet agglutination inhibiting activity, which is useful for the prevention or treatment of various circulatory disorders, and an anti-ulcer composition which is useful for the prevention or treatment of ulcer in the digestive tract.

Prostacyclin (hereinafter referred to simply as PGI$_2$) is known as a physiologically active natural substance and has a structure of the formula:

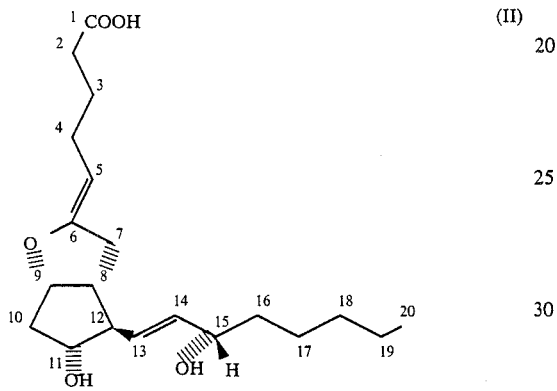

Its chemical name is (5Z,13E)-(9α,11α,15S)-6,9-epoxy-11,15-dihydroxyprosta-5,13-diene acid. PGI$_2$ is present in the arterial wall and has strong blood platelet agglutination inhibiting activities and peripheral arterial smooth muscle atonic activities [Nature, 263, 663(1976)]. Such PGI$_2$ is useful for the prevention and treatment of cerebral thrombosis, myocardial infarction or acute angina pectoris which is induced by a progress of blood platelet agglutination or by an increase of the thrombotic tendency, and it is expected for application to the prevention or the treatment of arterisclerosis and it is expected to be developped as a so-called blood flow improving drug. Further, prostaglandins containig PGI$_2$ are known to have gastric mucosal protecting activities and gastric mucosal blood flow increasing activities ['83 Inflammation Seminar "Prostaglandin", preparatory text, page 50 (organized by Japan Inflammation Academy)]. Such PGI$_2$ is expected to be applicable for the prevention and treatment of a digestive tract ulcer, such as gastric ulcer.

However, PGI$_2$ is a very unstable substance. This is a major problem in its development as a drug.

In order to solve such a problem, some researches have been made on stable analogues having a structure such that the oxygen atom between the carbon atoms at the 6- and 9-positions of PGI$_2$ is substituted by a carbon atom. A carbacyclin compound of the formula III represented by OP-41483 (Japanese Unexamined Patent Publication No. 130543/1979) and 9-(O)-methano-Δ$^6$-PGI$_1$ of the formula IV (Japanese Unexamined Patent Publication No. 32436/1981) are PGI$_2$ analogues which are both chemically stable. Further, 9(O)-methano-Δ$^{6(9α)}$-PGI$_1$(isocarbacyclin) of the formula V having a structure such that the double bond at the 5-position of 9(O)-methanoprostacyclin (carbacyclin) has been transferred to 6(9α)-position, is also adequately chemically stable, and is reported as a PGI$_2$ anologue having strong physiological activities (Japanese Unexamined Patent Publication No. 137445/1984).

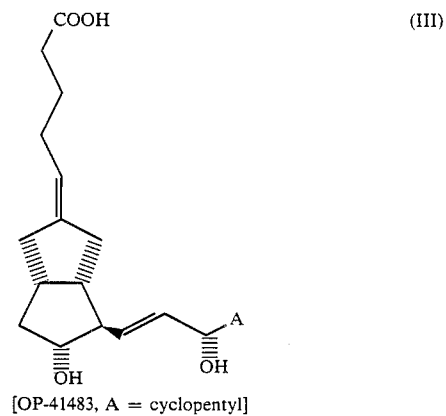

[OP-41483, A = cyclopentyl]

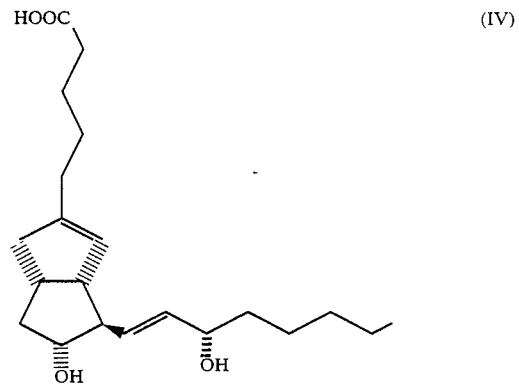

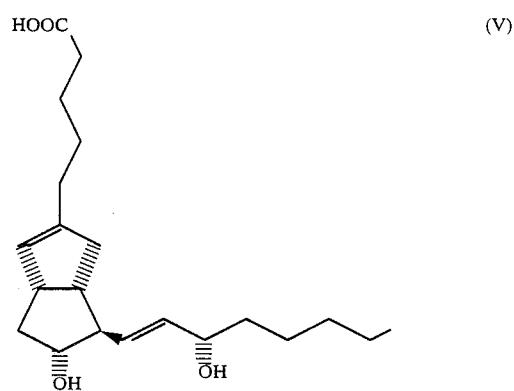

The present inventors have conducted a wide range of researches with an aim to develop prostacyclins which are stable without any substantial decomposition at room temperature and having excellent pharmacological properties. As a result, novel prostacyclins have been prepared and it has been found that they have strong blood circulation improving activities and anti-ulcer activities, and no substantial toxicity. The present invention has been accomplished on the basis of these discoveries.

The present invention provides a prostacyclin analogue having the formula:

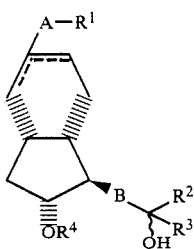

(I)

wherein $R^1$ is —$CO_2R^5$ (wherein $R^5$ is a hydrogen atom, a straight chain or branched alkyl group having from 1 to 12 carbon atoms, an aralkyl group having from 7 to 12 carbon atoms, a cycloalkyl group having from 4 to 7 carbon atoms and unsubstituted or substituted by at least one alkyl group having from 1 to 4 carbon atoms, a substituted or unsubstituted phenyl group, or one equivalent of a cation), or —$CONR^6R^7$ (wherein each of $R^6$ and $R^7$ is a hydrogen atom or an alkyl group having from 1 to 10 carbon atoms, or $R^6$ and $R^7$ together with the adjacent nitrogen atom, form a 5- or 6-membered substituted or unsubstituted hetero ring which may contain a hetero atom other than said nitrogen atom); A is —$CH_2CH_2CH_2$—, $CH_2$—O—$CH_2$—, —$CH_2CH_2CH_2$—, —$CH_2CH_2$—O—$CH_2$— or —CH=CHCH$_2$CH$_2$—; B is trans —CH=CH— or —C≡C—; $R^2$ is a straight chain or branched alkyl group having from 3 to 10 carbon atoms, a cycloalkyl group having from 4 to 7 carbon atoms and unsubstituted or substituted by at least one alkyl group having from 1 to 4 carbon atoms, a straight chain or branched alkenyl group having from 3 to 12 carbon atoms, a straight chain or branched alkynyl group having from 3 to 8 carbon atoms, or an alkyl group having from 1 to 3 carbon atoms substituted by a substituted or unsubstituted phenyl or phenoxy group, by an alkoxy group having from 1 to 6 carbon atoms or by a cycloalkyl group having from 5 to 8 carbon atoms; $R^3$ is a hydrogen atom, a methyl group or a vinyl group; and $R^4$ is a hydrogen atom, an acyl group having from 1 to 7 carbon atoms, a tri-$C_1$-$C_7$ hydrocarbon-silyl group or a group capable of forming an acetal bond together with the oxygen atom of a hydroxyl group; provided that the double bond in a substituent for A is E or Z, or a mixture thereof; the asymmetric center in a substituent for $R^2$ assumes a R-conformation or a S-conformation, or a mixture thereof; and the bonds shown by dotted lines at the 2-3 and 3-4 positions mean that either one of them is a double bond.

The present invention also provides a blood circulation improving agent comprising an effective amount of the prostacyclin analogue of the formula I and a pharmaceutically acceptable carrier.

Further, the present invention provides an anti-ulcer composition comprising an effective amount of the prostacyclin analogue of the formula I and a pharmaceutically acceptable carrier.

Now, the present invention will be described in detail with reference to the preferred embodiments.

The straight chain or branched alkyl group having from 1 to 12 carbon atoms for $R^1$ includes, for example, methyl, ethyl, n-propyl, iso-propyl, n-butyl, sec-butyl, tert-butyl, n-pentyl, iso-amyl, n-hexyl, n-heptyl, n-octyl, n-nonyl, n-decyl, n-undecyl and n-dodecyl.

The aralkyl group having from 7 to 12 carbon atoms for $R^1$ includes, for example, benzyl, 1-phenethyl, 2-phenethyl, 3-phenylbutyl, 4-phenylbutyl, 1-(2-naphthyl)ethyl and 2-(1-naphthyl)ethyl.

The cycloalkyl group having from 4 to 7 carbon atoms, which is unsubstituted or substituted by at least one alkyl group having from 1 to 4 carbon atoms, for $R^1$ includes, for exxample, cyclobutyl, 1-propylcyclobutyl, 1-butylcyclobutyl, 2-methylcyclobutyl, 2-propylcyclobutyl, 3-ethylcyclobutyl, 3-propylcyclobutyl, 2,3,4-triethylcyclobutyl, cyclopentyl, 3-ethylcyclopentyl, 3-propylcyclopentyl, 3-butylcyclopentyl, 3-tert-butylcyclopentyl, 2,2-dimethylcyclopentyl, (1-methyl-3-propyl)cyclopentyl, (2-methyl-4-propyl)cyclopentyl, cyclohexyl, 3-ethylcyclohexyl, 3-iso-propylcyclohexyl, 4-methylcyclohexyl, 4-ethylcyclohexyl, 4-propylcyclohexyl, 4-tert-butylcyclohexyl, 2,2-dimethylcyclohexyl, 2,6-dimethylcyclohexyl, (2,6-dimethyl-4-propyl)cyclohexyl and cycloheptyl.

The substituent for the substituted or unsubstituted phenyl group for $R^1$ includes, for example, a halogen /atom, a hydroxyl group, an acyloxy group having from 2 to 7 carbon atoms, an alkyl group having from 1 to 4 carbon atoms which may be substituted by a halogen atom, an alkoxy group having from 1 to 4 carbon atoms, which may be substituted by a halogen atom, a nitrile group, a carboxyl group and alkoxycarbonyl group having from 2 to 7 carbon atoms. Here, the halogen atom includes fluorine, chlorine and bromine, and particularly preferred is fluorine or chlorine. The acetoxy group having from 2 to 7 carbon atoms includes, for example, acetoxy, propionyloxy, n-butyryloxy, iso-butyryloxy, n-valeryloxy, iso-valeryloxy, caproyloxy, enanthryloxy and benzoyloxy.

As the alkyl group having from 1 to 4 carbon atoms, which may be substituted by halogen, methyl, ethyl, n-propyl, iso-propyl, n-butyl, chloromethyl, dichloromethyl, trifluoromethyl may be mentioned as preferred examples. Likewise, as the alkoxy group having from 1 to 4 carbon atoms which may be substituted by halogen, methoxy, ethoxy, n-propoxy, iso-propoxy, n-butoxy, chloromethoxy, dichloromethoxy and trifluoromethoxy, may be mentioned as preferred examples. As the alkoxycarbonyl group having from 2 to 7 carbon atoms, methoxycarbonyl, ethoxycarbonyl, butoxycarbonyl and hexyloxycarbonyl, may be mentioned. The number of substituents may be from 1 to 3, preferably 1. The one equivalent of a cation for $R^1$ includes, for example, an alkali metal cation such as Na$^+$ or K$^+$, and a bivalent or trivalent metal cation such as $\frac{1}{2}Ca^{2+}$, $\frac{1}{2}Mg^{2+}$ or $\frac{1}{3}Al^{3+}$, or an ammonium cation such as an ammonium ion or a tetramethylammonium ion.

The alkyl group having from 1 to 10 carbon atoms for $R^6$ or $R^7$ includes, for example, methyl, ethyl, n-propyl, iso-propyl, n-butyl, sec-butyl, tert-butyl, n-pentyl, iso-amyl, n-hexyl, n-heptyl, n-octyl, n-nonyl and n-decyl.

As the substituent for the substituted or unsubstituted hetero ring for $R^6$ or $R^7$, an alkyl group having from 1 to 4 carbon atoms, which may be substituted by a halogen atom, such as methyl, ethyl, n-propyl, iso-propyl, n-butyl, chloromethyl, dichloromethyl or trifluoromethyl, may be mentioned. The above-mentioned substituted or unsubstituted hetero ring may have from 1 to 3 substituents, preferably one substituent, as mentioned above. Further, as the hetero atom, a nitrogen, sulfur or oxygen atom may be mentioned. The hetero ring includes, for example, 1-pyrrolidyl, thiazolyl, 1-piperidyl, morpholinyl, piperazyl and 5,6-dihydrophenanthridinyl.

However, $R^1$ is preferably —COOR$^5$ wherein $R^5$ is straight chain or branched alkyl group having from 1 to 12 carbon atoms. Particularly preferred is a carboxyl group, a methoxy carbonyl group or an ethoxy carbonyl group.

The straight chain or branched alkyl group having from 3 to 10 carbon atoms for $R^2$ includes n-propyl, n-butyl, n-pentyl, 1-methylpentyl, 2-methylpentyl, 1,2-dimethylpentyl, n-hexyl, 1-methylhexyl, 2-methylhexyl, 1,2-dimethylhexyl, n-heptyl, n-octyl, n-nonyl and n-decyl. Particularly preferred are n-pentyl, 1-methylpentyl, 2-methylpentyl, 1,2-dimethylpentyl, n-hexyl, 1-methylhexyl and 2-methylhexyl.

The cycloalkyl group having from 4 to 7 carbon atoms, which is unsubstituted or substituted by at least one alkyl group having from 1 to 4 carbon atoms, for $R^2$ includes, for example, cyclobutyl, 1-propylcyclobutyl, 1-butylcyclobutyl, 1-pentylcyclobutyl, 2-methylcyclobutyl, 2-propylcyclobutyl, 3-ethylcyclobutyl, 3-propylcyclobutyl, 2,3,4-triethylcyclobutyl, cyclopentyl, 2-pentylcyclopentyl, 2,2-dimethylcyclopentyl, 3-ethylcyclopentyl, 3-propylcyclopentyl, 3-butylcyclopentyl, 3-tert-butylcyclopentyl, (1-methyl-3-propyl)cyclopentyl, (2-methyl-3-propyl)cyclopentyl, (2-methyl-4-propyl)cyclopentyl, cyclohexyl, 3-ethylcyclohexyl, 3-iso-propylcyclohexyl, 4-methylcyclohexyl, 4-ethylcyclohexyl, 4-propylcyclohexyl, 4-tert-butylcyclohexyl, 2,6-dimethylcyclohexyl, 2,2-dimethylcyclohexyl, (2,6-dimethyl-4-propyl)cyclohexyl and cycloheptyl. Particularly preferred are cyclopentyl and cyclohexyl.

The straight chain or branched alkenyl group having from 3 to 12 carbon atoms for $R^2$ includes, for example, allyl, 3-butenyl, 2-butenyl, 3-methyl-2-butenyl, 4-pentenyl, 3-pentenyl, 4-methyl-3-pentenyl, 2-pentenyl, 5-hexenyl, 4-hexenyl, 2-methyl-4-hexenyl, 5-methyl-2-hexenyl, 2,5-dimethyl-3-hexenyl, 6-heptenyl, 5-heptenyl, 2-ethyl-5-heptenyl, 2,6-dimethyl-5-heptenyl, 7-octenyl, 8-nonenyl, 9-decenyl, 10-undecenyl and 11-dodecenyl. Preferred are 3-pentenyl and 2,6-dimethyl-5-heptenyl.

The straight chain or branched alkynyl group having from 3 to 8 carbon atoms for $R^2$ includes propargyl, 2-butynyl, 3-butynyl, 2-methyl-3-butynyl, 2-ethyl-3-butynyl, 4-pentynyl, 3-pentynyl, 1-ethyl-3-pentynyl, 1-methyl-3-pentynyl, 2-methyl-3-pentynyl, 1,2-dimethyl-3-pentynyl, 1,1-dimethyl-3-pentynyl, 2,2-dimethyl-3-pentynyl, 3-hexynyl, 1-methyl-3-hexynyl, 2-methyl-3-hexynyl, 1,2-dimethyl-3-hexynyl, 1,1-dimethyl-3-hexynyl, 2,2-dimethyl-3-hexynyl, 4-heptynyl and 5-octynyl. Preferred are 1-methyl-3-pentynyl, 1-methyl-3-hexynyl and 2-methyl-3-hexynyl.

The alkyl group for the substituted alkyl group having from 1 to 3 carbon atoms for $R^2$, may be a straight chain or branched alkyl group and includes, for example, methyl, ethyl, n-propyl and iso-propyl. These alkyl groups are substituted by a phenyl group; a phenoxy group; an alkoxy group having from 1 to 6 carbon atoms such as methoxy, ethoxy, n-propoxy, n-butoxy, iso-butoxy, tert-butoxy, n-pentoxy or n-hexoxy; or a cycloalkyl group having from 5 to 8 carbon atoms such as cyclopentyl or cyclohexyl. $R^2$ is particularly preferably n-pentyl, 2-methylpentyl, 1,1-dimethylpentyl, 1-methylhexyl, 2-methylhexyl, 2,6-dimethyl-2-heptenyl, 1-methyl-3-hexynyl, 1-methyl-3-hexynyl, 2-methyl-3-hexynyl, (2-ethoxy-1-methyl)ethyl, cyclopentyl, cyclohexyl, 2-cyclohexylmethyl, 1-cyclohexylethyl or phenethyl.

$R^3$ is a hydrogen atom, a methyl group or a vinyl group.

$R^4$ is a hydrogen atom, an acyl group having from 1 to 7 carbon atoms, a tri-$C_1$-$C_7$ hydrocarbon-silyl group or a group capable of forming an acetal bond together with the oxygen atom of a hydroxyl group. Here, the acyl group having from 1 to 7 carbon atoms includes, for example, acetyl, propionyl, n-butyryl, iso-butyryl, n-valeryl, iso-valeryl, caproyl, enanthyl, benzoyl. Preferred are acetyl and benzoyl. The tri-$C_1$-$C_7$ hydrocarbon-silyl group includes a tri-$C_1$-$C_4$ alkyl silyl group such as trimethylsilyl, triethylsilyl or tert-butyldimethylsilyl, a diphenylalkylsilyl group such as tert-butyldiphenylsilyl, a tribenzylsilyl group, and a dimethyl(2,4,6-tri-tert-butylphenoxy)silyl group, as preferred examples. The group capable of forming an acetal bond together with the oxygen atom of a hydroxyl group may be, for example, methoxymethyl, 1-ethoxyethyl, 2-methoxypropyl, 2-ethoxy-2-propyl, (2-methoxyethoxy)methyl, benzyloxymethyl, 2-tetrahydropyranyl, 2-tetrahydrofuranyl, 4-(4-methoxytetrahydropyranyl) or 6,6-dimethyl-3-oxa-2-oxobicyclo[3,1,0]hex-4-yl. Among them, 2-tetrahydropyranyl, 2-tetrahydrofuranyl, 1-ethoxyethyl, 2-methoxy-2-propyl, (2-methoxyethoxy)methyl, 4-(4-methoxytetrahydropyranyl) and 6,6-dimethyl-3-oxa-2-oxobicyclo[3,1,0]hex-4-yl are preferred.

Particularly preferred as $R^4$ among them, are a hydrogen atom, tert-butyldimethylsilyl, tert-butyldiphenylsilyl, 2-tetrahydropyranyl, acetyl, 4-(4-methoxytetrahydropyranyl), 6,6-dimethyl-3-oxa-2-oxobicyclo[3,1,0]hex-4-yl, and dimethyl(2,4,6-tri-tert-butylphenoxy)silyl.

Specific examples of the prostacyclins according to the present invention will be given below.

(1)   3-(3-carboxypropyl)-7-exo-(3-hydroxy-trans-1-octenyl)-8-endo-hydroxy-cis-bicyclo[4,3,0]nona-2-ene (2)   3-(3-carboxypropyl)-7-exo-(3-hydroxy-4-methyl-trans-1-nonen-6-ynyl)-8-endo-hydroxy-cis-bicyclo[4,3,0]nona-2-ene (3)   3-(4-carboxybutyl)-7-exo-(3-hydroxy-trans-1-octenyl)-8-endo-hydroxy-cis-bicyclo[4,3,0]nona-2-ene (4)   3-(4-carboxybutyl)-7-exo-(3-hydroxy-4-methyl-trans-1-nonen-6-ynyl)-8-endo-hydroxy-cis-bicyclo[4,3,0]nona-2-ene (5)   3-(4-carboxy-1-butenyl)-7-exo-(3-hydroxy-trans-1-octenyl)-8-endo-hydroxy-cis-bicyclo[4,3,0]nona-2-ene (6)   3-(4-carboxy-1-butenyl)-7-exo-(3-hydroxy-4-methyl-trans-1-nonen-6-ynyl)-8-endo-hydroxy-cis-bicyclo[4,3,0]nona-2-ene (7)   [3-(3-oxa-4-carboxybutyl)-7-exo-(3α-hydroxy-4,8-dimethyl-1-trans-octen-6-ynyl)-8-endo-hydroxy-cis-bicyclo[4,3,0]nona-2-ene]

(8)   [3-(2-oxa-4-carboxybutyl)-7-exo-(3α-hydroxy-4,8-dimethyl-1-trans-octen-6-ynyl)-8-endo-hydroxy-cis-bicyclo[4,3,0]nona-2-ene]

(9)   [3-(4-carboxybutyl)-7-exo-(3α-hydroxy-4,8-dimethyl-1-trans-octen-6-ynyl)-8-endo-hydroxy-cis-bicyclo[4,3,0]nona-3-ene]

Now, the synthesis of prostacyclin analogues having a double bond between the 2- and 3-positions in the formula I, will be described.

In the present invention, $R^8$ in the following formulas is a protective group for a hydroxyl group. As such a protective group, a t-butyldimethylsilyl group, a triethylsilyl group, a tribenzylsilyl group and a diphenyl-t-butylsilyl group may be mentioned.

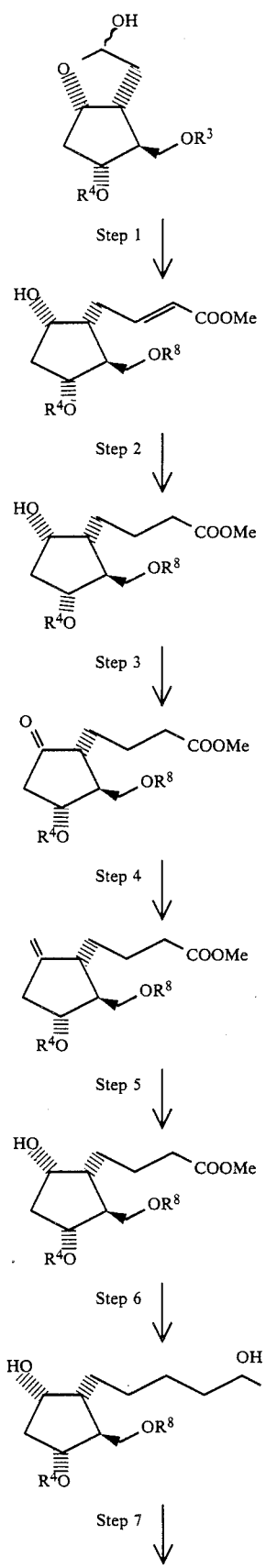

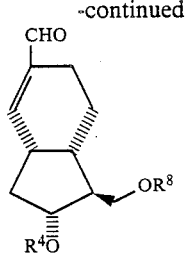

Step 1

In this step, a lactol of the formula VI is subjected to a Wittig reation to obtain an α, β-unsaturated ester derivative of the formula VII. The lactol of the formula VI can readily be obtained by the reduction of Corey lactone. (See Reference Examples given hereinafter).

The Wittig reaction in this step is conducted in an aromatic hydrocarbon such as toluene or benzene by using a stable ylide compound such as carbomethoxymethylenetriphenylphosphorane or carboethoxymethylenetriphenylphosphorane. The stable ylide compound is used usually in an amount of from 1 to 2 equivalent, and the reaction proceeds smoothly at a temperature of from 50° to 130° C.

Step 2

In this step, the α, β-unsaturated ester derivative of the formula VII obtained in the preceding Step 1 is reduced to obtain a hydroxy-ester of the formula VIII. This reduction reaction can be conducted under a hydrogen pressure of 1 atm in the presence of 5% Pd-C, 10% Pd-C or a Wilkinson complex. As the solvent, ethanol, methanol, benzene or ethylacetate can be used. In the presence of such a solvent, the reduction reaction readily proceeds at a temperature of from 0° to 50° C.

Step 3

In this step, the hydroxy-ester of the formula VIII obtained in the preceding Step 2 is oxidized to obtain a cyclopentanone derivative of the formula IX. This oxidation reaction readily proceeds in a halogenated hydrocarbon solvent such as methylene chloride by using a Collins' reagent or pyridinium chlorochromate. As a convenient reaction from the viewpoint of the experimental operation, the Swern oxidation reaction can also be employed. The Swern oxidation reaction can be conducted in methylene chloride by using from 2 to 3 equivalent of oxalyl chloride, from 4 to 5 equivalent of DMSO and from 10 to 15 equivalent of triethylamine. The reaction temperature may be selected within a range of from −78° C. to room temperature.

Step 4

In this step, the cyclopentanone derivative of the formula IX obtained in the preceding Step 3 is methylene-modified to obtain an exo-methylene derivative of the formula X. This methylene-modification reaction is conducted in tetrahydrofuran by using a reagent prepared from zinc-methylenebromide-titanium tetrachloride. The methylene-modification reaction is conducted in a halogenated hydrocarbon solvent such as methylene chloride, and the reaction temperature is selected within a range of from 0° to 50° C.

Step 5

In this step, the exo-methylene derivative of the formula X obtained in the preceding Step 4 is subjected to a hydration reaction to obtain a hydroxymethylcyclopentane derivative of the formula XI. The hydration reaction of this step is conducted by hydroborate-modification, followed by oxidation. For the hydroborate-modification, a hydroborate-modification agent such as disiamylborane, 9-BBN (9-borabicyclo[3,3,1]nonane) or texylborane, may be employed. The hydroborate-modification agent is used usually in an amount of from 1 to 1.5 equivalent. The reaction is preferably conducted in a solvent. For example, an ether type solvent such as tetrahydrofuran, diglyme or diethyl ether can be used. The reaction proceeds smoothly at a temperature of from $-25°$ C. to room temperature. In this step, the hydroborate-modification is followed by oxidation without isolating the product. The oxidation can be conducted by using an oxidizing agent such as hydrogen peroxide. When the oxidation is conducted by using hydrogen peroxide, it is preferred to use it under an alkaline condition with e.g. sodium hydroxide. The oxidizing agent is used in an amount of from 5 to 15 equivalent, and the reaction proceeds smoothly within a range of from room temperature to 60° C.

Step 6

In this step, the hydroxymethylcyclopentane derivative of the formula XI obtained in the preceding Step 5 is reduced to obtain a diol having the formula XII. The reduction reaction can be conducted in an ether type solvent such as tetrahydrofuran or ethyl ether by using a reducing agent such as lithium aluminum hydride. The reaction temperature can be selected within a range of from 0° to 40° C.

Step 7

In this step, the diol of the formula XII obtained in the preceding Step 6, is oxidized and then subjected to aldol condensation involving dehydration, to obtain a 6-membered ring enal of the formula XIII.

For the oxidation, for example, dimethyl sulfoxide-oxalyl chloride or dimethyl sulfoxidepyridine complex of sulfur trioxide, may be used. The oxidizing agent is used usually in an amount of from 1 to 5 equivalent.

The reaction is conducted preferably in a solvent. As the solvent, a halogenated hydrocarbon such as methylene chloride can be used.

The reaction proceeds smoothly at a temperature of from $-70°$ C. to room temperature depending upon the type of the oxidizing agent.

In order to obtain an oxidized product in this step, a tertiary amine such as triethylamine or diisopropylethylamine, is added to the reaction product and the mixture is treated at a temperature of from $-70°$ C. to room temperature.

After the completion of the oxidation reaction, the formed product was subjected to the subsequent dehydration reaction without isolation. The dehydration reaction is carried out by heating the product obtained in the above oxidation reaction, in the presence of an acidic catalyst. As the acidic catalyst, an acid-ammonium salt can be used. The acid-ammonium salt catalyst can be prepared from an acid and an amine. Suitable acids include trifluoroacetic acid, toluenesulfonic acid, camphorsulfonic acid and acetic acid. Suitable amines include dibenzylamine, diethylamine, dimethylamine, diisopropylamine, piperidine and pyrrolidine, piperazine. These acids and amines may be suitably selected and is in combustion. Particularly preferred is a catalyst obtained by a combination of trifluoroacetic acid and dibenzylamine, since it is thereby possible to obtain the desired product in good yield. The amount of the catalyst may be at a level of 0.2 equivalent, but in order to conduct the reaction efficiently, it is preferred to employ the catalyst in an amount of about 1 equivalent.

The reaction is preferably conducted in the presence of a solvent. An aromatic hydrocarbon such as benzene, toluene or xylene may be employed as such a solvent.

The reaction temperature can be selected within a range of from room temperature to 100° C. However, in order to conduct the reaction smoothly, it is preferred to conduct the reaction within a range of from 50° to 70° C.

From the 6-membered ring enal of the formula XIII, the novel stable prostacyclin analogue of the formula I can be prepared by the following four routes.

ROUTE 1

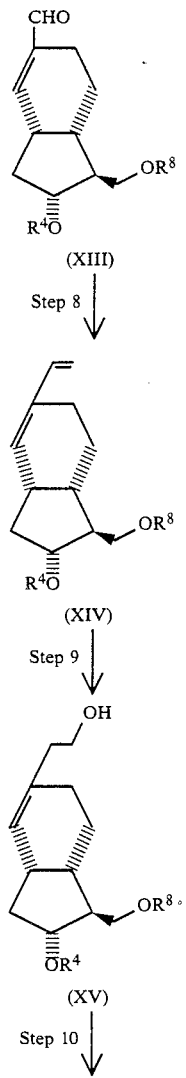

ROUTE 1
-continued
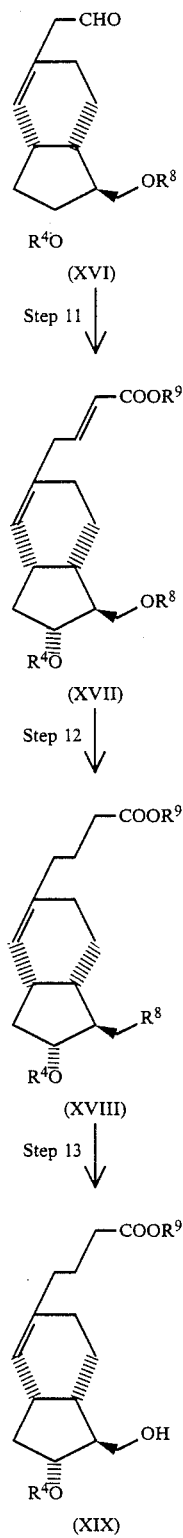
ROUTE 2
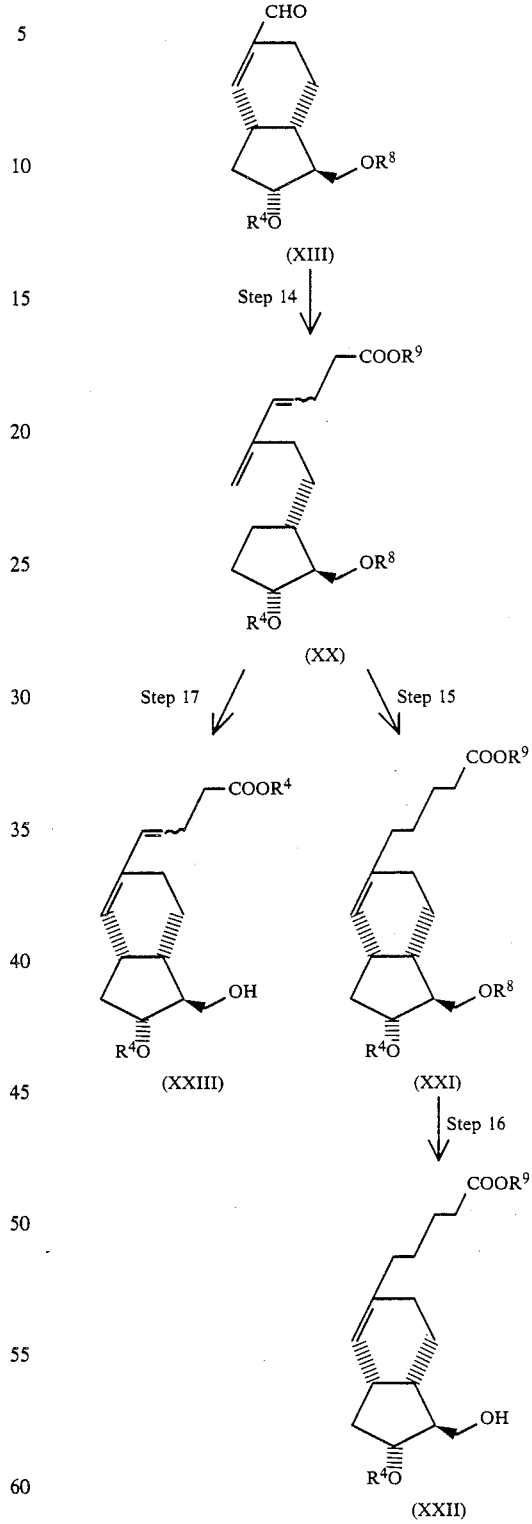
Step 8
In this step, the 6-membered ring enal of the formula XIII is methylene-modified to obtain a conjugated diene of the formula XIV. The methylene-modification reaction can be conducted in an ether-type solvent such as tetrahydrofuran by using an ylide compound prepared from methyltriphenylphosphonium bromide and a base such as a potassium salt of t-BuOH. The reaction temperature may be selected within a range of from 0° to 50° C.

Step 9

In this step, the conjugated diene of the formula XIV obtained in the preceding Step 8, is selectively hydroborate-modified, and then subjected to an oxidation reaction to obtain a primary alcohol of the formula XV. For this hydroborate-modification, a hydroborate modification agent such as disiamyl borane or 9-BBN is used. The reaction is preferably conducted in a solvent. For this purpose, an ether-type solvent such as tetrahydrofuran, diglyme or diethyl ether may be employed. For the oxidation after the hydroborate-modification, an oxidizing agent such as hydrogen peroxide may be employed under a basic condition.

Step 10

In this step, the primary alcohol of the formula XV obtained in the preceding Step 9 is oxidized to obtain an aldehyde of the formula XVI. This oxidation reaction can be conducted in a halogenated hydrocarbon solvent such as methylene chloride by using a Collins' reagent, pyridinium chlorochromate or a Swern oxidizing agent. The reaction temperature can be selected within a range of from −78° to 50° C.

Step 11

In this step, the aldehyde of the formula XVI obtained in the preceding Step 10 is subjected to a Wittig reaction to obtain an $\alpha, \beta$-unsaturated ester of the formula XVII.

This Wittig reaction is conducted in an aromatic hydrocarbon such as toluene or benzene by using a stable ylide such as carbomethoxymethylene triphenylphosphorane or carboethoxymethylene triphenylphosphorane. The stable ylide is used usually in an amount of from 1 to 2 equivalent, and the reaction proceeds smoothly at a temperature of from 50° to 130° C. In the formula XVII, $R^9$ is a lower alkyl group such as methyl, ethyl or propyl.

Step 12

In this step, the $\alpha, \beta$-unsaturated ester of the formula XVII obtained in the preceding Step 11, is selectively reduced to obtain an ester of the formula XVIII. This reduction reaction can be conducted in an ether-type solvent such as tetrahydrofuran by using a reducing agent such as lithium tri-sec-butylborohydride or copper (I) hydride. The reaction temperature may be selected within a range of from −78° C. to 0° C.

Step 13

In this step, the protective group of the primary hydroxyl group of the ester of the formula XVIII obtained in the preceding Step 12, is selectively removed to obtain a ω-chain primary alcohol of the formula XIX. The reaction condition for the removal of the protective group varies depending upon the type of $R^8$. In the case where $R^8$ is a trialkylsilyl group such as t-butyldimethylsilyl and $R^4$ is an acetal-type protective group such as a tetrahydropyranyl group, the reaction may be conducted in tetrahydrofuran by using tetra-n-butylammonium fluoride.

Step 14

In this step, the 6-membered enal of the formula XIII is subjected to a Wittig reaction, and then the carboxyl group is protected to obtain a 1,3-diene of the formula XX. For this Wittig reaction, an ylide prepared from 3-carboxypropyltriphenylphosphonium bromide and a potassium salt of t-BuOH, can be used. As the solvent for the reaction, an ether-type solvent such as tetrahydrofuran can be used, and the reaction temperature may be selected within a range of from −78° to 50° C. In this step, then the product obtained by the Wittig reaction, is esterified. In the case where $R^9$ is methyl, the reaction may be conducted in ethyl ether by using diazomethane, or in acetone by using potassium carbonate-methyl iodide. In the formula XX, $R^9$ is a lower alkyl group such as methyl, ethyl or propyl.

Step 15

In this step, the 1,3-diene of the formula XX is selectively reduced to obtain a monoene of the formula XXI. For this selective reduction, a catalytic reduction reaction is employed. The hydrogen pressure used for the catalytic reduction reaction is usually 1 atm. As the reducing catalyst, 5% Pd-C, 10% Pd-C or a Wilkinson complex can be used. The solvent for the reduction can be selected from a wide range of solvents such as methanol, ethanol, benzene and ethyl acetate. Likewise, the reaction temperature can be selected from a wide range of from −78° to 50° C.

Step 16

In this step, the protective group of the primary hydroxyl group of the monoene of the fromula XXI obtained in the preceding Step 15, is selectively removed to obtain a ω'-chain primary alcohol of the formula XXII. The reaction condition for the removal of the protective group varies depending upon the type of $R^8$. In the case where $R^8$ is a trialkylsilyl group such as t-butyldimethylsilyl and $R^4$ is an acetal-type protective group such as tetrahydropyranyl, the reaction may be conducted in tetrahydrofuran by using tetra-n-butylammonium fluoride.

Step 17

In this step, the protective group of the primary hydroxyl group of the 1,3-diene of the formula XX obtained in the Step 14, is selectively removed to obtain a ω'''-chain primary alcohol of the formula XXIII. The reaction condition for the removal of this protective group varies depending upon the type of $R_8$. In the case where $R^8$ is a trialkylsilyl group such as t-butyldimethylsilyl and $R_4$ is an acetal-type protective group such as tetrahydropyranyl, the reaction may be conducted in tetrahydrofuran by using tetra-n-butylammonium fluoride.

ROUTE 3

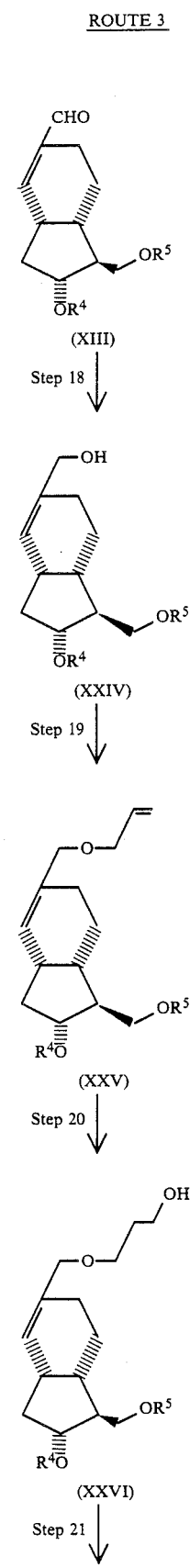

(XIII)

Step 18 ↓

(XXIV)

Step 19 ↓

(XXV)

Step 20 ↓

(XXVI)

Step 21 ↓

-continued
ROUTE 3

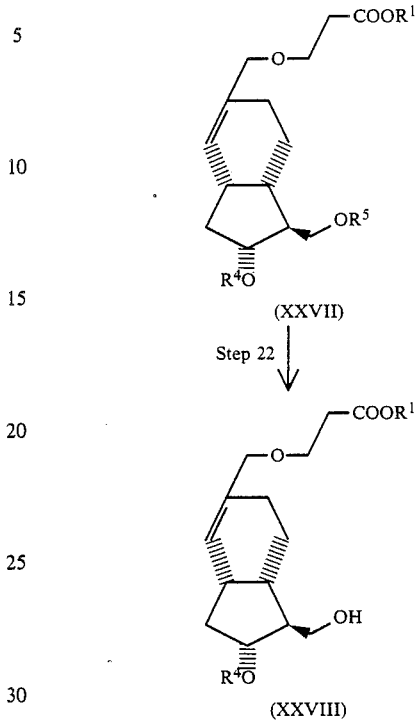

(XXVII)

Step 22 ↓

(XXVIII)

Step 18

In this step, the enal of the formula XIII is reduced to obtain an allyl alcohol of the formula XXIV. As the reducing agent for this step, sodium borohydride, lithium aluminum hydride or diisobutylaluminum hydride, may be employed. The reaction temperature may be selected within a range of from −78° to −50° C. The reduction reaction is conducted in a solvent. The useful solvent varies depending upon the type of the reducing agent. When sodium borohydride is used, an alcohol-type solvent such as methanol or ethanol may be employed. Likewise, when diisobutylaluminum hydride is used, toluene or methylene chloride may be employed.

Step 19

In this step, an allyl ether of the formula XXV is prepared from the allyl alcohol of the formula XXIV obtained in the preceding Step 18. The reaction is such that allyl bromide and the allyl alcohol of the formula XXIV are condensed in the presence of sodium hydroxide and a phase transfer catalyst. As the phase transfer catalyst, tetrabutylammoniumhydrogen sulfate or the like may be employed. The reaction temperature may be selected within a range of from 0° to 80° C. As the solvent for reaction, a two phase system of water-methylene chloride can be employed.

Step 20

In this step, the allyl ether of the formula XXV obtained in the preceding Step 19 is subjected to hydroborate-modification, followed by an oxidation reaction, to obtain a primary alcohol of the formula XXVI. For the hydroborate-modification, a hydroborate-modification agent such as disiamylborane or 9-BBN may be employed. The reaction is preferably conducted in a solvent. For example, an ether-type solvent such as tetrahydrofuran, diglyme or diethyl ether may be employed. The oxidation after the hydroborate-modification can be conducted under a basic condition by using an oxidizing agent such as hydrogen peroxide.

Step 21

In this step, the primary alcohol of the formula XXVI obtained in the preceding Step 20, is subjected to an oxidation reaction, followed by esterification, to obtain a γ-oxa ester of the formula XXVII. The oxidation reaction is conducted in two stages. The first stage is conducted by a sulfur trioxide-pyridine complex in the presence of triethylamine, and the second stage is conducted in a system of sodium hydroxide-silver nitrate. For the oxidation reaction in the first stage, a solvent such as DMSO is employed. The subsequent esterification reaction is conducted in ethyl ether by using the diazomethane, for example, in the case of a methyl ester.

Step 22

In this step, the protective group of the primary hydroxyl group of the γ-oxa ester of the formula XXVII obtained in the preceding Step 21, is removed to obtain a bicyclo[4,3,0]nonane derivative of the formula XXVIII. The reaction condition for the removal of the protective group varies depending upon the type of $R^5$. In the case where $R^5$ is a trialkylsilyl group such as t-butyldimethylsilyl and $R_4$ is an acetal-type protective group such as tetrahydropyranyl, the reaction may be conducted in tetrahydrofuran by using tetra-n-butylammonium fluoride.

ROUTE 4

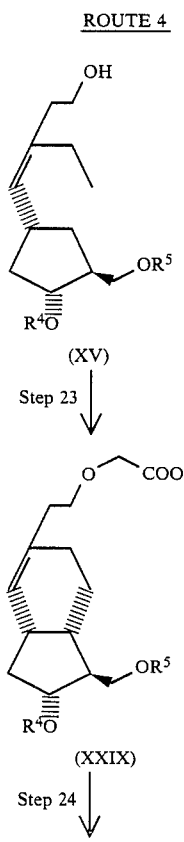

Step 23

In this step, a β-oxa ester of the formula XXIX is prepared from the hydroxyethyl compound of the formula XV. The reaction is such that t-butyl bromoacetate and the compound of the formula XV are condensed in the presence of sodium hydroxide and an interphase transfer catalyst. As the interphase transfer catalyst, tetrabutylammoniumhydrogen sulfate or the like may be employed. The reaction temperature may be selected within a range of from 0° to 80° C. As the solvent for reaction, a two phase system of water-methylene chloride is employed.

Step 24

In this step, the protective group of the primary hydroxyl group of the β-oxa ester of the formula XXIX obtained in the preceding Step 23, is removed to obtain a bicyclo[4,3,0]nonene derivative of the formula XXX. The reaction condition for the removal of the protective group varies depending upon the type of $R^5$. In the case where $R^5$ is a trialkylsilyl group such as t-butyldimethylsilyl and $R^4$ is an acetal-type protective group such as tetrahydropyranyl, the reaction is conducted in tetrahydrofuran by using tetra-n-butylammonium fluoride.

From the compounds of the formulas XIX, XXII, XXIII, XXVIII and XXX, the novel stable prostacyclin of the formula I can be prepared by the following five routes.

-continued
ROUTE 4

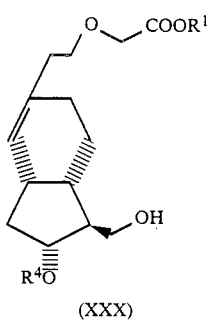

(XXX)

ROUTE 5

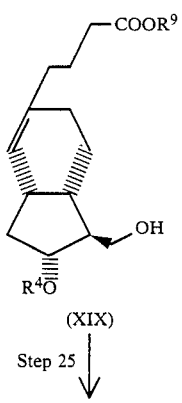

(XIX)

Step 25

-continued
ROUTE 5
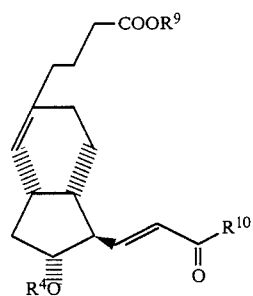
(XXXI)
Step 26 ↓
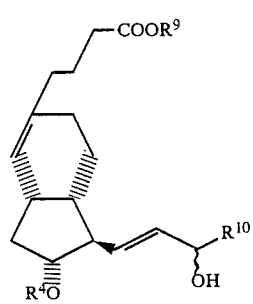
(I)
Step 27 ↓
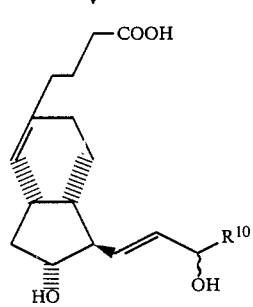
(I)
ROUTE 6
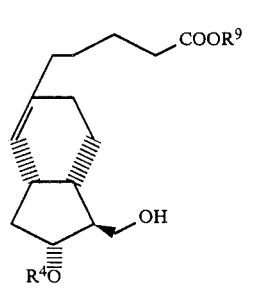
(XXII)
Step 28 ↓
-continued
ROUTE 6
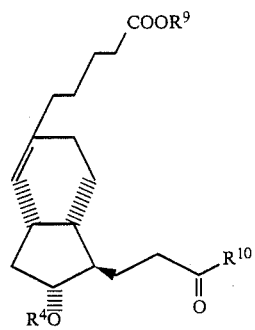
(XXXII)
Step 29 ↓
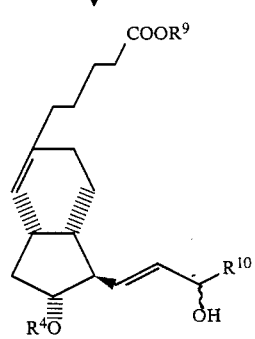
(I)
Step 30 ↓
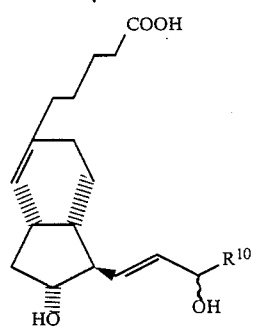
(I)
ROUTE 7
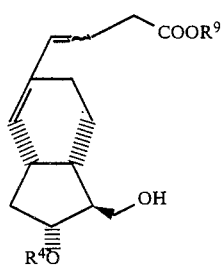 (XXIII)
Step 31 ↓

-continued
ROUTE 7
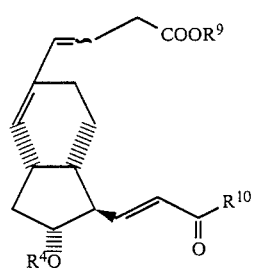
(XXXIII)
Step 32
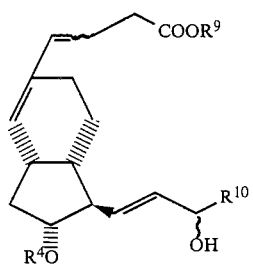
(I)
Step 33
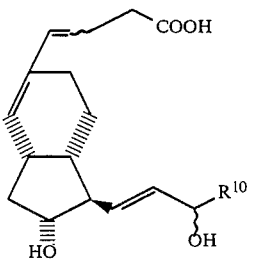
(I)
ROUTE 8
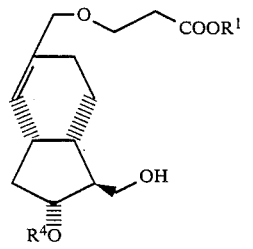
(XXVIII)
Step 34
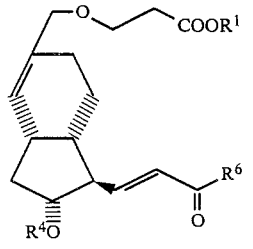
(XXXIV)
-continued
ROUTE 8
Step 35
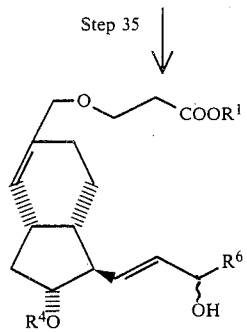
(I)
Step 36
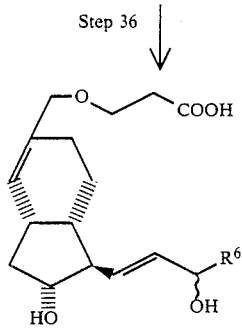
(I)
ROUTE 9
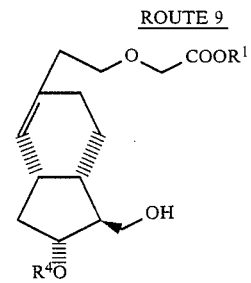
(XXX)
Step 37
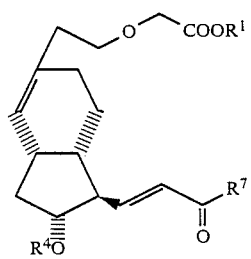
(XXXV)
Step 38
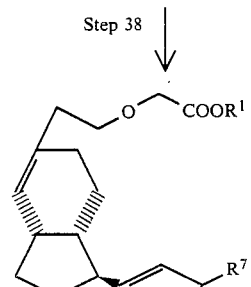
(I)

-continued
ROUTE 9

Step 39 ↓

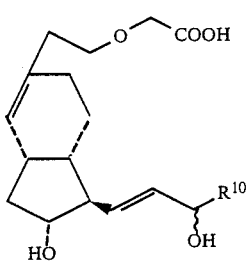

(I)

Step 25

In this step, the ω-chain primary alcohol of the formula XIX is oxidized and then subjected to a Wittig reaction to obtain a conjugated enone of the formula XXXI. The oxidation reaction can be conducted in a haloganated hydrocarbon such as methylene chloride by using a Collins' reagent or a sulfur trioxide-pyridine complex. The reaction temperature may be selected within a range of from −78° to 50° C.

In this step, the product obtained by the oxidation is then subjected to the Wittig reaction without isolating it. As the reactant, dimethyl(2-oxoheptyl)phosphonate or dimethyl(2-oxo-3-methyl-5-octynyl)phosphonate may be employed. This Wittig reaction is preferably conducted in the presence of a base in order to obtain the desired product in good yield. A base such as sodium hydride, butyllithium or t-butoxypostassium may be employed. The reaction is preferably conducted in a solvent. As a solvent, an ether-type solvent such as tetrahydrofuran, dimethoxyethane or diethyl ether or an aromatic solvent such as benzene, toluene or xylene, may be employed. The reaction temperature may be selected within a range of from −25° to 50° C.

Step 26

In this step, the compound of the formula XXXI obtained in the preceding Step 25 is reduced to obtain an allyl alcohol of the formula I. For this reduction, a reducing agent such as sodium borohydride or zinc borohydride may be employed. The solvent for the reaction may be methanol, ethanol, dimethoxyethane, ethyl ether, tetrahydrofuran, or the like. The reaction temperature may be selected within a range of from −50° to 50° C.

Step 27

In this step, the allyl alcohol of the formula I obtained in the preceding Step 26 is subjected to the removal of the protective group for the hydroxyl group and then, the hydrolysis of the ester to obtain the novel stable prostacyclin of the formula I. The removal of the protective group for the hydroxyl group varies depending upon the type of $R^4$. In the case where $R^4$ is a tetrahydropyranyl group, the reaction can be conducted in an acetic acid-$H_2O$-THF system by heating at a temperature of from 20° to 80° C. The hydrolysis of the ester can be conducted under a usual reaction condition i.e. in a $H_2O$-MeOH system or in a $H_2O$-EtOH system by using sodium hydroxide or potassium hydroxide. The reaction temperature may be selected within a range of from 0° to 50° C.

The production processes of Routes 6, 7, 8 and 9 can be conducted under the same conditions as in Route 5.

Now, the synthesis of prostacyclins having a double bond between the 3- and 4-positions of the formula I will be described.

ROUTE 10

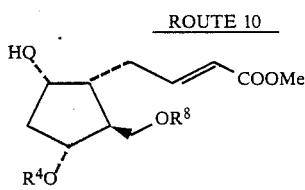 (VII)

Step 40 ↓

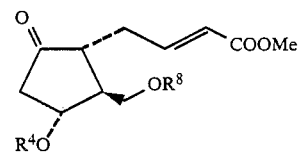 (XXXVI)

Step 41 ↓

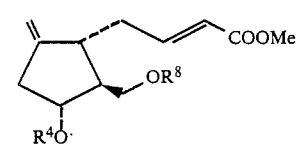 (XXXVII)

Step 42 ↓

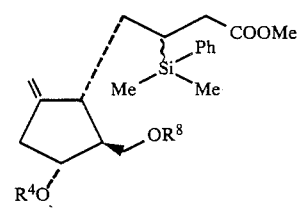 (XXXVIII)

Step 43 ↓

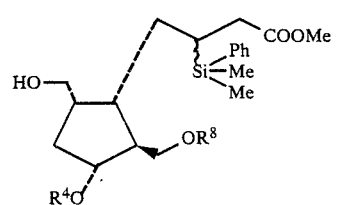 (XXXIX)

Step 44 ↓

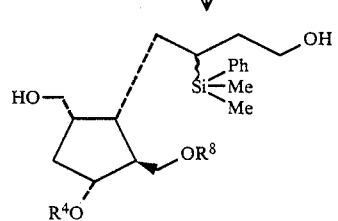 (XXXX)

-continued
ROUTE 10

Step 45

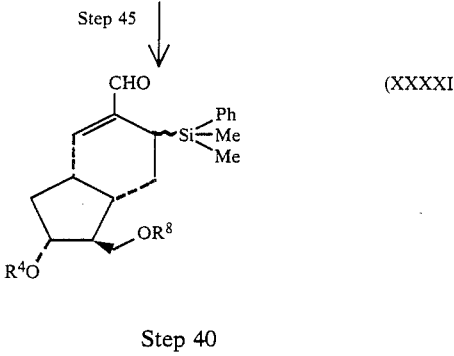
(XXXXI)

Step 40

In this step, the hydroxy-ester compound of the formula XII obtained in the Step 1, is oxidized to form a cyclopentanone derivative of the formula XXXVI.

This oxidation reaction can be conducted in the same manner as in the Step 3 described hereinbefore.

Step 41

In this step, the cyclopentanone derivative of the formula XXXVI obtained in the preceding Step 40, is subjected to methylene-modification to obtain an exo-methylene compound of the formula XXXVII. This methylene-modification reaction can be conducted in tetrahydrofuran by using a reagent prepared from zinc-methylene bromide-titanium tetrachloride.

This methylene-modification reaction can be conducted in the same manner as in the Step 4 described hereinbefore.

Step 42

In this step, a $R_3R_2R_1Si$ group is added for conjugation to the exo-methylene compound of the formula XXXVII obtained in the preceding Step 41, to obtain a β-trialkylsilyl ester derivative of the formula XXXVIII. For this conjugation addition reaction, an organic copper reagent prepared from trimethylsilyllithium or dimethylphenylsilyllithium, is employed. The reaction proceeds smoothly in tetrahydrofuran or in an ether solvent at a temperature of from −78° C. to room temperature.

Step 43

In this step, the β-trialkylsilyl-ester derivative of the formula XXXVIII obtained in the preceding Step 42 is subjected to hydration reaction to obtain a hydroxymethylcyclopenthane derivative of the formula XXXIX. The hydration reaction in this step can be conducted in the same manner as in the Step 5 described hereinbefore.

Step 44

In this step, the hydroxymethylcyclopenthane derivative of the formula XXXIX obtained in the preceding Step 43, is reduced to obtain a diol compound of the formula XXXX. This reduction reaction can be conducted in the same manner as in the Step 6 described hereinbefore.

Step 45

In this step, the diol compound of the formula XXXX obtained in the preceding Step 45, is oxidized and then subjected to aldol condensation involving dehydration, to obtain a 3-formyl-4-trialkylsilyl-cis-bicyclo[4,3,0-]nona-2-ene derivative of the formula XXXXI. This oxidation reaction followed by the aldol condensation can be conducted in the same manner as in the Step 7 described hereinbefore.

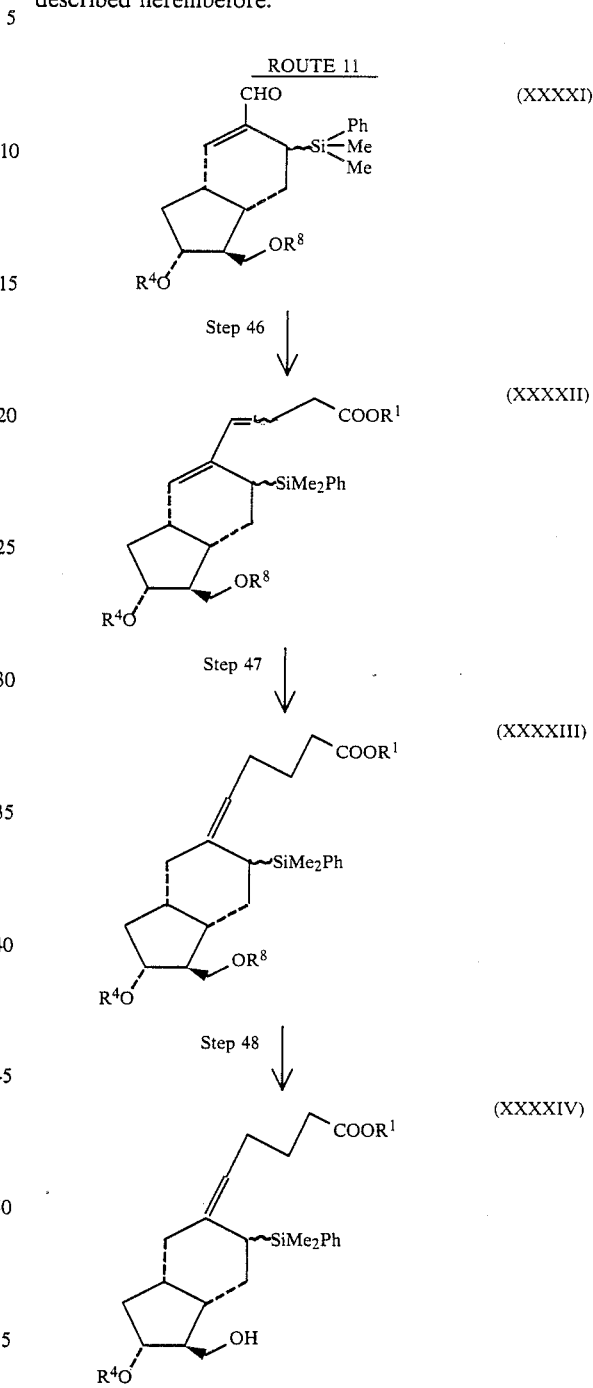

Step 46

In this step, the 3-formyl-4-trialkylsilyl-cis-bicyclo[4,3,0]nona-2-ene derivative of the formula XXXXI obtained in the preceding Step 45, is subjected to a Wittig reaction, followed by esterification to obtain a conjugated diene of the formula XXXXII. This Wittig reaction followed by the esterification can be conducted in the same manner as in the Step 14 described hereinbefore.

Step 47

In this step, the conjugated diene of the formula XXXXII obtained in the preceding Step 46, is subjected to a 1,4-reduction reaction to obtain an allylsilane of the formula XXXXIII. For the 1,4-reduction reaction, a catalyst of naphthalene-Cr(CO)$_3$ or (methyl benzoate) Cr(CO)$_3$ is used in an amount of from 0.1 to 30 mol%. The reaction temperature varies depending upon the type of the solvent, but may be selected within a range of from room temperature to 150° C. As the solvent for the reaction, acetone, tetrahydrofuran or acetonitrile may be used. The hydrogen pressure varies depending upon the type of the solvent used, but may be selected within a range of from 1 to 150 atm.

Step 48

In this step, the allylsilane of the formula XXXXIII obtained in the preceding Step 47 is subjected to a reaction for the removal of the protective group, to obtain a primary alcohol derivative of the formula XXXXIV.

The reaction condition for the removal of the protective group varies depending upon the type of $R^8$. In the case where $R^8$ is a trialkylsilyl group such as t-butyldimethylsilyl and $R^4$ is an acetal-type protective group such as tetrahydropyranyl, the reaction can be conducted in tetrahydrofuran by using tetra-n-butylammonium fluoride.

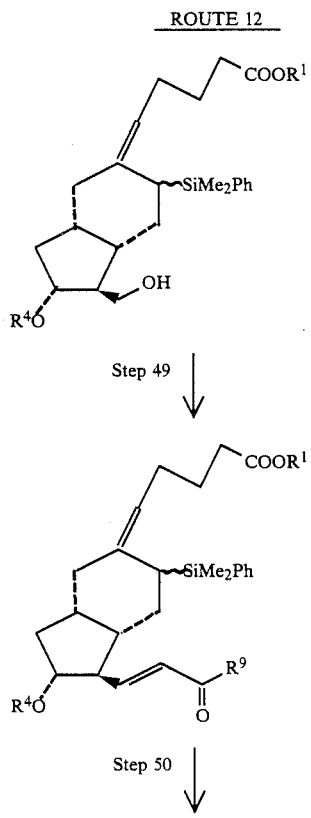

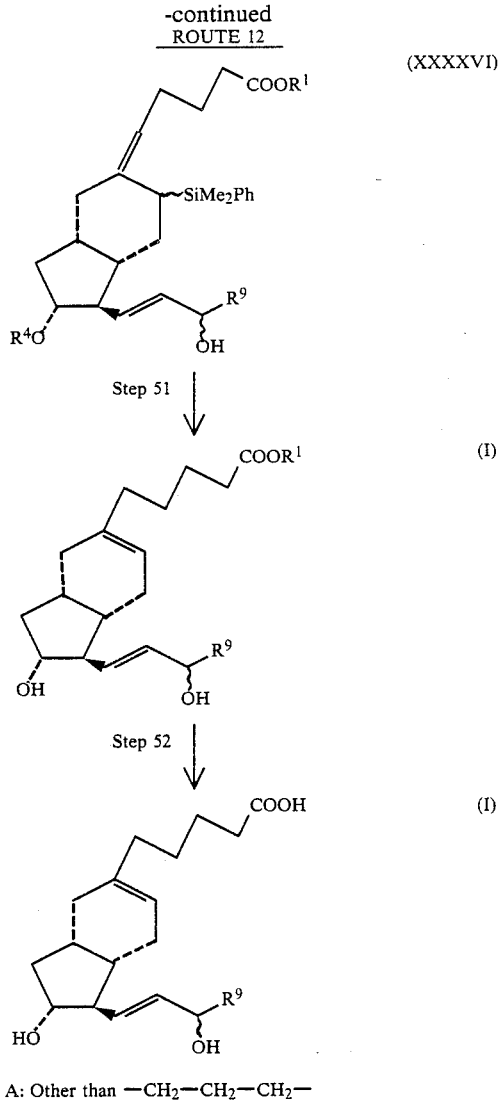

A: Other than —CH$_2$—CH$_2$—CH$_2$—

Step 49

In this step, the primary alcohol derivative of the formula XXXXIV is oxidized and then subjected to a Wittig reaction to obtain a conjugated enone of the formula XXXXV. This oxidation reaction followed by the Wittig reaction may be conducted in the same manner as in the Step 25 described hereinbefore.

Step 50

In this step, the compound of the formula XXXXV obtained in the preceding Step 49, is reduced to obtain an allyl alcohol of the formula XXXXVI. This reduction can be conducted in the same manner as in the Step 26 described hereinbefore.

Step 51

In this step, the compound of the formula XXXXVI obtained in the preceding Step 50, is subjected to a protodesilyl reaction and at the same time the protective group for the hydroxyl group is removed, to obtain a homoisocarbacyclin analogue of the formula 1. For the protodesilyl reaction and the removal of the protective group, an acidic catalyst is required, and p-toluenesulfonic acid, camphosulfonic acid or hydrogen iodide can be used as the acidic catalyst. The reaction is conducted in a solvent within a range of from 0° to 100° C., and water-containing acetonitrile, water-containing benzene or water-containing tetrahydrofuran may be used as the solvent.

Step 52

In this step, the ester portion of the homoisocarbacyclin analogue of the formula 1 is hydrorized to obtain a prostacyclin analogue of the formula I. The hydrolysis of the ester can be conducted under a usual reaction condition i.e. in a H2O-MeOH system by using potassium hydroxide. The reaction temperature may be selected within a range from 0° to 50° C.

Further, a compound of the formula I wherein A is —CH=CHCH2CH2— can be prepared in the same manner as in the following synthesis, and a compound of the formula I wherein A is —CH2CH2CH2— can be prepared by increasing the carbon chain of the 3-formyl-4-trialkylsilyl-cis-bicyclo[4,3,0]nona-2-ene derivative of the formula XXXXI by 1 and then subjecting it to a Wittig reaction with (carbomethoxymethylene)triphenylphosphorane, followed by the reduction of the α,β-unsaturated ester, as the key process.

The present invention also relates to a blood circulation improving agent containing the prostacyclin analogue of the formula I as the active ingredient.

The present inventors have conducted extensive studies on the pharmaclological activities of the prostacyclin analogues. As a result, it has been found that as compared with the activity spectra such as the blood platelet agglutination inhibiting activities, the blood flow increasing activities in various organs, hypotensive activities, the anti-ulcer activities, etc. of known prostacyclin analogues, the group of compounds represented by the formula I has extremely high selectivity particularly for the blood platelet agglutination inhibiting activities. A further research has been made for the application to the prevention and treatment of various circuratory disorders and has finally accomplished the present invention.

The prostacyclin analogues of the present invention have low hypotensive activities, and yet show suitable blood flow increasing activities for various organs, and further they have high selectivity for the blood platelet agglutination inhibiting activities, whereby the conventional difficulties can be solved. Thus, according to the present invention, it is possible to provide a drug useful for the prevention and treatment of ischemic heart diseases such as myocardial infarction or angina pectoris, and circuratory disorders such as cerebral thrombosis, cerebral infarction and peripheral circulatory discorders. The following compounds may be mentioned as the prostacyclin derivatives of the formula I of the present invention:

(a) 3-(3-carboxypropyl)-7-exo-(3α-hydroxy-trans-1-octenyl)-8-endo-hydroxy-cis-bicyclo[4,3,0]nona-2-ene
(b) 3-(3-carboxypropyl)-7-exo-(3α-hydroxy-4,8-dimethyl-trans-1-octen-6-ynyl)-8-endo-hydroxy-cis-bicyclo[4,3,0]nona-2-ene
(c) 3-(4-carboxy-1-butenyl)-7-exo-(3α-hydroxy-trans-1-octenyl)-8-endo-hydroxy-cis-bicyclo[4,3,0]nona-2-ene
(d) 3-(4-carboxy-1-benenyl)-7exo-(3α-hydroxy-4,8-dimethyl-trans-1-octen-6-ynyl)-8-endo-hydroxy-cis-bicyclo[4,3,0]nona-2-ene
(e) 3-(4-carboxybutyl)-7-exo-(3α-hydroxy-trans-1-octenyl)-8-endo-hydroxy-cis-bicyclo[4,3,0]nona-2-ene
(f) 3-(4-carboxybutyl)-7-exo-(3α-hydroxy-4,8-dimethyl-trans-1-octen-6-ynyl)-8-endo-hydroxy-cis-bicyclo[4,3,0]nona-2ene
(g) 3-(oxa-4-carboxybutyl)-7-exo-(3α-hydroxy-4,8-dimethyl-1-trans-octen-6-ynyl)-8-endo-hydroxy-cis-bicyclo[4,3,0]nona-2-ene
(h) 3-(2-oxa-4-carboxybutyl)-7-exo-(3α-hydroxy-4,8-dimethyl-1-trans-octen-6-ynyl)-8-endo-hydroxy-cis-bicyclo[4,3,0]nona-2-ene
(i) 3-(4-carboxybutyl)-7-exo-(3α-hydroxy-4,8-dimethyl-1-trans-octen-6-ynyl)-8-endo-hydroxy-cis-bicyclo[4,3,0]nona-3-ene In the present invention, for example, compound (b) has a hypotensive activity of about 1/135 of the activity of prostacyclin, but the blood platelet agglutination inhibiting activity as evaluated by collagen agglutination is 1/12, and it further has an activity to increase the blood flow of the vertebral artery, coronary artery and femoral artery. Further, with compound (c), the hypotensive activity is as weak as about 1/125 of the activity of prostacyclin, but its blood platelet agglutination inhibiting activity as evaluated by ADP agglutination is 1/17, and like compound (b), it has an activity to increase the blood flow of various organs to a proper extent. Thus, the object of the present invention as a blood circulation improving agent can be adequeately accomplished.

Further, the present invention provides an anti-ulcer composition comprising an effective amount of the prostacyclin analogue as described above and a pharmaceutically acceptable carrier.

The present inventors have made detailed studies on the pharmacological activities of the prostacyclin analogues, and as a result, have found that the group of compounds represented by the formula I have remarkable anti-ulcer activities, even by oral administration, against ethanol ulcer, hydrochloric acid ulcer and indomethacine ulcer in animals. On the basis of this discovery, a further research has been made for the application to the prevention and treatment of digestive organ ulcers, and have accomplished the present invention.

The prostacyclin analogues of the present invention have hypotensive activities which are weak as compared with the hypotentive activities of other conventional prostacyclin analogues, and they do not cause diarrhea, which has been a stumbling block to the clinical application of PGE2 analogues. Thus, they are superior in the selectivity of the activities, whereby the difficulties of the known PG analogues have been overcome. Thus, it is possible to provide a drug which is highly useful against gastric mucosal troubles i.e. acute mucosal troubles due to a food, an alcohol or a drug, and localized chronic tissue failures such as digestive ulcer.

Specific examples of the prostacyclin analogues of the present invention, includes:
(a) 3-(3-carboxypropyl)-7-exo-(3α-hydroxy-trans-1-octenyl)-8-endo-hydroxy-cis-bicyclo[4,3,0]nona-2-ene
(b) 3-(3-carboxypropyl)-7-exo-(3α-hydroxy-4,8-dimethyl-trans-1-octen-6-ynyl)-8-endo-hydroxy-cis-bicyclo[4,3,0]nona-2-ene (c) 3-(4-carboxy-1-butenyl)-7-exo-(3α-hydroxy-trans-1-octenyl)-8-endo-hydroxy-cis-bicyclo[4,3,0]nona-2-ene (d) 3-(4-carboxy-1-butenyl)-7-exo-(3α-hydroxy-4,8-dimethyl-trans-1-octen-6-ynyl)-8-endo-hydroxy-cis-bicyclo[4,3,0]nona-2-ene (e) 3-(4-carboxybutyl-7-exo-(3α-hydroxy-trans-1-octenyl)-8-endo-hydroxy-cis-bicyclo[4,3,0]nona-2-ene (f) 3-(4-carboxybutyl)-7-exo-(3α-hydroxy-4,8-dimethyl-trans-1-octen-6-ynyl)-8-endo-hydroxy-cis-bicyclo[4,3,0]nona-2-ene (g) 3-(3-oxa-4-carboxybutyl)-7-exo-(3α-hydroxy-4,8-dimethyl-1-trans-octen-6-ynyl)8-endo-hydroxy-cis-bicyclo[4,3,0]nona-2-ene (h) 3-(2-oxa-4-carboxybutyl)-7-exo-(3α-hydroxy-4,8-dimethyl-1-trans-octen-6-ynyl)-8-endo-hydroxy-cis-bicyclo[4,3,0]nona-2-ene (i) 3-(4-carboxybutyl)-7-exo-(3α-hydroxy-4,8-dimethyl-1-trans-octen-6-ynyl)-8-endo-hydroxy-cis-bicyclo[4,3,0]nona-3-ene The prostacyclin analogues of the present invention, such as compounds (b), (d) and (f), have anti-ulcer activities which are comparable or superior to typical PG having anti-ulcer activities, such as PGE$_2$. While the PGE$_2$ analogues are likely to induce diarrhea, the prostacyclin analogues of the present invention do not have such diarrhea-inducing activities. While prostacyclin has remarkable hypotensive activities, the hypotensive activities of the prostacyclin analogues of the present invention are very weak, and thus they are superior in the selectivities of activities, whereby the object of the present invention has an anti-ulcer composition can be sufficiently accomplished.

These compounds of the present invention can be administered orally or non-orally for the treatment.

The drugs for oral administration may be solid formulations such as powders, granules, capsules, tablets or liquid formulations such as syrups or elixirs. The drug for non-oral administration may be injection drugs, rectal administration drugs, skin application drugs or inhalation drugs. These drugs can be prepared in accordance with a conventional method by mixing such an active ingredient with a pharmaceutically acceptable carrier or adjuvant. Further, it may be made in the form of a long-lasting agent in accordance with a known technique.

For the preparation of solid formulations for oral administration, the active ingredient may be mixed with a carrier such as lactose, starch, crystalline cellulose, calcium lactate, magnesium metasilicate aluminate or silicic anhydride to obtain a powder, or if necessary, a binder such as sucrose, hydroxypropyl cellulose or polyvinylpyrroidone and a disintegrator such as carboxymethyl cellulose or calcium carboxymethyl cellulose, may be added and the mixture was subjected to wet or dry granulation to obtain granules. For the preparation of tablets, these powders or granules may be tabletted by themselves or after an addition of a lubricant such as magnesium stearate or talc. These granules or tablets may be formed into interic coating formulations by coating them with an enteric coating agent such as hydroxypropylmethyl cellulose stearate, methacrylic acid or a methyl methacrylate copolymer, or may be formulated into long-lasting formulations by coating them with ethyl cellulose, carnauba wax, hardened oil, etc.

For the preparation of capsules, the powders or granules, may be filled in hard capsules, or active ingredients may be dissolved in glycerol, polyethylene glycol, sesame oil, olive oil or the like, and then coated with gelatin film to obtain soft capsules.

For the preparation of liquid formulations for oral administration, an active ingredient and a sweetening agent such as sorbitol or glycerol, may be dissolved in water to obtain a clear cyrup, or refined oil or ethanol may be added thereto to obtain an elixir, or gum arabic or tragant, polysolvate 80 or sodium carboxy methyl cellulose, may be added thereto to obtain an emulsion or suspension. If desired, additives such as corrigents, coloring agents or storage agents may be added to these liquid formulations.

For the preparation of an injection solution, an active component may be dissolved in distilled water for injection, if necessary, together with a pH controlling agent such as hydrochloric acid, sodium hydroxide, lactic acid, sodium lactate, sodium hydrogen phosphate or sodium dihydrogen phosphate, and an isotonic agent such as sodium chloride or glucose, then septically filtered and filled in an ample, or mannitol, dextrin, cyclodextrin, gelatin or the like may be added thereto, followed by freeze drying under vacuum, to obtain an injection drug of the type which is to be dissolved at the time of the injection. Further, it is possible to prepare an emulsion for injection by emulsifying an active ingredient in water by an addition of lecitin, polysolvate 80 or polyoxyethylene hardened caster oil.

For the preparation of a rectal administration drug, an active ingredient and a suppository material such as cacao butter, fatty acid tri-, di- or mono-glyceride or polyethylene glycol, may be moistened, melted, poured in a mold and cooled, or an active ingredient may be dissolved in polyethylene glycol, soybean oil or the like, followed by coating with a gelatin film.

For the preparation of a skin application drug, an active ingredient may be added to white vaseline, beeswax, liquid paraffin, polyethylene glycol or the like, and the mixture is kneaded, if necessary under heating, to obtain an ointment, or it may be kneaded with an adhesive agent such as rosin or an alkyl acrylate polymer, and the mixture is then spread on a non-woven fabric of polyethylene, etc. to obtain a tape drug.

For the preparation of an inhalation drug, an active ingredient is dissolved or dispersed in a propellant such as Freon gas and filled in a pressure resistant container to obtain an aerosol.

The dose of the prostacyclin analogue of the present invention varies depending upon the age, the weight and the diseased state of the patient, but is usually within a range of from 1 μg to 500 mg per day, and may be administered at once or in several times.

Now, the present invention will be described in further detailed with reference to Reference Examples, Synthesis Examples, Test Examples and Formulation Examples. However, it should be understood that the present invention is by no means restricted to these specific Examples.

REFERENCE EXAMPLE 1

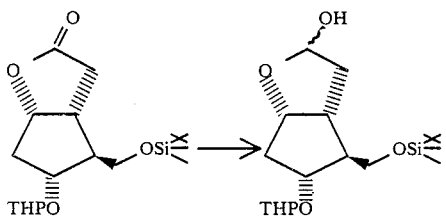

Under an argon atmosphere, 2-oxa-3-oxo-6-exo-t-butyldimethylsilyloxymethyl-7-endo-tetrahydropyranyloxybicyclo[3,3,0]octane (10 g, 27 mmol) was dissolved in toluene (80 ml), and cooled to −78° C. Then, diisobutylaluminum hydride (1M toluene solution 40.5 ml, 40.5 mmol) was added thereto, and the mixture was stirred at −78° C. for 60 minutes. Methanol was added at −78° C. until the generation of hydrogen was no longer observed. Then, the temperature was raised to room temperature. A saturated sodium chloride aqueous solution was added thereto, and the mixture was extracted with ethyl acetate. The extract was dried over anhydrous magnesium sulfate, and the solvent was distilled off to obtain 2-oxa-3-hydroxy-6-exo-t-butyldimethylsilyloxymethyl-7-endo-tetrahydropyranyloxybicyclo[3,3,0]octane (10.1 g, 100%).

IR (neat): 3430, 2950, 2860, 835 cm$^{-1}$.

NMR (CDCl$_3$) δ: 5.70–5.30 (m, 1H), 4.85–4.55 (m, 2H), 4.40–3.25 (m, 5H), 0.90 (s, 9H).

Mass m/z (%): 213 (5), 159 (17), 85 (100), 75 (19), 73 (13).

REFERENCE EXAMPLE 2

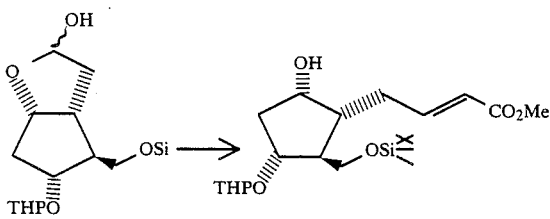

Under an argon atmosphere, 2-oxa-3-hydroxy-6-exo-t-butyldimethylsilyloxymethyl-7-endo-tetrahydropyranyloxybicyclo[3,3,0]octane (10.1 g, 27 mmol) was dissolved in toluene (100 ml). Then, (carbomethoxymethylene)triphenylphosphorane (11.7 g, 35 mmol) was added thereto, and the mixture was stirred at 60° C. for 12 hours. After cooling the mixture, the solvent was distilled off, and the residue thus obtained was purified by silica gel column chromatography (ethyl ether:n-hexane=1:2) to obtain 2α-(3-methoxycarbonyl-2-propenyl)-3β-t-butyldimethylsilyloxymethyl-4α-tetrahydropyranyloxy-1α-cyclopentanol (10.9 g, 94%).

IR (neat): 3530, 2960, 2875, 1730, 1660, 840 cm$^{-1}$.

NMR (CDCl$_3$) δ: 7.06 (m, 1H), 5.95 (d, J=15 Hz, 1H), 4.66 (bs, 1H), 3.70 (s, 3H), 0.90 (s, 9H), 0.05 (s, 6H).

Mass m/z (%): 211 (1), 159 (37), 85 (100), 75 (26), 73 (18), 43 (9).

REFERENCE EXAMPLE 3

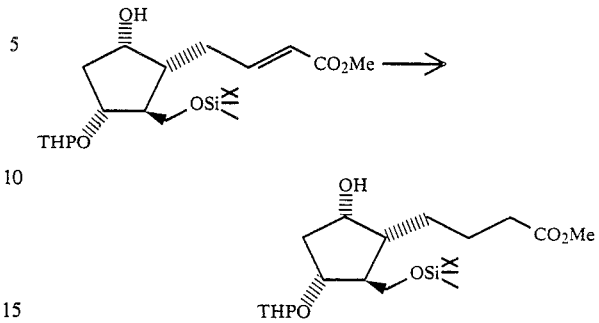

2α-(3-methoxycarbonyl-2-propenyl)-3β-t-butyldimethylsilyloxymethyl-4α-tetrahydropyranyloxy-1α-cyclopentanol (7.0 g, 16.4 mmol) was dissolved in methanol (50 ml). Then, 10% palladium-carbon (700 mg) was added thereto, and the mixture was stirred under a hydrogen atmosphere at room temperature for one hour. The catalyst was filtered off, and the solvent was distilled off from the filtrate to obtain 2α-(3-methoxycarbonylpropyl)-3β-t-butyldimethylsilyloxymethyl-4α-tetrahydropyranyloxy-1α-cyclopentanol (6.5 g, 93%).

IR (neat): 3520, 2940, 2850, 1738, 830 cm$^1$.

NMR (CDCl$_3$) δ: 4.67 (bs, 1H), 3.66 (s, 3H), 0.90 (s, 9H), 0.05 (s, 6H).

Mass m/z (%): 257 (10), 211 (1), 165 (29), 159 (62), 119 (11), 85 (100), 75 (28), 73 (22), 43 (12).

REFERENCE EXAMPLE 4

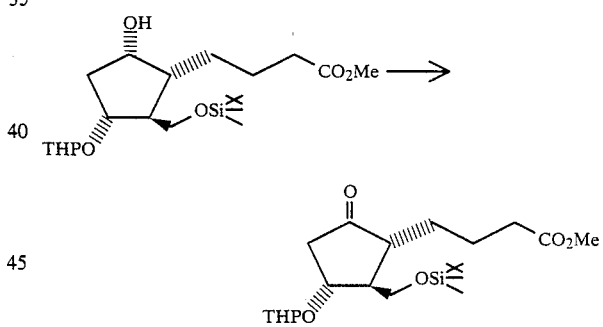

Under an argon atmosphere, oxalyl chloride (3.5 ml, 43.5 mmol) was dissolved in methylene chloride (30 ml). Then, a methylene chloride solution (30 ml) of diemthyl sulfoxide (6.5 ml, 90.6 mmol) was added thereto at −78° C. The mixture was stirred at −78° C. for 30 minutes, and a methylene chloride solution (50 ml) of 2α-(3-methoxycarbonylpropyl)-3β-t-butyldimethylsilyloxymethyl-4α-tetrahydropyranyloxy-1α-cyclopentanol (6.5 g, 15.1 mmol) was added thereto. The mixture was stirred at −78° C. for 30 minutes, and then triethylamine (31.3 ml, 226.5 mmol) was added thereto. The temperature was raised to room temperature. After an addition of water, the mixture was extracted with methylene chloride. The organic layer was washed with a saturated sodium chloride aqueous solution and dried over anhydrous magnesium sulfate. The solvent was distilled off, and the residue thus obtained was purified by silica gel column chromatography (ethyl ether:n-hexane=1:2) to obtain 2α-(3-methoxycarbonylpropyl)-3β-t-butyldimethylsilyloxymethyl- 4α-tetrahydropyranyloxy-1α-cyclopentanone (6.2 g, 95%).

IR (neat): 2900, 2810, 1730, 820 cm$^1$.

NMR (CDCl$_3$) δ: 4.63 (bs, 1H), 3.66 (s, 3H), 0.90 (s, 9H), 0.05 (s, 6H).

Mass m/z (%): 209 (2), 159 (28), 85 (100), 75 (29), 73 (29), 43 (3). 41 (22).

REFERENCE EXAMPLE 5

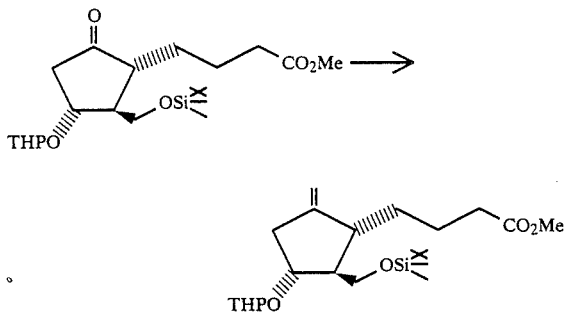

Under an argon atmosphere, 2α-(3-methoxycarbonyl-propyl)-3β-t-butyldimethylsilyloxymethyl-4β-tetrahydropyranyloxymethyl-1-cyclopentanone (10 g, 23 mmol) was dissolved in methylene chloride (100 ml), and a zinc-titanium chloride-methylene bromide reagent (Zn—TiCl$_4$—CH$_2$Br$_2$/THF) was added thereto at room temperature until the starting material dissapeared by TLC. The reaction solution was poured into a mixture of a saturated sodium bicarbonate aqueous solution (500 ml) and ethyl ether (500 ml). Celite was added to this mixture, and the mixture was filtered with celite. The ethyl ether layer was separated, and the aqueous layer was extructed with ethyl ether. The ethyl ether layers were put together, washed with a saturated sodium chloride aqueous solution and dried over anhydrous magnesium sulfate. Then, the solvent was distilled off, and the residue was purified by silica gel column chromatography (ethyl ether:n-hexane=1:6) to obtain 2α-(3-methoxycarbonylpropyl)-3β-t-butyldimethylsilyloxymethyl-4α-tetrahydropyranyloxy-1-cyclopentylidene (7.6 g, 76%).

IR (neat): 2900, 2800, 1730, 1645, 1240, 820 cm$^{-1}$.

NMR (CDCl$_3$) δ: 4.83 (d, 2H), 4.63 (bs, 1H), 3.80 (s, 3H), 0.90 (s, 9H), 0.05 (s, 6H).

Mass m/z (%): 193 (18), 159 (41), 85 (100), 75 (37), 73 (31), 43 (15).

REFERENCE EXAMPLE 6

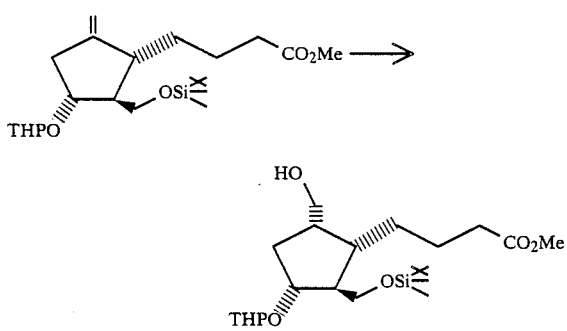

Under an argon atmosphere, 2α-(3-methoxycarbonyl-propyl)-3β-t-butyldimethylsilyloxymethyl-4α-tetrahydropyranyloxy-1-cyclopentylidene (7.5 g, 17.6 mmol) was dissolved in THF (70 ml). Then a THF solution of disiamylborane (0.9M, 43 ml, 38.7 mmol) was dropwise added thereto at 0° C. The mixture was stirred at 0° C. for one hour, and then a 6N sodium hydroxide aqueous solution (25.5 ml, 153 mmol) and a 30% hydrogen peroxide aqueous solution (22 ml, 194 mmol) were added thereto. The mixture was stirred at room temperature for one hour, and then extracted with ethyl acetate. The organic layer was washed with an aqueous sodium thiosulfate solution and a saturated sodium chloride aqueous solution, and then dried over anhydrous magnesium sulfate. Then, the solvent was distilled off to obtain a 1α-hydroxymethyl-2α-(3-methoxycarbonylpropyl)-3β-t-butyldimethylsilyloxymethyl-4α-tetrahydropyranyloxycyclopentane (7.8 g, 100%).

IR (neat): 3450, 2930, 2850, 835 cm$^{-1}$.

NMR (CDCl$_3$) δ: 4.66 (bs, 1H), 3.66 (s, 3H), 0.90 (s, 9H), 0.05 (s, 6H).

Mass m/z (%): 285 (15), 255 (9), 193 (30), 159 (54), 85 (100), 57 (100), 43 (52).

REFERENCE EXAMPLE 7

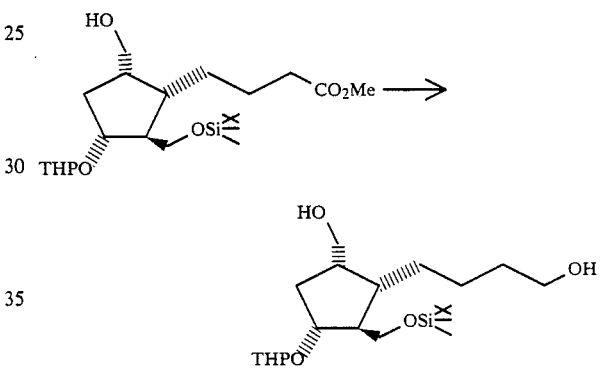

Under an argon atmosphere, lithium aluminum hydride (3.34 g, 88 mmol) was suspended in THF (70 ml). Then, a THF solution (100 ml) of 1α-hydroxymethyl-2α-(3-methoxycarbonylpropyl)-3α-t-butyldimethylsilyloxymethyl)-4α-tetrahydropyranyloxycyclopentane (7.8 g, 17.6 mmol) was dropwise added thereto under cooling with ice. The mixture was stirred under cooling with ice for 30 minutes, and then after an addition of sodium sulfate decahydrate, filtered with celite. The solvent was distilled off, and the residue was purified by silica gel column chromatography (ethyl ether) to obtain 1α-hydroxymethyl-2α-(4-hydroxybutyl)-3β-t-butyldimethyl-silyloxymethyl-4α-tetrahydropyranyloxy-cyclopentane (6.8 g, 93%).

IR (neat): 2950, 2870, 1680, 1630, 835 cm$^{-1}$.

NMR (CDCl$_3$) δ: 9.43 (s, 1H), 6.70 (bs, 1H), 4.63 (bs, 1H), 0.90 (s, 9H), 0.05 (s, 6H).

Mass m/z (%): 309 (M$^+$−85, trace), 159 (33), 85 (100), 75 (26), 73 (10), 57 (14).

REFERENCE EXAMPLE 8

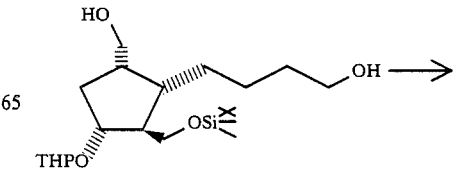

-continued

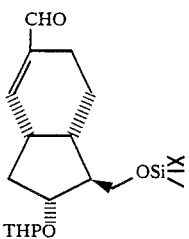

Under an argon atmosphere, oxalyl chloride (9 ml, 105.6 mmol) was dissolved in methylene chloride (70 ml). Then, a methylene chloride solution (40 ml) of dimethyl sulfoxide (16.2 ml, 228.8 mmol) was added thereto at −78° C. The mixture was stirred at −78° C. for 30 minutes, and then a methylene chloride solution (40 ml) of 1α-hydroxymethyl-2α-(4-hydroxybutyl)-3β-t-butyldimethylsilyloxymethyl-4α-tetrahydropyranyloxycyclopentane (6.8 g, 16.4 mmol) was added thereto. The mixture was stirred at −78° C. for 30 minutes, and after an addition of triethylamine (73 ml, 528 mmol), the temperature was raised to room temperature. Methylene chloride was distilled off. Under an argon atmosphere, benzene (150 ml) and dibenzylammoniumtrifluoro acetate (51 g, 16.4 mmol) were added thereto, and the mixture was stirred at 60° C. for 5 hours. The mixture was left to cool, and after an addition of water, extracted with ethyl ether. The ethyl ether layer was washed with a saturated ammonium chloride aqueous solution, a saturated sodium dicarbonate aqueous solution and water. The mixture was dried over anhydrous magnesium sulfate, and the solvent was distilled off. The residue was purified by silica gel column chromatography (ethyl ether:n-hexane=4:1) to obtain 3-formyl-7-exo-t-butyldimethylsilyloxymethyl-8-endo-tetrahydropyranyloxybicyclo[4,3,0]nona-2-ene (3 g, 46%).

IR (neat): 2950, 2870, 1680, 1630, 835 cm$^{-1}$.

NMR (CDCl$_3$) δ: 943 (s, 1H), 6.70 (bs, 1H), 4.63 (bs, 1H), 0.90 (s, 9H), 0.05 (s, 6H).

Mass m/z (%): 309 (M$^+$−85, trace), 159 (33), 85 (100), 75 (26), 73 (10), 57 (14).

REFERENCE EXAMPLE 9

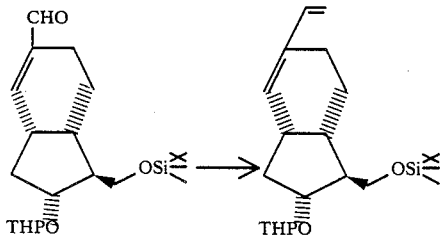

Under an argon atmosphere, methyltriphenylphosphonium bromide (449 mg, 1.14 mmol) preliminarily adequately dried at 100° C. under reduced pressure, was suspended in THF (5 ml). Then, a THF solution (2 ml) of potassium t-butoxide (140 mg, 1.14 mmol) was added thereto at room temperature. The mixture was stirred for 10 minutes, and then a THF solution (2 ml) of 3-formyl-7-exo-t-butyl-dimethylsilyloxymethyl-8-endo-tetrahydropyranyloxybicyclo[4,3,0]nona-2ene (150 mg, 0.38 mmol) was added. The mixture was stirred at room temperature for 30 minutes. After an additiion of a saturated ammonium chloride aqueous solution, the mixture was extracted with ethyl ether. The ethyl ether layer was washed with a saturated sodium chloride aqueous solution, and then dried over anhydrous magnesium sulfate. Then, the solvent was distilled off. The residue was purified by silica gel column chromatography (ethyl ether:n-hexane=1:15) to obtain 3-ethenyl-7-exo-t-butyldimethylsilyl-oxymethyl-8-endo-tetrahydropyranyloxybicyclo[4,3,0]nona-2-ene (139 mg, 93%).

IR (neat): 2950, 2875, 1640, 1605, 1475, 1260, 1200, 840, 780 cm=$^1$.

NMR (CDCl$_3$) δ: 6.33 (dd, J=11.6 Hz, 1H), 5.66 (bs, 1H), 5.03 (d, J=20 Hz, 1 H), 4.88 (d, J=11.6 Hz, 1H), 4.60 (bs, 1H), 0.90 (s, 9H), 0.05 (s, 6H).

Mass m/z (%): 374 (M+H$_2$O, trace), 308 (7), 251 (18), 205 (3), 159 (77), 85 (100), 57 (19).

REFERENCE EXAMPLE 10

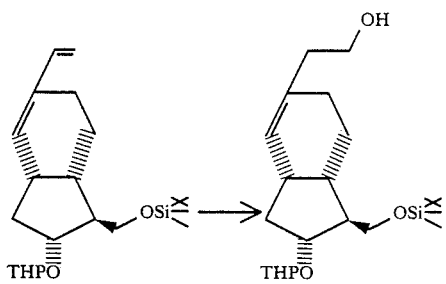

Under an argon atmosphere, 3-ethenyl-7-exo-t-butyl-dimethylsilyloxymethyl-8-endo-tetrhydropyranyloxybicyclo[4,3,0]nona-2-ene (245 mg, 0.63 mmol) was dissolved in THF (4 ml). Then a THF solution of disiamylborane (0.91M 1.7 ml, 1.58 mmol) was dropwise added at 0° C. The mixture was stirred at 0° C. for one hour. After an addition of a 6N sodium hydroxide aqueous solution (1.13 ml, 6.78 mmol) and a 30% hydrogen peroxide aqueous solution (0.94 ml, 8.29 mol) at 0° C., the mixture was stirred at room temperature for one hour. After an addition of water, the mixture was extracted with ethyl acetate. The organic layer was washed with a sodium thiosulfate aqueous solution and a saturated sodium chloride aqueous solution, and dried over anhydrous magnesium sulfate. Then, the solvent was distilled off. The residue was purified by silica gel column chromatography (ethyl ether:n-hexane=1:3) to obtain 3-(2-hydroxyethyl)-7-exo-t-butyldimethylsilyloxymethyl-8-endo-tetrahydropyranyloxybicyclo[4,3,0]-nona-2-ene (259 mg, 100%).

IR (neat): 3450, 2930, 2860, 1475, 1255, 1200, 835, 775 cm$^{-1}$.

NMR (CDCl$_3$) δ: 5.40 (bs, 1H), 4.56 (bs, 1H), 0.90 (s, 9 H), 0.50 (s, 6H).

Mass m/z (%): 410 (M+trace), 326 (7), 269 (9), 177 (44), 159 (91), 85 (100), 41 (30).

REFERENCE EXAMPLE 11

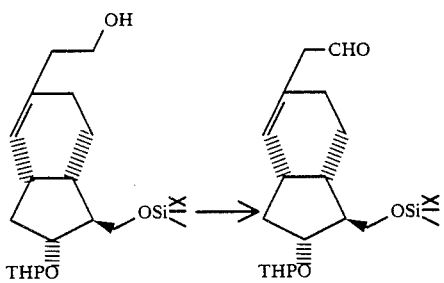

Under an argon atmosphere, chromic acid (610 mg, 6.1 mmol) was suspended in methylene chloride (10 ml), and pyridine (1 ml, 12.2 mmol) was dropwise added thereto. The mixture was stirred at room temperature for 15 minutes, and then a methylene chloride solution (10 ml) of 3-(2-hydroxyethyl)-7-exo-t-butyldimethylsilyloxymethyl-8-endo-tetrahydropyranyloxybicyclo[4,3,0]nona-2-ene (259 mg, 0.61 mmol) was added thereto. The mixture was stirred at room temperature for 15 minutes. The reaction solution was diluted with ethyl ether, and the reaction solution was filtered by florizil cloumn chromatography (ethyl ether), and washed with ethyl ether. The solvent was distilled off, and pyridine was adequeately distilled off by a vacuum pump. The residue was purified by silica gel column chromatography (ethyl ether:n-hexane=1:5) to obtain 3-(1-formylmethyl)-7-exo-t-butyldimethylsilyloxymethyl-8-endo-tetrahydropyranyloxybicyclo[4,3,0]nona-2-ene (180 mg, 73%).

IR (neat): 2950, 2850, 1730, 1475, 1255, 1200, 835, 775 cm$^{-1}$.

NMR (CDCl$_3$) δ: 9.56 (t, 1H), 5.50 (bs, 1H), 4.55 (bs, 1H), 2.94 (d, 1H), 0.90 (s, 9H), 0.05 (s, 6H).

Mass m/z (%): 324 (M$^+$ −84, 4), 267 (27), 249 (13), 159 (100), 85 (100).

REFERENCE EXAMPLE 12

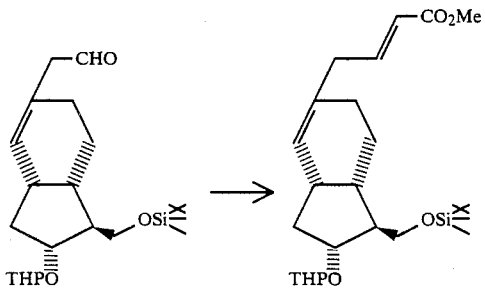

Under an argon atmosphere, 3-(1-formylmethyl)-7-exo-t-butyldimethylsilyloxymethyl-8-endo-tetrahydropyranyloxybicyclo[4,3,0]nona-2-ene (180 mg, 0.44 mmol) was dissolved in toluene (1.5 ml). Then, (carbomethoxymethylene)triphenylphosphorane (220 mg, 0.66 mmol) was added thereto, and the mixture was stirred at 60° C. for 4 hours. The solvent was distilled off, and the residue was purified by silica gel column chromatography (ethyl ether:n-hexane=1:4) to obtain 3-(3-methoxycarbonyl-2-propenyl)-7-exo-t-butyldimethylsilyloxymethyl-8-endo-tetrahydropyranyloxybicyclo[4,3,0]nona-2-ene (201 mg, 98%).

IR (neat): 2910, 2840, 1720, 1640, 1455, 1420, 1190, 825, 765 cm$^{-1}$.

NMR (CDCl$_3$) δ: 6.60 (dt, J=16.7 Hz, 1H), 5.84 (d, J=16.7 Hz, 1H), 5.42 (bs, 1H), 4.60 (bs, 1H), 3.71 (s, 3H), 2.80 (d, 2H), 0.90 (s, 9H), 0.05 (s, 6H).

Mass m/z (%): 380 (M$^+$ −84, 13), 323 (24), 231 (34), 199 (8), 159 (100), 85 (100), 57 (33).

REFERENCE EXAMPLE 13

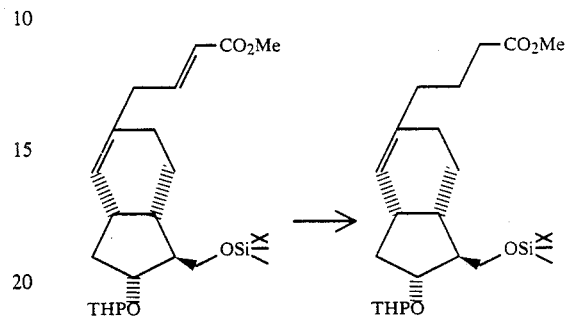

Under an argon atmosphere, cuprous bromide (1 g, 7 mmol) was suspended in THF (3ml). Then, vitride (70% toluene solution, 1.97 ml, 14 mmol) was dropwise added thereto at −20° C. The mixture was stirred at 30 minutes. Then, 2-butanol (1.4 ml, 15.8 mmol) and a THF solution (8 ml) of 3-(3-methoxycarbonyl-2-propenyl)-7-exo-t-butyldimethylsiloxymethyl-8-endo-tetrahydropyranyloxybicyclo[4,3,0]nona-2-ene (201 mg, 0.43 mmol) were added thereto at −78° C. The mixture was stirred at −20° C. for one hour and 30 minutes. Water and a saturated ammonium chloride aqueous solution were added to the reaction solution, and the mixture was diluted with ethyl ether. The mixture was stirred at room temperature until the water layer became blue. Then, the mixture was extracted with ethyl ether. The organic layer was washed with a saturated sodium chloride aqueous solution, and dried over anhydrous magnesium sulfate. The solvent was distilled off, and the residue was purified by silica gel column chromatography (ethyl ether:n-hexane=1:5) to obtain 3-(3-methoxycarbonylpropyl)-7-exo-t-butyldimethylsilyloxymethyl-8-endo-tetrahydropyranylox-ybicyclo-[4,3,0]nona-2-ene (200 mg, 100%).

IR (neat): 2900, 2830, 1735, 1455, 1425, 1225, 1195, 830, 775 cm$^{-1}$.

NMR (CDCl$_3$) δ: 5.30 (bs, 1H), 4.62 (bs, 1H), 3.56 (s, 3H), 0.90 (s, 9H), 0.05 (s, 6H).

Mass m/z (%): 466 (M$^+$, trace), 382 (2), 325 (7), 233 (13), 201 (12), 159 (34), 85 (100), 28 (23).

REFERENCE EXAMPLE 14

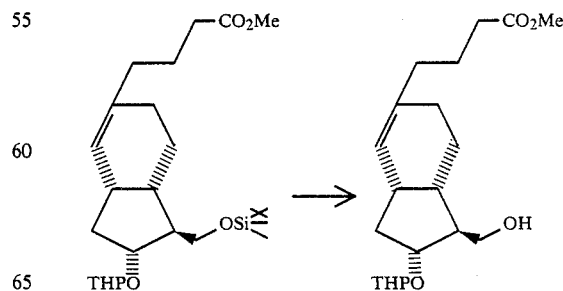

Under an argon atmosphere, 3-(methoxycarbonylpropyl)-7-exo-t-butyldimethylsilyloxymethyl-8-endotetrahydropyranyloxybicyclo[4,3,0]nona-2-ene (200 mg, 0.43 mmol) was dissolved in THF (2.5 ml). Then, tetra-n-butylammonium fluoride (1M THF solution, 0.86 ml, 0.86 mmol) was added thereto, and the mixture was stirred at room temperature for one day and night. After an addition of a saturated sodium chloride aqueous solution, the mixture was extracted with ethyl ether, and dried over anhydrous magnesium sulfate. Then, the solvent was distilled off. The residue was purified by silica gel column chromatography (ethyl ether:n-hexane=3:1) to obtain 3-(3-methoxycarbonylpropyl)-7-exo-hydroxymethyl-8-endo-tetrahydropyranyloxybicyclo[3,4,0]nona-2-ene (154 mg, 100%).

IR (neat): 3500, 2950, 2870, 1740, 1440, 1200 cm$^{-1}$.

NMR (CDCl$_3$) δ: 5.32 (bs, 1H), 4.62 (bs, 1H), 3.65 (s, 3H).

Mass m/z (%): 352 (M$^+$, trace), 268 (7), 219 (11), 131 (9), 85 (100). 41 (16).

REFERENCE EXAMPLE 15

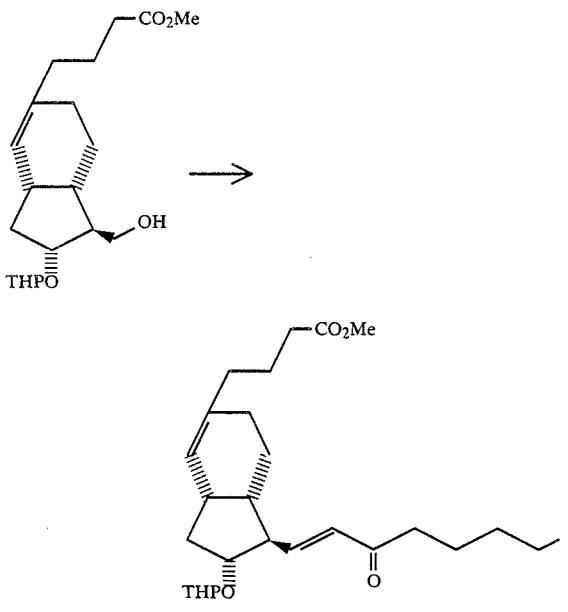

Under an argon atmosphere, 3-(3-methoxycarbonylpropyl)-7-exo-hydroxymethyl-8-endo-tetrahydropyranyloxybicyclo[4,3,0]nona-2-ene (60 mg, 0.17 mmol) was dissolved in dimethyl sulfoxide (2 ml). Then, triethylamine (0.11 ml, 1.02 mmol) and a dimethyl sulfoxide solution (2 ml) of a sulfur trioxide-pyridine complex (162 mg, 1.02 mmol), was added thereto, and the mixture was stirred at room temperature for one hour. After an addition of ice water, the mixture was extracted with ethyl acetate, washed with water and a saturated sodium chloride aqueous solution, and dried over anhydrous magnesium sulfate. Then, the solvent was distilled off to obtain 3-(3-methoxycarbonylpropyl)-7-exo-formyl-8-endo-tetrahydropyranyloxybicyclo[4,3,0]nona-2-ene (57 mg, 96%).

On the other hand, sodium hydride (oily 60%, 16 mg, 0.4 mmol) was washed with pentane under an argon atmosphere and suspended in THF (2 ml). Then, a THF solution (10 ml) of dimethyl(2-oxoheptyl)phosphonate (118 mg, 0.48 mmol) was added thereto, and the mixture was stirred at room temperature for 40 minutes. Then, a THF solution (3 ml) of 3-(3-methoxycarbonylpropyl)-7-exo-formyl-8-endo-tetrahydropyranyloxybicyclo[4,3,0-]nona-2-ene (57 mg) was added thereto, and the mixture was stirred at room temperature for one hour. After an addition of a saturated ammonium chloride aqueous solution, the mixture was extracted with ethyl ether. The ethyl ether layer was washed with a saturated sodium chloride aqueous aqueous solution, and dried over anhydrous magnesium sulfate. Then, the solvent was distilled off, and the residue thus obtained was purified to obtain 3-(3-methoxycarbonylpropyl)-7-exo-(3-oxo-trans-1-octenyl)-8-endo-tetrahydropyranyloxybicyclo[4,3,0]nona-2-ene (62 mg, 84%).

IR (neat): 2930, 2860, 1740, 1690, 1670, 1620, 1430, 1200, 1025, 865, 730 cm$^{-1}$.

NMR (CDCl$_3$) δ: 6.80 (m, 1H), 6.16 (dd, J=16.7 Hz, 1H), 5.33 (bs, 1H), 4.60 (m, 1H), 3.65 (s, 3H), 0.90 (t, 3H).

Mass m/z (%): 3.44 (13), 318 (8), 248 (7), 166 (36), 85 (100), 57 (21).

REFERENCE EXAMPLE 16

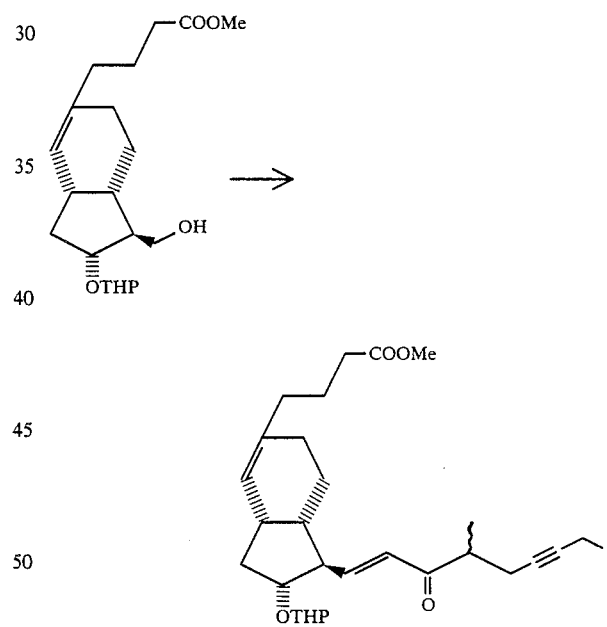

In the same manner as in Reference Example 14, 3-(3-methoxycarbonylpropyl)-7-exo-(3-oxo-4,8-dimethyl-1-trans-octen-6-ynyl)-8-endo-tetrahydropyranyloxybicyclo[4,3,0]nona-2-ene (84%) was prepared by the reaction with dimethyl(2-oxo-3,7-dimethyl-5-heptynyl)phosphonate. The spectrum data are as follows.

IR (neat): 2950, 2900, 1740, 1700, 1675, 1630, 1440, 1210, 1040 cm$^{-1}$.

NMR (CDCl$_3$) δ: 6.63 (m, 1H), 6.23 (dd, J=16.7, 4 Hz, 1H), 5.30 (bs, 1H), 4.56 (m, 1H), 3.63 (s, 3H), 1.23–100 (m, 6H).

SYNTHESIS EXAMPLE 1

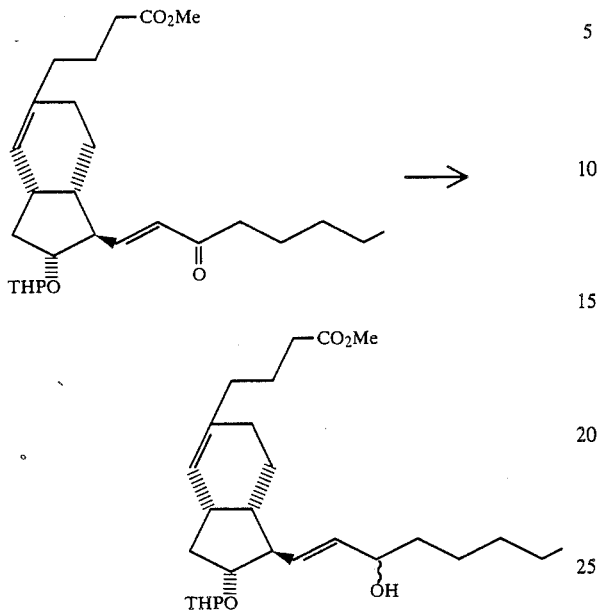

Under an argon atmosphere, 3-(3-methoxycarbonylpropyl)-7-exo-3-oxo-trans-1-octenyl)-8-endo-tetrahydroxybicyclo[4,3,0]nona-2-ene (46 mg, 0.14 mmol) was dissolved in methanol (3 ml). Then, the solution was cooled to $-25°$ C. and an excess amount of sodium borohydride was added thereto. The mixture was stirred at $-25°$ C. for 20 minutes, and an excess amount of acetone was added thereto. The mixture was returned to room temperature, and a saturated ammonium chloride aqueous solution was added thereto. Methanol and acetone were distilled off under reduced pressure. The residural aqueous layer was extracted with ethyl acetate, and the extract was dried over anhydrous magnesium sulfate. Then, the solvent was distilled off to obtain 3-(3-methoxycarbonylpropyl)-7-exo-(3-hydroxy-trans-1-octentyl)-7-endo-tetrahydropyranyloxybicyclo[4,3,0]nona-2-ene (47 mg, 100%).

IR (neat): 3450, 2930, 2860, 1740, 1200, 1030, 910, 730 cm$^{-1}$.

NMR (CDCl$_3$) δ: 5.60 (m, 2H), 5.30 (bs, 1H), 4.66 (bs, 1H), 3.33 (s, 3H), 0.88 (t, 3H).

Mass m/z (%): 346 (7), 302 (22), 279 (3), 149 (21), 85 (100), 57 (21).

SYNTHESIS EXAMPLE 2

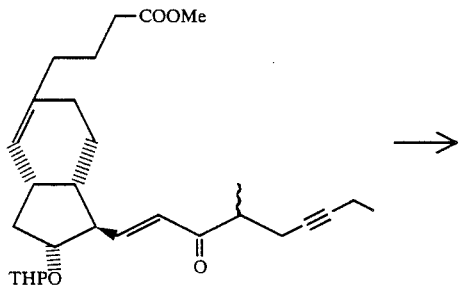

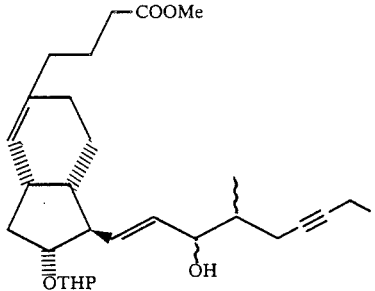

In the same manner as in Reference Example 16, 3-(3-methoxycarbonylpropyl)-7-exo-(3-hydroxy-4,8-dimethyl-1-trans-octen-6-ynyl)-8-endo-tetrahydropyranyloxybicyclo[4,3,0]nona-2-ene (78.1%) was prepared. The spectrum data are as shown below.

IR (neat): 3400, 2950, 2900, 1750, 1200, 1020 cm$^{-1}$.

NMR (CDCl$_3$) δ: 5.60 (m, 2H), 5.33 (bs, 1H), 4.63 (bs, 1H), 3.33 (s, 3H), 1.33–0.96 (m, 6H).

SYNTHESIS EXAMPLE 3

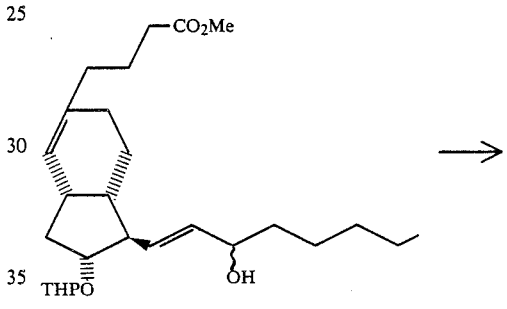

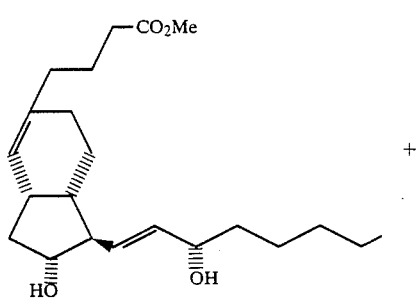

+

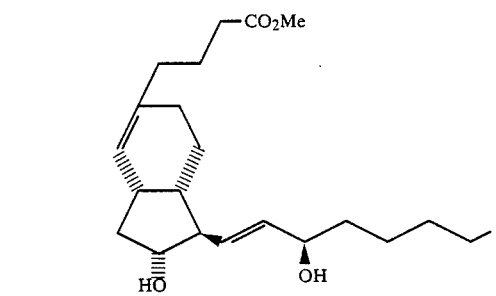

3-(3-methoxycarbonylpropyl)-7-exo-(3-hydroxy-trans-1-octenyl)-7-endo-tetrahydropyranyloxybicyclo[4,3,0]nona-2-ene (45 mg, 0.1 mmol) was dissolved in a mixture of acetic acid:THF:water (0,7 ml) (volume ratio of 3:1:1), and the solution was stirred at 50° C. for 2 hours. After cooling, the solution was diluted with ethyl acetate and nutralized with a saturated sodium bicarbonate aqueous solution. The ethyl acetate layer was washed with a saturated sodium chloride aqueous solution, and dried over anhydrous magnesium sulfate. The residue obtained by distilling off the solvent, was purified by silica gel column chromatography (ethyl ether:n-hexane=5:1) to obtain 3-(3-methoxycarbonyl-propyl)-7-exo-(3β-hydroxy-trans-1-octenyl)-8-endo-hydroxybicyclo[4,3,0]nona-2-ene (9 mg, 25%) as a high polarity fraction and 3-(3-methoxycarbonylpropyl)-7-exo-(3β-hydroxy-trans-1-octenyl)-8-endo-hydroxybicyclo[4,3,0]nona-2-ene (12 mg, 25% as a low polarity fraction, respectively.

The spectrum data of the α-epimer are as shown below. The spectrum of the β-epimer was substantially the same.

IR (neat): 3410, 2980, 2940, 1742 cm$^{-1}$.

NMR (CDCl$_3$) δ: 5.57 (m, 2H), 5.36 (bs, 1H), 3.69 (s, 3H), 0.89 (t, 3H).

Mass m/z (%): 346 (M$^+$ −H$_2$O, 13), 302 (36), 149, (100), 79 (12), 43 (86).

SYNTHESIS EXAMPLE 4

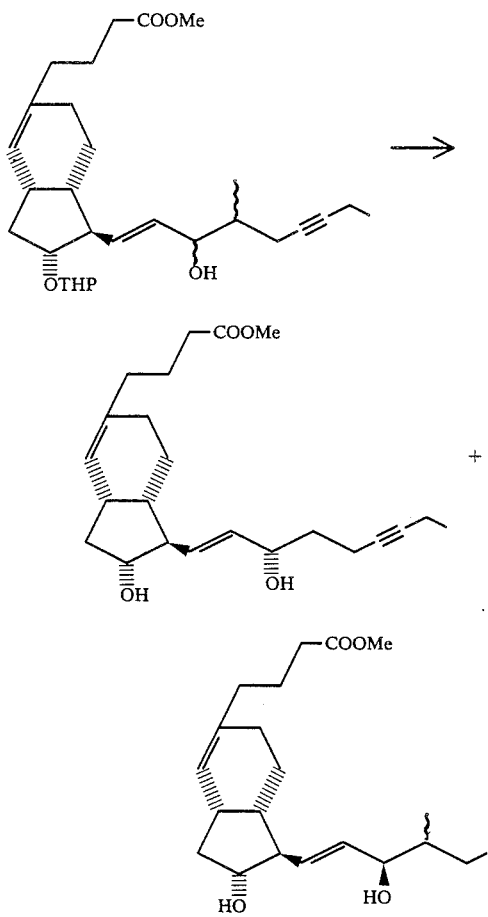

In the same manner as in Reference Example 18, 3-(3-methoxycarbonylpropyl)-7-exo-(3α-hydroxy-4,8-dimethyl-1-trans-octenyl-6-ynyl)-8-endo-hydroxybicyclo[4,3,0]nona-2-ene (44%) and its β-epimer (31%) were prepared. The spectrum data of the α-epimer are as shown below. The spectrum of the β-epimer was substantially the same.

IR (neat): 3400, 2930, 2870, 1740 cm$^{-1}$.

NMR (CDCl$_3$) δ: 5.63 (m, 2H), 5.30 (bs, 1H), 3.30 (s, 3H), 1.23–0.88 (m, 6H).

SYNTHESIS EXAMPLE 5

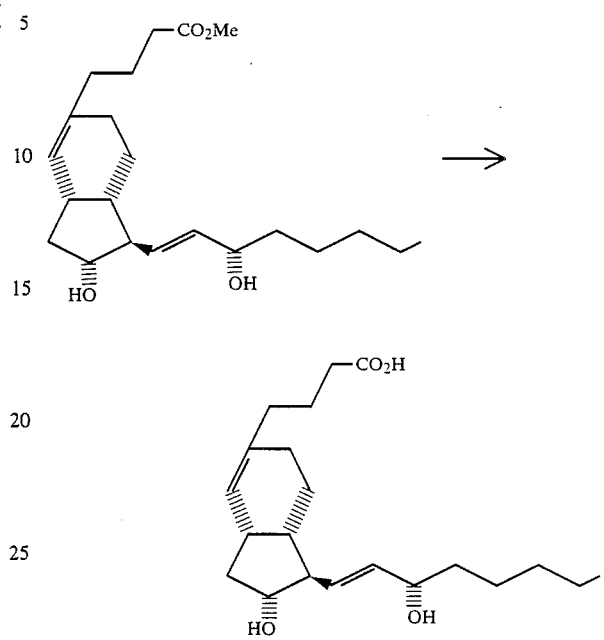

Under an argon atmosphere, 3-(3-methoxycarbonylpropyl)-7-exo-(3α-hydroxy-trans-1-octenyl)-8-endo-hydroxybicyclo[4,3,0]nona-2-ene (9 mg, 0.025 mmol) was dissolved in methanol (0.2 ml). Then, a 10% sodium hydroxide aqueous solution (0.2 ml) was added thereto at 0° C., and the mixture was stirred for over night. After nutralizing the mixture was a 1N hydrochloric acid aqueous solution at 0° C., methanol was distilled off, and the residual aqueous layer was adjusted to pH4 with a 1N hydrochloric acid aqueous solution. Then, it was extracted with ethyl acetate, washed with a saturated sodium chloride aqueous solution and dried over anhydrous magnesium sulfate. Then, the solvent was distilled off to obtain 3-(3-carboxypropyl)-7-exo-(3α-hydroxy-trans-1-octenyl)-8-endo-hydroxybicyclo[4,3,0]nona-2-ene (8.9 mg, 100%).

IR (neat): 3375, 2970, 2860, 1720, 1125 cm$^{-1}$.

NMR (CDCl$_3$) δ: 5.60 (m, 2H), 5.35 (bs, 1H), 0.90 (t, 3H).

Mass m/z (%): 332 (M$^+$ −H$_2$O, 10), 288 (18), 218 (10), 208 (13), 138 (50), 91 (53), 43 (100).

In the same manner, 15β-epimer was also hydrolyzed to obtain 3-(3-carboxypropyl)-7-exo-(3β-hydroxy-trans-1-octenyl)-8-endo-hydroxybicyclo[4,3,0]nona-2-ene. The spectrum data (IR, NMR, Mass) were the same as the data of 3-(3-(carboxypropyl)-7-exo-(3α-hydroxy-trans-1-octenyl)-8-endo-hydroxybicyclo[4,3,0]nona-2-ene.

SYNTHESIS EXAMPLE 6

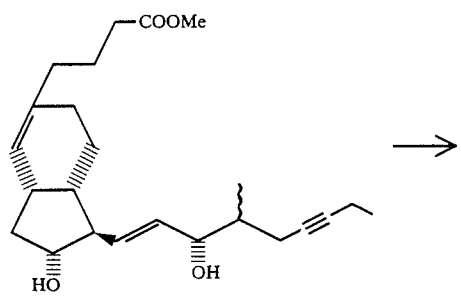

In the same manner as in Reference Example 20, 3-(3-carboxypropyl)-8-exo-(3α-hydroxy-4,8-dimethyl-1-trans-octen-6-ynyl)-8-endo-hydroxybicyclo[4,3,0-]nona-2-ene 97%) and its β-epimer (98%) were prepared. The sepctrum data of the α-epimer are as shown below. The spectrum of the β-epimer was substantially the same.

IR (neat): 3370, 2940, 2850, 1710, 1450 cm$^{-1}$.
NMR (CDCl$_3$) δ: 5.60 (m, 2H), 5.30 (bs, 1H), 1.30–0.88 (t, 6H).

REFERENCE EXAMPLE 17

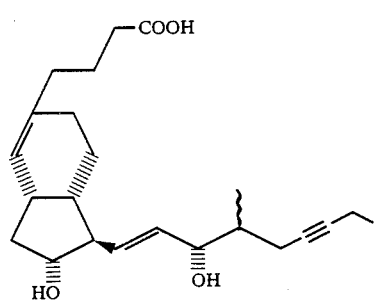

Under an argon atmosphere, 3-carboxypropyltriphenylphosphonium bromide (1.1 g, 2.5 mmol) was suspended in THF (10 ml). Then, a THF solution (10 m) of potassium t-butoxide (560 mg, 5 mmol) was added thereto, and the mixture was stirred at room temperature for 20 minutes. Then, a THF solution (5 ml) of 3-formyl-7-exo-t-butyl-dimethylsilyloxymethyl-8-endo-tetrahydropyranyloxybicyclo[4,3,0]nona-2-ene (200 mg, 0.5 mmol) was dropwise added thereto, and the mixture was stirred at room temperature for 30 minutes. After an addition of a saturated ammonium chloride aqueous solution, the reaction solution was adjusted to pH5–4 with a 10% hydrochloric acid aqueous solution, and extracted with ethyl acetate. The organic layer was dried over anhydrous magnesium sulfate, and the solvent was distilled off. Ethyl ether was added to the residue, and an ethyl ether solution of diazomethane was added thereto at 0° C. After confirming the disapearance of the spot of 3-(4-carboxy-1-butenyl)-7-exo-t-butyldimethylsilyloxymethyl-8-endo-tetrahydropyranyloxybicyclo[4,3,0]nona-2-ene by thin layer chromatography, a small amount of formic acid was added thereto, and the mixture was immadiately washed with a saturated sodium bicarbonate aqueous solution and a saturated sodium chloride aqueous solution. After drying the mixture over anhydrous magnesium sulfate, the solvent was distilled off, and the residue thus obtained was purified by silica gel column chromatography (ethyl ether:n-hexane=1:4) to obtain 3-(4-methoxy-carbonyl-2-butenyl)-7-exo-t-butyldimethylsilyloxymethyl-8-endo-tetrahydropyranyl-bicyclo[4,3,0]nona-2-ene (210 mg, 88%). The ratio of the (Z) isomer to the (E) isomer was 2:1.

IR (neat): 2950, 2860, 1740, 1430, 1255, 1200, 1030, 335 cm$^{-1}$.
NMR (CDCl$_3$) δ: 6.12 (d, J=16.5 Hz, ⅓H, trans), 5.96 (d, J=12 Hz, ⅔H, cis), 5.63 (bs, 1H), 5.30 (m, 1H), 4.65 (bs, 1H), 3.70 (s, 3H), 0.90 (s, 9H).
Mass m/z (%): 479 (M$^+$+1, trace), 337 (12), 245 (14), 213 (9), 159 (34), 85 (100), 57 (17).

REFERENCE EXAMPLE 18

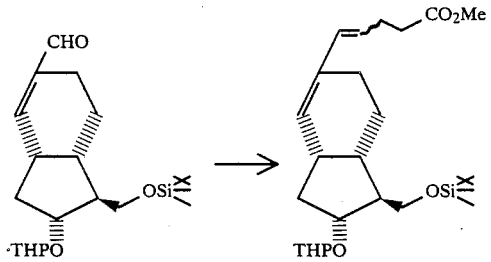

In the same manner as in Reference Example 14, 3-(4-methoxycarbonyl-1-butenyl)-7-exo-hydroxymethyl-8-endo-tetrahydropyanyloxy-cis-bicyclo[4,3,0]nona-2-ene (108 mg, 90%) was prepared from 3-(4-methoxycarbonyl-1-butenyl)-7-exo-t-butyldimethylsilyloxymethyl-8-endotetrahydropyranyloxy-cis-bicyclo[4,3,0]nona-2-ene (160 mg, 0.03 mmol).

IR (neat): 3490, 2950, 2880, 1740, 1435, 1200, 1020, 865 cm$^{-1}$.
NMR (CDCl$_3$) δ: 6.30 (d, J=16.5 Hz, ⅓H, trans), 5.83 (d, J=12 Hz, ⅔H, cis), 5.60 (bs, 1H), 5.30 (m, 1H), 4.68 (m, 1H), 3.70 (s, 3H).
Mass m/z (%): 364 (M$^+$ trace), 280 (15), 199 (5), 117 (11), 85 (100), 28 (29).

REFERENCE EXAMPLE 19

-continued

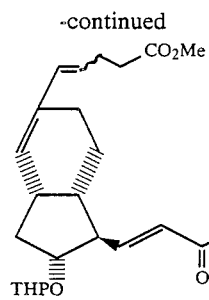

In the same manner as in Reference Example 15, 3-(4-methoxycarbonyl-1-butenyl-7-exo-3-oxo-1-trans-octenyl)-8-endo-tetrahydropyranyloxy-cis-bicyclo[4,3,0]nona-2-ene (112 mg, 84%) was prepared by the reaction with dimethyl(2-oxoheptyl)phosphonate.

IR (neat): 2940, 2880, 1740, 1700, 1675, 1625, 1430, 1200, 1030 cm$^{-1}$.

NMR (CDCl$_3$) δ: 6.81 (m, 1H), 6.22 (dd, J=16.5, 3 Hz, 1H), 6.08 (d, J=15 Hz, ⅓H trans), 5.82 (d, J=12 Hz, ⅔H cis), 5.56 (bs, 1H), 5.30 (m, 1H), 4.62 (m, 1H), 3.70 (s, 3H), 0.88 (t, 3H).

Mass m/z (%): 376 (8), 332 (12), 85 (100), 57 (18), 55 (13), 41 (2).

SYNTHESIS EXAMPLE 7

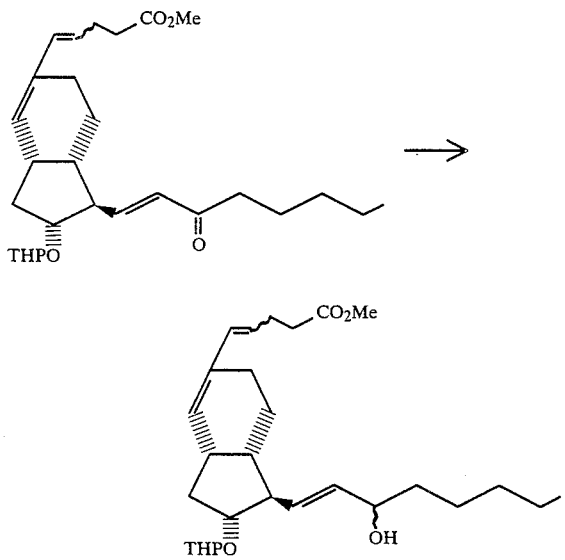

In the same manner as in Synthesis Example 1, 3-(4-methoxycarbonyl-1-butenyl)-7-exo-(3-hydroxy-1-trans-octenyl)-8-endo-tetrahydropyranyloxy-cis-bicyclo[4,3,0]nona-2-ene (112 mg, 100%) was prepared.

IR (neat): 3450, 2900, 2850, 1738, 1430, 1200, 1020 cm$^{-1}$.

NMR (CDCl$_3$) δ: 6.11 (d, J=16.5 Hz, ⅓H, trans), 5.82 (d, J=12 Hz, ⅔H, cis), 5.58 (m, 3H), 5.25 (m, 1H), 4.68 (bs, 1H), 3.70 (s, 3H), 0.88 (t, 3H).

Mass m/z (%): 442 (M$^+$—H$_2$O, trace), 358 (10), 314 (11), 234 (31), 150 (21), 85 (100), 41 (24).

SYNTHESIS EXAMPLE 8

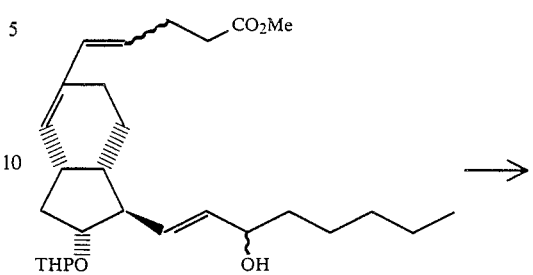

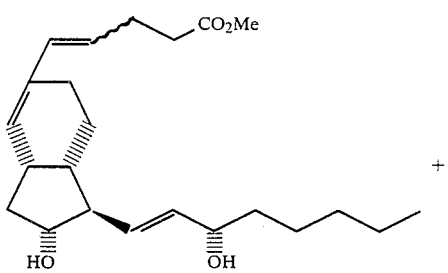

+

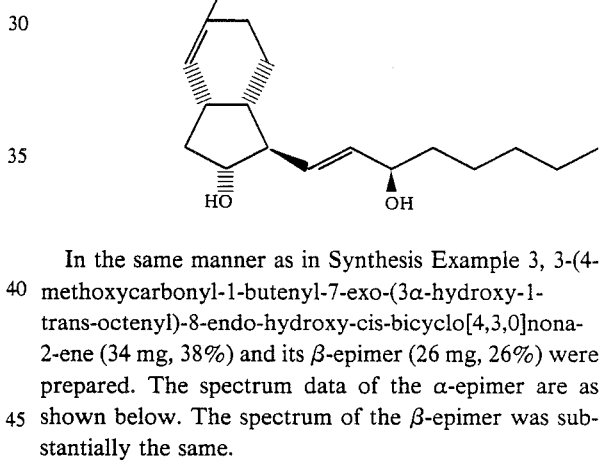

In the same manner as in Synthesis Example 3, 3-(4-methoxycarbonyl-1-butenyl-7-exo-(3α-hydroxy-1-trans-octenyl)-8-endo-hydroxy-cis-bicyclo[4,3,0]nona-2-ene (34 mg, 38%) and its β-epimer (26 mg, 26%) were prepared. The spectrum data of the α-epimer are as shown below. The spectrum of the β-epimer was substantially the same.

IR (neat): 3400, 2950, 2880, 1745, 1440, 740 cm$^{-1}$.

NMR (CDCl$_3$) δ: 6.06 (d, J=16 Hz, ⅓H, trans), 5.81 (d, J=12 Hz, ⅔H, cis), 5.53 (m, 3H), 5.25 (m, 1H), 3.70 (s, 3H), 0.86 (t, 3H).

Mass m/z (%): 353 (M$^+$—H$_2$O, 19), 314 (11), 244, (28), 227 (9), 117 (45) 91 (59), 43 (100).

SYNTHESIS EXAMPLE 9

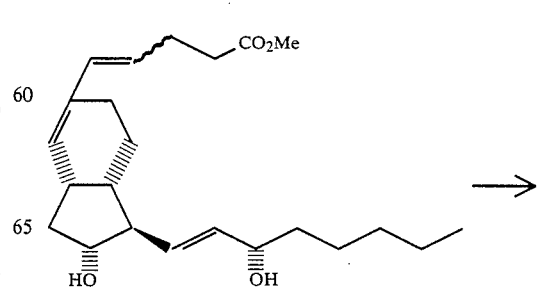

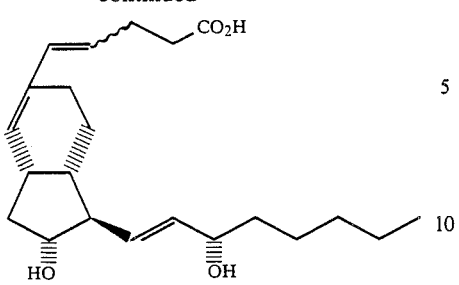

In the same manner as in Synthesis Example 5, 3-(4-carboxy-1-butenyl)-7-exo-(3α-hydroxy-1-trans-octenyl)-8-endo-hydroxy-cis-bicyclo[4,3,0]nona-2-ene (28 mg, 97%) and its β-epimer were prepared.

IR (neat): 3375, 2950, 2870, 1720, 1440, 1120, 965 cm$^{-1}$.

NMR (CDCl$_3$) δ: 6.10 (d, J=16 Hz, ⅓H, trans), 5.85 (d, J=12 Hz, ⅔H, cis), 5.63 (m, 3H), 5.40–5.13 (m, 3H), 0.90 (t, 3H).

Mass m/z (%): 344 (M$^+$−H$_2$O, 12), 300 (20), 230 (12), 220 (15), 150 (48), 91 (56), 43 (100).

REFERENCE EXAMPLE 20

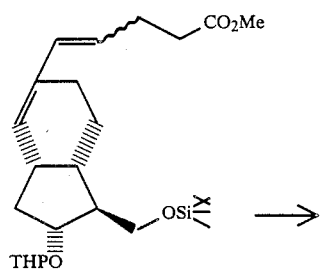

3-(4-methoxycarbonyl-1-butenyl)-7-exo-t-butyldimethylsilyloxymethyl-8-endo-tetrahydropyranyloxybicyclo[4,3,0]nona-2-ene (190 mg, 0.4 mmol) was dissolved in methanol (5 ml). Then, a methanol solution (5 ml) of 10% pallasium/carbon (60 mg) was added thereto, and the mixture was stirred under a hydrogen atmosphere at room temperature for one hour and 30 minutes. The catalyst was filtered off, and the solvent was distilled off from the filtrate. The residue was purified by silica gel column chromatography (ethyl ether:n-hexane=1:8) to obtain 3-(4-methoxycarbonylbutyl)-7-exo-t-butyldimethylsilyloxymethyl-8-tetrahydropyranyloxybicyclo[4,3,0]nona-2-ene (187 mg, 97%).

IR (neat): 2930, 2850, 1740, 1200, 835 cm$^{-1}$.

NMR (CDCl$_3$) δ: 5.35 (bs, 1H), 4.63 (bs, 1H), 3.66 (s, 3H), 0.90 (s, 9H).

Mass m/z (%): 339 (8), 247 (12), 159 (28), 85 (100), 75 (17).

REFERENCE EXAMPLE 21

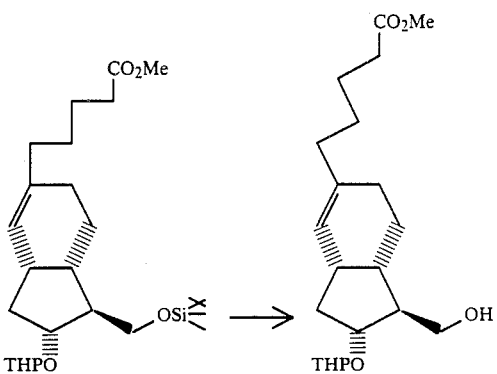

In the same manner as in Reference Example 14, 3-(4-methoxycarbonyl)-7-exo-hydroxymethyl-8-endo-tetra-hydropyranyloxy-cis-bicyclo[4,3,0]nona-2-ene (62 mg, 89%) was prepared from 3-(4-methoxycarbonylbutyl)-7-exo-t-butyl-dimethylsilyloxymethyl-8-endo-tetrahydropyranyloxy-cis-bicyclo[4,3,0]nona-2-ene (93 mg, 0.19 mmol).

IR (neat): 3450, 2930, 2850, 1740, 1020 cm$^{-1}$.

NMR (CDCl$_3$) δ: 5.35 (bs, 1H), 4.65 (bs, 1H), 3.66 (s, 3H).

Mass m/z (%): 3.66 (M$^+$, trace), 282 (5), 85 (100), 65 (11), 57 (10), 41 (11).

REFERENCE EXAMPLE 22

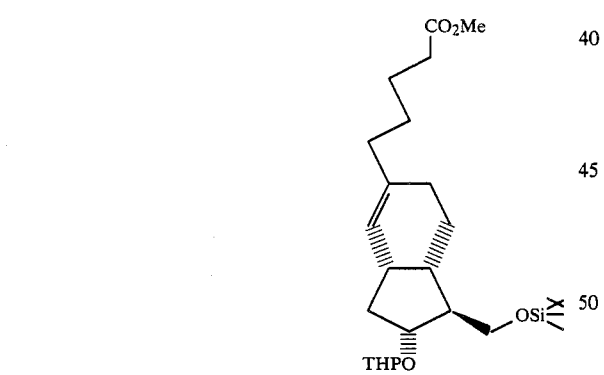

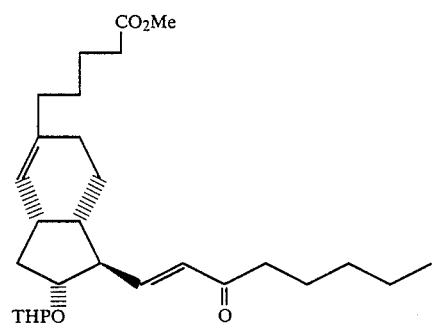

In the same manner as in Reference Example 15, 3-(4-methoxycarbonylbutyl)-7-exo-(3-oxo-1-trans-octenyl-8-endo-tetrahydropyranyloxy-cis-bicyclo[4,3,0]nona-2-ene (51 mg, 80%) was obtained by the reaction with dimethyl(2-oxoheptyl)phosphonate.

IR (neat): 2930, 2880, 1740, 1700, 1675, 1625, 1200, 1030 cm$^{-1}$.

NMR (CDCl$_3$) δ: 6.83 (m, 1H), 6.20 (dd, J=15, 3.5 Hz, 1H), 5.33 (bs, 1H), 4.65 (m, 1H), 3.70 (s, 3H).

Mass m/z (%): 376 (10), 312 (13), 85 (100), 67 (16), 57 (20), 43 (21), 41 (20).

SYNTHESIS EXAMPLE 10

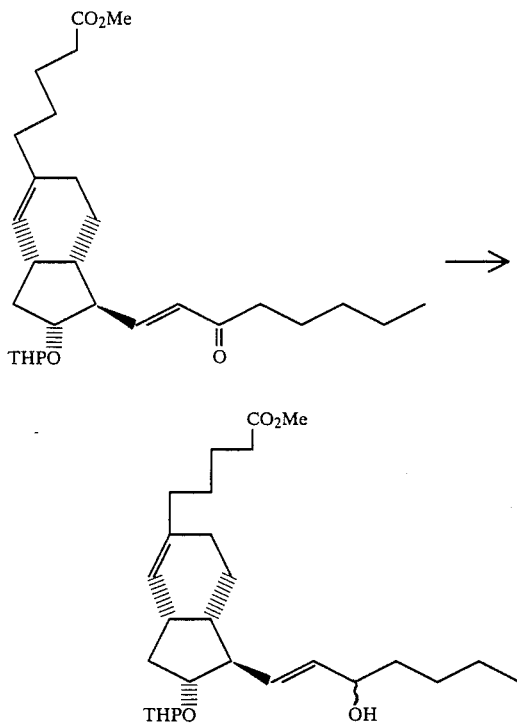

In the same manner as in Synthesis Example 1, 3-(4-methoxycarbonylbutyl)-7-exo-(3-hydroxy-1-trans-octenyl)-8-endo-tetrahydropyranyloxy-cis-bicyclo[4,3,0]nona-2-ene (118 mg, 98%) was prepared.

IR (neat): 3450, 2930, 2850, 1740, 1020 cm$^{-1}$.

NMR (CDCl$_3$) δ: 5.58 (m, 2H) 5.31 (bs, 1H), 4.67 (bs, 1H), 3.66 (s, 3H), 0.86 (t, 3H).

Mass m/z (%): 444 (M$^+$ —H$_2$O, trace), 316 (13), 85 (100), 67 (12), 57 (18), 55 (10), 43 (17), 41 (20).

SYNTHESIS EXAMPLE 11

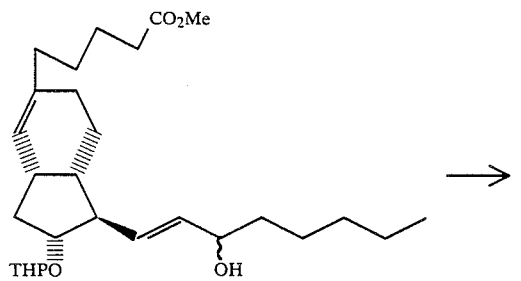

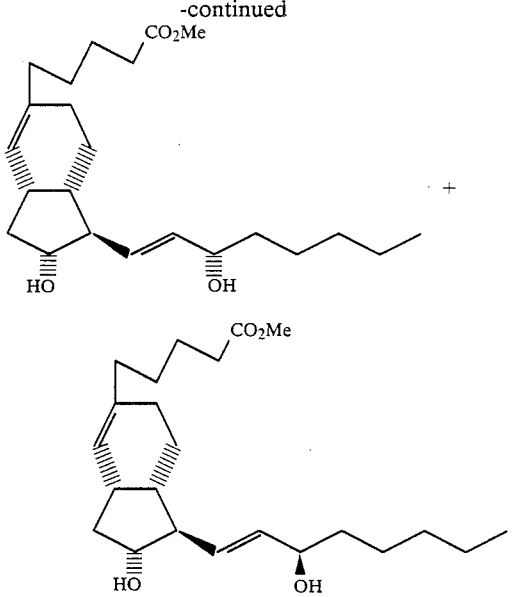

In the same manner as in Synthesis Example 3, 3-(4-methoxycarbonylbutyl)-7-exo-(3α-hydroxy-1-trans-octenyl)-8-endo-hydroxy-cis-bicyclo[4,3,0]nona-2-ene (42 mg, 44%) and its β-epimer (29 mg, 31%) were prepared. The spectrum data of the α-epimer are as shown below. The spectrum of the β-epimer was substantially the same.

IR (neat): 3400, 2940, 2870, 1740 cm$^{-1}$.

NMR (CDCl$_3$): 5.56 (m, 2H), 5.33 (bs, 1H), 4.10 (m, 1H), 3.68 (s, 3H), 0.88 (t, 3H).

Mass m/z (%): 358 (M$^+$ —H$_2$O, 21), 342 (18), 329 (9), 316 (75), 289 (15), 261 (11), 246 (32), 199 (17), 193 (20), 179 (27).

SYNTHESIS EXAMPLE 12

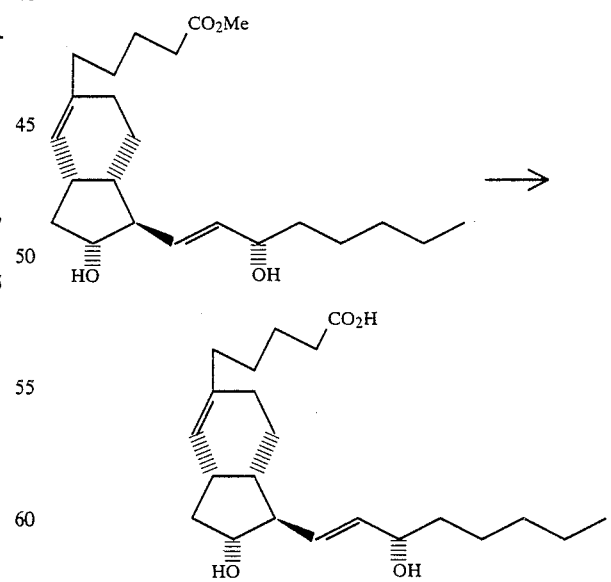

In the same manner as in Synthesis Example 5, 3-(4-carboxybutyl)-7-exo-(3α-hydroxy-1-trans-octenyl)-8-endo-hydroxy-cis-bicyclo[4,3,0]nona-2-ene (35 mg, 96%) and its β-epimer were prepared.

IR (neat): 3350, 2950, 2850, 1720, 1450 cm$^{-1}$.

NMR (CDCl₃): 5.60 (m, 2H), 5.33 (bs, 1H), 3.73 (s, 3H), 0.88 (t, 3H).

Mass m/z (%): 346 (M⁺ −H₂O, 10), 302 (17), 232 (14), 91 (50), 43 (100).

REFERENCE EXAMPLE 23

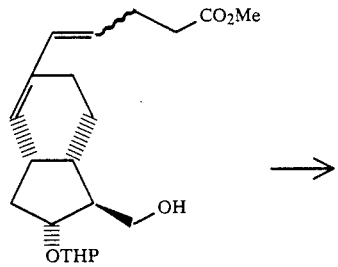

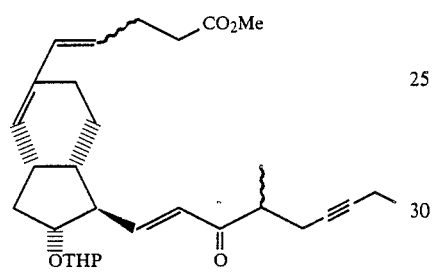

In the same manner as in Reference Example 15, 3-(4-methoxycarbonyl-1-butenyl)-7-exo-(3-oxo-4,8-dimethyl-1-trans-octen-6-ynyl)-8-endo-tetrahydropyranyloxy-cis-bicyclo[4,3,0]nona-2-ene (93 mg, 61.6%) was prepared by the reaction with dimethyl(2-oxo-3,7-dimethyl-5-heptyl)phosphonate.

IRνmax (neat): 2950, 1740, 1700, 1670, 1625, 1435, 1360, 1320, 1260, 1200, 1160, 1130, 1080, 1030, 975, 915, 870, 815 cm⁻¹.

NMR (CDCl₃) δ: 1.00–1.30 (6H, m), 3.72 (3H, s), 4.65 (1H, m), 5.56 (1H, br-s), 6.30 (1H, d.d., J=15 Hz, 3 Hz), 6.83 (1H, m).

MASS (m/z) (%): 85 (100), 190 (30), 285 (16), 398 (6, M⁺ −84).

SYNTHESIS EXAMPLE 13

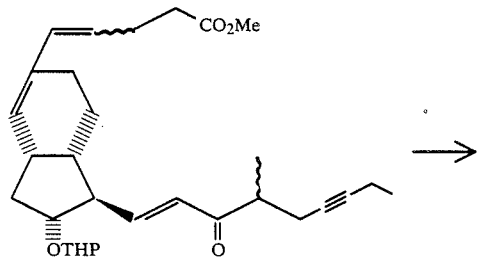

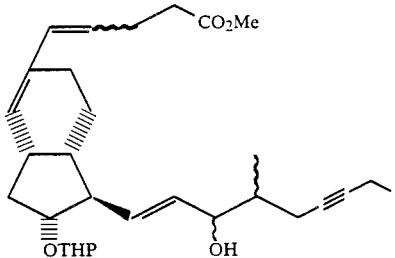

In the same manner as in Synthesis Example 1, 3-(4-methoxycarbonyl-1-butenyl)-7-exo-(3-hydroxy-4,8-dimethyl-1-trans-octen-6-ynyl)-8-endo-tetrahydropyranyloxy-cis-bicyclo[4,3,0]nona-2-ene (83 mg, 93.1%) was prepared.

IRνmax (neat): 3500, 2950, 1750, 1440, 1360, 1330, 1260, 1160, 1140, 1080, 1035, 975, 920, 870, 820 cm⁻¹.

NMR (CDCl₃) δ: 0.94–1.30 (6H, m), 3.70 (3H, s), 4.70 (1H, br-s), 5.25 (1H m), 5.63 (3H, m).

MASS (m/z) (%): 85 (100), 107 (100), 234 (100), 338 (46), 382 (24), 400 (4, M⁺ −84).

SYNTHESIS EXAMPLE 14

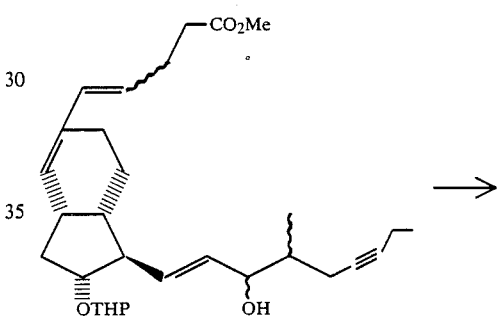

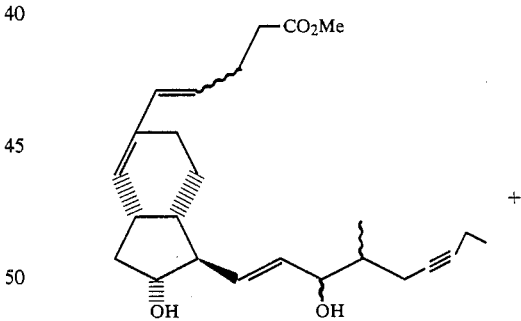

+

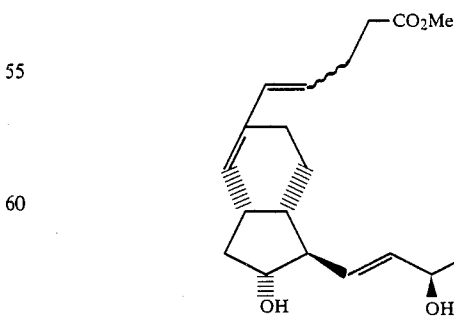

In the same manner as in Synthesis Example 3, 3-(4-methoxycarbonyl-1-butenyl)-7-exo-(3α-hydroxy-4,8-dimethyl-1-trans-octen-6-ynyl)-8-endo-hydroxy-xisbicyclo[4,3,0]nona-2-ene (30.9 mg, 50.4%) and its β-epimer (17.5 mg, 28.6%) were prepared IR νmax (neat): 3420, 2950, 1745, 1435, 1360, 1325, 1260, 1200, 1165, 1080, 1020, 970, 915, 865, 735 cm$^{-1}$.

NMR (CDCl$_3$) δ: 0.80–1.30 (6H, m), 3.71 (3H, s), 5.60 (4H, m), 6.10 (1H, d, J=16 Hz).

MASS (m/z) (%): 107 (100), 117 (42), 131 (33), 145 (26), 234 (32), 382 (4), 400 (1, M+).

SYNTHESIS EXAMPLE 15

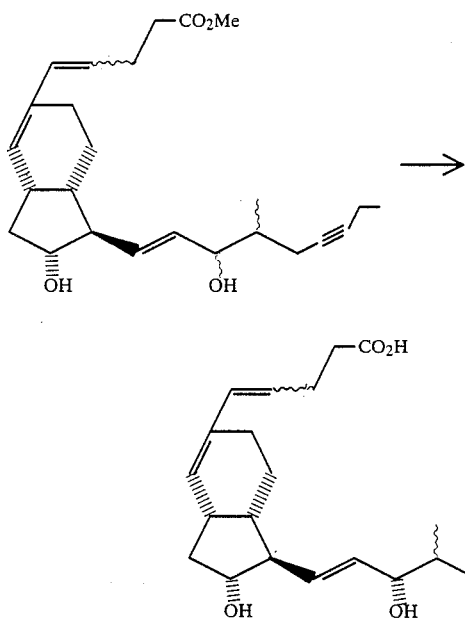

In the same manner as in Synthesis Example 5, 3-(4-carboxy-1-butenyl)-7-exo-(3α-hydroxy-4,8-dimethyl-1-trans-octen-6-ynyl)-8-endo-hydroxy-cis-bicyclo[4,3,0-]nona-2-ene (26.4 mg, 88.2%) and its β-epimer were prepared.

IR νmax (neat): 3300, 2950, 1715, 1430, 1380, 1320, 1260, 1200, 1160, 1120, 1075, 1010, 970, 920, 865 cm$^-$.

NMR (CDCl$_3$) δ: 0.85–1.35 (6H, m), 5.13–5.75 (4H, m), 5.85 (⅔H, d, J=11 Hz), 6.10 (⅓H, d, J=16 Hz).

MASS (m/z) (%): 107 (100), 117 (41), 131 (29), 145 (26), 174 (28), 273 (11), 324 (10), 368 (4, M+−18).

REFERENCE EXAMPLE 24

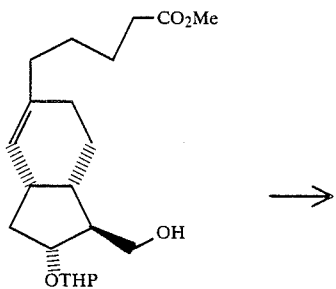

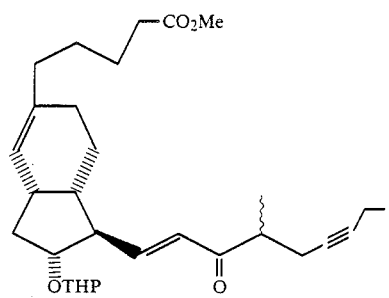

In the same manner as in Reference Example 15, 3-(4-methoxycarbonylbutyl)-7-exo-(3-oxo-4,8-dimethyl-1-trans-octen-6-ynyl)-8-endo-tetrahydropyranyloxy-cis-bicyclo[4,3,0]nona-2-ene (57 mg, 68.4%) was prepared by the reaction with dimethyl(2-oxo-3,7-dimethyl-5-heptyl)phosphonate.

IR νmax (neat): 2950, 1740, 1700, 1675, 1625, 1455, 1440, 1360, 1325, 1200, 1140, 1080, 1035, 980, 915, 870, 820 cm$^{-1}$.

NMR (CDCl$_3$) δ: 1.00–1.30 (6H, m), 3.70 (3H, s), 4.63 (1H, m), 5.34 (1H, br-s), 6.28 (1H, dd, J=16 Hz, 3 Hz), 6.83 (1H, m).

MASS (m/z) (%): 85 (100), 91 (49), 105 (49), 190 (52), 287 (29), 382 (20), 400 (6, M+−84).

SYNTHESIS EXAMPLE 16

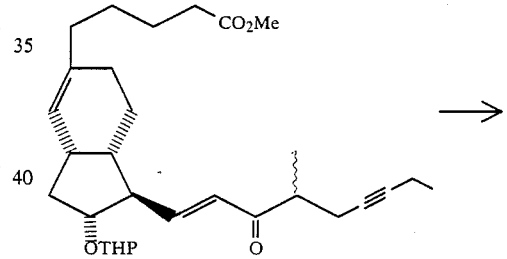

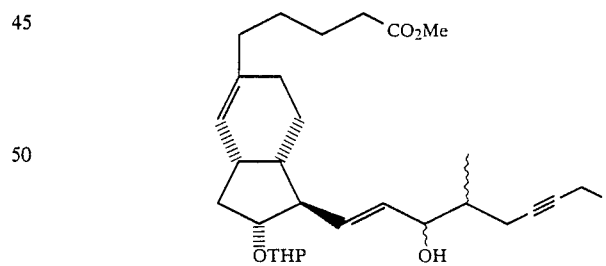

In the same manner as in Synthesis Example 1, 3-(4-methoxycarbonylbutyl)-7-exo-(3-hydroxy-4,8-dimethyl-1-trans-octen-6-ynyl)-8-endo-tetrahydropyranyloxy-cis-bicyclo[4,3,0]nona-2-ene (48 mg, 85.4%) was prepared.

IR νmax (neat): 3500, 2950, 1745, 1440, 1355, 1325, 1260, 1205, 1140, 1080, 1030, 975, 915, 870, 815, 735 cm$^{-1}$.

NMR (CDCl$_3$) δ: 0.90–1.30 (6H, m), 3.70 (3H, s), 4.70 (1H, br-s), 5.33 (1H, br-s), 5.65 (2H, m).

MASS (m/z) (%): 85 (100), 107 (20), 340 (19), 384 (4, M+−102).

SYNTHESIS EXAMPLE 17

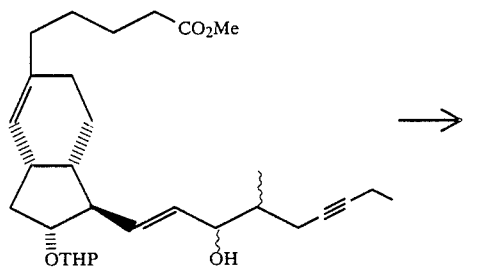

→

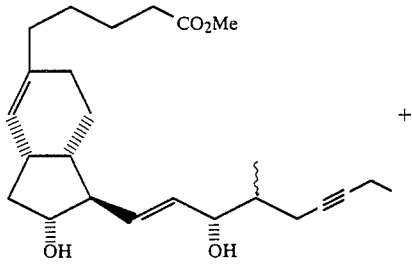

+

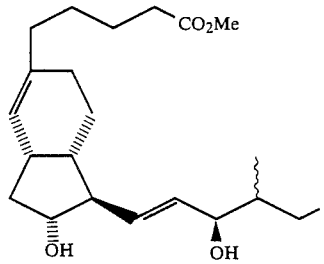

In the same manner as in Synthesis Example 3, 3-(4-methoxycarbonylbutyl)-7-exo-(3α-hydroxy-4,8-dimethyl-1-trans-octen-6-ynyl)-8-endo-hydroxy-cis-bicyclo[4,3,0]nona-2-ene (20 mg, 51.4%) and its β-epimer (13 mg, 33.4%) were prepared.

IR νmax (neat: 3450, 2940, 1740, 1435, 1320, 1200, 1170, 1080, 1015, 970, 920, 840, 735 cm$^{-1}$.

NMR (CDCl$_3$) δ: Z 0.80–1.30 (6H, m), 3.70 (3H, s), 5.36 (1H, br-s), 5.63 (2H, m).

MASS (m/z) (%): 107 (100), 145 (26), 174 (26), 340 (18), 384 (1, M$^+$ −18).

SYNTHESIS EXAMPLE 18

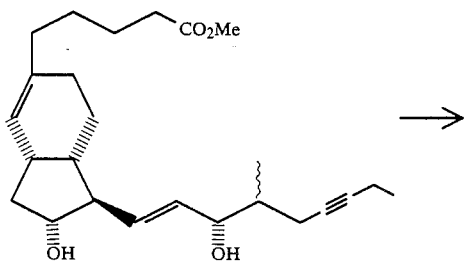

→

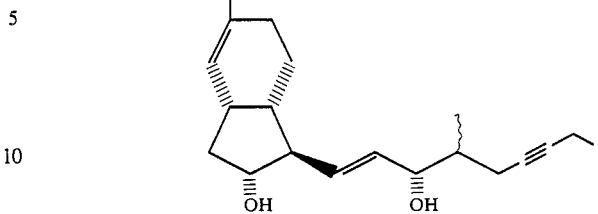

In the same manner as in Synthesis Example 5, 3-(4-carboxybutyl)-7-exo-(3α-hydroxy-4,8-dimethyl-1-trans-octen-6-ynyl)-8-endo-cis-bicyclo[4,3,0]nona-2-ene (17.9 mg, 94%) and its β-epimer were prepared.

IR νmax (neat): 3400, 2950, 1715, 1440; 1380, 1325, 1265, 1080, 1020, 975, 805 cm$^{-1}$.

NMR (CDCl$_3$) δ: 0.85–1.35 (6H, m), 5.35 (1H, br-s), 560 (2H, m).

MASS (m/z) (%): 107 (100), 117 (29), 119 (26), 131 (27), 145 (28), 174 (24), 326 (14), 370 (3, M$^+$ −18).

REFERENCE EXAMPLE 25

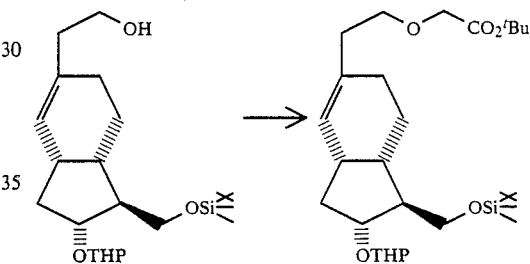

Under an argon atmosphere, 3-(2-hydroxyethyl)-7-exo-t-butyldimethylsilyloxymehtyl-8-endo-tetrahydropyranyloxy-cis-bicyclo[4,3,0]nona-2-ene (295 mg, 0.718 mmol) was dissolved in methylene chloride (3 ml). Then, tert-butylbromo acetate (3.6 ml, 22.2 mmol), a 50% sodium hydroxide aqueous solution (1.4 ml) and tetrabutylammonium hydrogensulfate (71 mg) were added thereto at room temperature, and the mixture was stirred at the same temperature for 3 days. Then, ice water (10 ml) was added, and the mixture was extracted with ethyl ether. The extract was washed with a saturated sodium chlorid aqueous solution and dried over anhydrous magnesium sulfate. Then, the solvent was distilled off to obtain a colorless oily substance.

The purification was conducted by silica gel column chromatography to obtain 3-(3-oxa-4-t-butoxycarbonyl-butyl)-7-exo-t-butyldimethylsilyloxymethyl-8-endo-tetrahydropyranyloxy-cis-bicyclo[4,3,0]nona-2-ene as a colorless oily substance (346 mg, 91.8%).

IR νmax (neat): 2950, 1750, 1460, 1390, 1370, 1300m 1255, 1215, 1130, 1080, 1030, 940, 910, 840, 780 cm$^{-1}$.

NMR (CDCL$_3$) δ: 0.05 (6H, s), 0.90 (9 H, s), 1.50 (9H, s), 1.30–2.06 (13H, m), 2.15–2.45 (4H, m), 3.40–3.78 (7H, m)m Lb 4.12 (2H, s), 4.65 (1H, br-s), 5.47 (1H, br-s).

MASS (m/z) (%): 85 (100), 159 (100), 251 (15), 384 (12), 440 (3, M$^+$ −84).

REFERENCE EXAMPLE 25

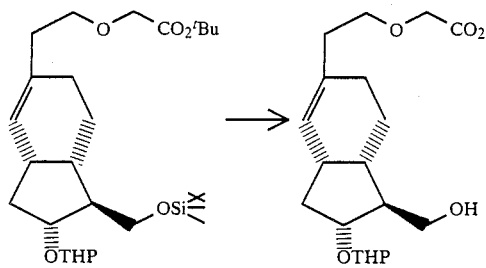

In the same manner as in Reference Example 14, 3-(3-oxa-4-t-butoxycarbonylbutyl)-7-exo-hydroxymethyl-8-endo-tetrahydropyranyloxy-cis-bicyclo[4,3,0-]nona-2-ene (202 mg, 74.9%) was prepared.

IR νmax (neat): 3500, 2950, 1750, 1440, 1370, 1300, 1230, 1200, 1130, 1080, 1020, 975, 910, 865, 845, 810 cm$^{-1}$.

NMR (CDCl$_3$) δ: 1.10–2.60 (16H, m), 1.50 (9H, s), 2.31 (2H, t, J=6 Hz), 3.35–4.20 (5H, m), 3.61 (2H, t, J=6 Hz), 3.96 (2H, s), 4.55–4.83 (1H, m), 5.45 (1H, br-s).

MASS (m/z) (%): 85 (100), 104 (31), 105 (30), 176 (44), 252 (16), 2.70 (25), 326 (2, M$^+$−84).

REFERENCE EXAMPLE 26

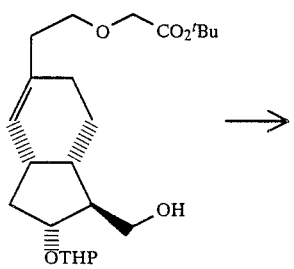

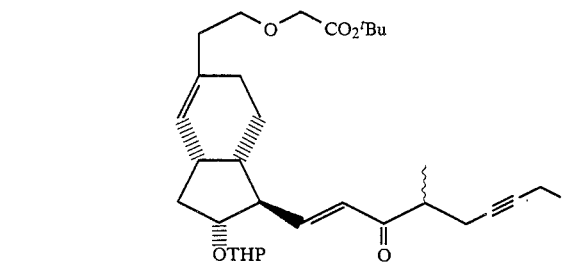

In the same manner as in Reference Example 15, 3-(3-oxa-4-t-butoxycarbonylbutyl)-7-exo-4,8-dimethyl-1-trans-octen-6-ynyl)-8-endo-tetrahydropyranyloxy-cis-bicyclo[4,3,0]nona-2-ene (63.1 mg, 71.9%) was prepared by the reaction with (2-oxo-3,7-dimethyl-5-heptyl)phosphonate.

IR νmax (neat): 2950, 1750, 1700, 1670, 1615, 1450, 1370, 1230, 1135, 1080, 1030, 980, 915, 870, 850, 820 cm$^{-1}$.

NMR (CDCl$_3$) δ: 1.00–2.70 (25H, m), 1.50 (9H, s). 2.30 (2H, t, J=6 Hz), 3.30–4.25 (4H, m), 3.61 (2H, t, J=6 Hz), 3.96 (2H, s), 4.50–4.75 (1H, m), 5.43 (1H, br-s), 6.30 (1H, d, d, J=15 Hz, 3 Hz), 6.70–7.10 (1H, m).

MASS (m/z) (%): 85 (100), 190 (94), 344 (32), 370 (35), 388 (37), 444 (2, M$^+$−84).

SYNTHESIS EXAMPLE 19

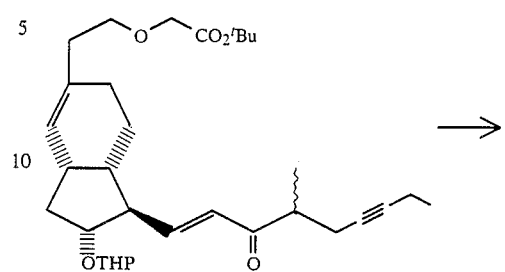

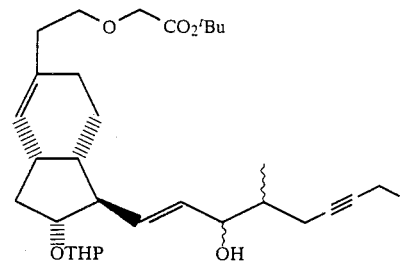

In the same manner as in Synthesis Example 1, 3-(3-oxa-4-t-butyoxycarbonylbutyl)-7-exo-(3-hydroxy-4,8-dimethyl-1-trans-octen-6-ynyl)-8-endo-tetrahydropyranyloxy-cis-bicyclo[4,3,0]nona-end (56 mg, 91.8%) was prepared.

IR νmax (neat): 3500, 2950, 1750, 1450, 1370, 1230, 1130, 1080, 1030, 975, 915, 870, 850, 810 cm$^{-1}$.

NMR (CDCl$_3$) δ: 0.80–2.70 (29H, m), 1.48, 1.53 (each 4.5H, s), 3.30–4.30 (4H, m), 3.60 (2H, t, J=6 Hz), 3.96 (2H, s), 4.69 (1H, br-s), 5.40 (1H, br-s), 5.40 (1H, br-s), 5.50–5.75 (2H, m).

MASS (m/z) (%): 85 (100), 100 (26), 174 (11), 252 (9), 328 (5), 354 (1), 372 (4, M$^+$−158).

SYNTHESIS EXAMPLE 20

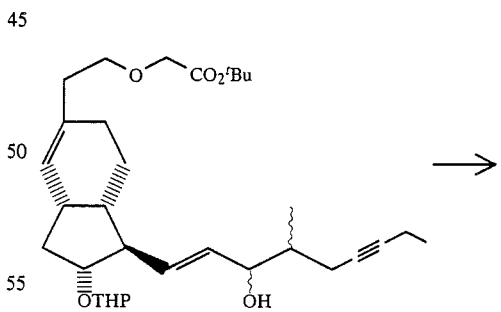

+

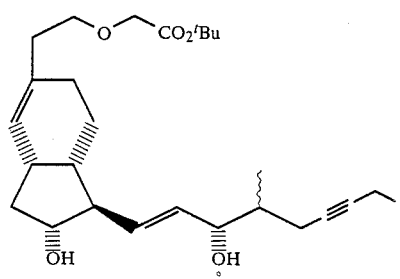

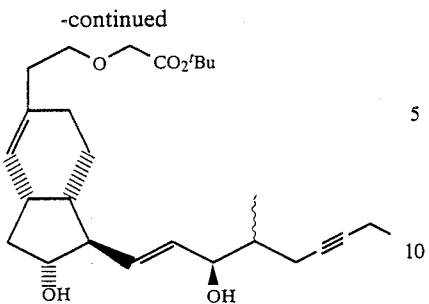

In the same manner as in Synthesis Example 3, 3-(3-oxa-4-t-butyoxycarbonylbutyl)-7-exo-(3α-hydroxy-4,8-dimethyl-1-trans-octen-6-ynyl)-8-endo-hydroxy-cis-bicyclo[4,3,0]nona-2-ene (23.7 mg, 51.4%) and its β-epimer (13,2 mg, 28.6%) were prepared.

The spectrum data of the β-epimer are as shown below. The spectrum data of the β-epimer are substantially the same.

IR νmax (neat): 3400, 2900, 1750, 1440, 1370, 1225, 1130, 1080, 1020, 970, 845 cm$^{-1}$.

NMR (CDCl$_3$) δ: 0.70–2.70 (22H, m), 1.46, 1.53 (each 4.5H, s), 2.23 (2H, t, J=6 Hz), 3.63 (2H, t, J=6 Hz), 3.80–4.30 (2H, m), 3.92 (2H, m), 5.45 (1H, br-s), 5.50–5.70 (2H, m).

MASS (m/z) (%): 57 (100), 107 (76), 174 (23), 201 (16), 252 (10), 328 (12), 355 (1), 373 (4, M$^+$−73).

SYNTHESIS EXAMPLE 21

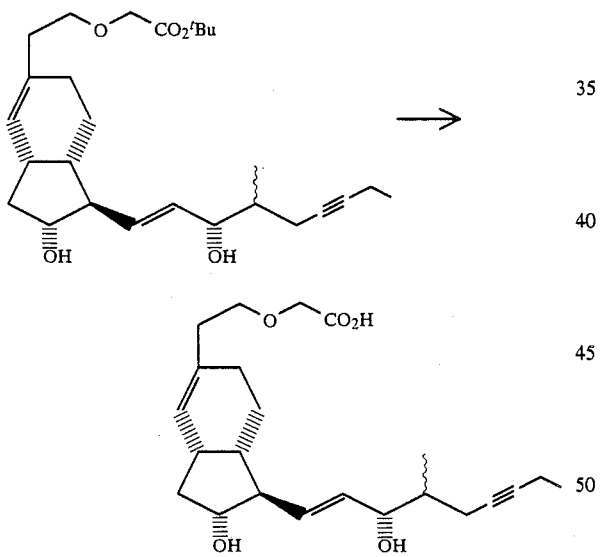

Under an argon atmosphere, a 7% potassium hydroxide-methanol solution was added to 27 mg (0.06 mmol) of 3-(3-oxa-4-t-butyoxycarbonylbutyl)-7-exo-(3α-hydroxy-4,8-dimethyl-1-trans-octen-6-ynyl)-8-endo-hydroxy-cis-bicyclo[4,3,0]nona-2-ene, and the mixture was stirred at room temperature for 20 hours. Then, after adjusting the mixture to pH8 with 1N hydrochloric acid, methanol was distilled off. The aqueous solution was washed with 1 ml of pentane, adjusted to pH4 with 1N hydrochloric acid, and then extracted with ethyl acetate. The extract was washed with a saturated sodium chloride aqueous solution, and dried over anhydrous magnesium sulfate. Then, the solvent was distilled off to obtain 15.08 mg (76.6%) of 3-(3-oxa-4-carboxybutyl)-7-exo-(3α-hydroxy-4,8-dimethyl-1-trans-octen-6-ynyl)-8-endo-hydroxy-cis-bicyclo[4,3,0]-nona-2-ene as light yellow substance.

IR νmax (neat): 3400, 2950, 1730, 1430, 1220, 1130, 1080, 1010, 970 cm$^{-1}$.

NMR (CDCl$_3$) δ: 0.80–1.40 (6H, m), 1.40–2.80 (18H, m), 3.35–4.30 (4H, m), 4.10 (2H, s), 5.40–5.70 (3H, m).

MASS (m/z) (%): 41 (100), 55 (67), 67 (65), 79 (64), 91 (70), 107 (69), 145 (30), 174 (17), 201 (14), 328 (10), 372 (2, M$^+$−18).

The spectrum data of the 15β-isomer are substantially the same as the above data.

REFERENCE EXAMPLE 27

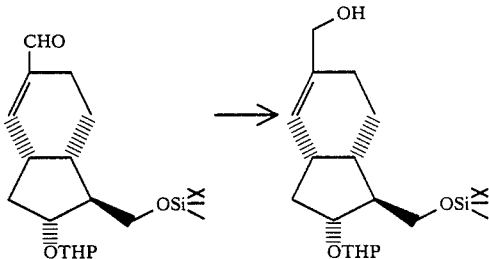

Under an argon atmosphere, 3-formyl-7-exo-t-butyl-dimethylsilyloxymethyl-8-endo-tetrahydropyranyloxy-cis-bicyclo[4,3,0]nona-2-ene (500 mg, 1.267 mmol) was dissolved in toluene (3 ml). Then, 1.27 ml (1.27 mmol) of a 1M toluene solution of diisobutylaminum hydride was dropwise added thereto at −78° C., and the mixture was stirred at the same temperature for 30 minutes. Then, methanol was added thereto, and the temperature was gradurally raised to room temperature. After an addition of 2 ml of an aqueous sodium chloride solution and 2 ml of ethyl acetate, the mixture was vigorously stirred. Then, the ethyl acetate layer was separated, washed with a saturated sodium chloride aqueous solution, and then dried over anhydrous magnesium sulfate. Then, the solvent was distilled off to obtain 495 mg (98.5%) of 3-hydroxymethyl-7-exo-t-butyldimethyl-silyloxymethyl-8-endo-tetrahydropyranyloxy-cis-bicyclo[4,3,0]nona-2-ene as a light yellow oily substance.

IRνmax (neat): 3480, 2950, 2880, 1470, 1390, 1360, 1260, 1200, 1100, 1080, 1030, 920, 840, 780, 750, 700 cm$^{-1}$.

NMR(CDCl$_3$) δ: 0.05 (6H, s), 0.90 (9H, s), 1.05–2.60 (16H, m), 3.30–4.30 (7H, m), 4.65 (1H, br-s), 5.66 (1H, br-s).

MASS (m/z) (%): 85 (100), 145 (42), 159 (80), 237 (10), 312 (2, M$^+$−84).

REFERENCE EXAMPLE 28

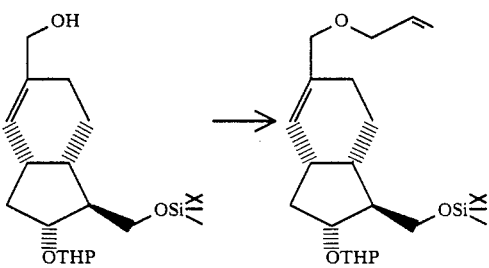

Under an argon atmosphere, 3-hydroxymethyl-7-exo-t-butyldimethylsilyloxymethyl-8-endo-tetrahydropyranyloxy-cis-bicyclo[4,3,0]nona-2-ene (483 mg, 1.243 mmol) was dissolved in methylene chloride (4 ml). Then, 3.7 ml (42.3 mmol) of allyl bromide, 2.8 g of a 50% sodium hydroxide aqueous solution and 42 mg of tetrabutylammonium hydrogensulfate were added thereto at room temperature, and the mixture was stirred for 7 days. Then, the mixture was extracted with ethyl ether, and the extract was washed with water and a saturated sodium chloride aqueous solution, and dried over anhydrous magnesium sulfate. Then, the solvent was distilled off to obtain a light yellow oily substance.

The purification was conducted by silica gel column chromatography to obtain 290 mg (53.4%) of 3-allyloxymethyl-7-exo-t-butyldimethylsilyloxymethyl-8-endo-tetrahydropyranyloxy-cis-bicyclo[4,3,0]nona-2-ene as a colorless oily substance.

IR$\nu$max (neat): 2950, 2870, 1470, 1390, 1360, 1260, 1200, 1120, 1080, 1035, 920, 840, 780 cm$^{-1}$.

NMR (CDCl$_3$) $\delta$: 0.04 (6H, s), 0.90 (9H, s), 1.35–2.60 (15H, m), 3.30–4.35 (9H, m), 4.65 (1H, m), 5.10–5.45 (2H, br-s), 5.66 (1H, br-s), 5.70–6.20 (1H, m).

MASS (m/z) (%): 41 (100), 75 (100), 85 (100), 145 (100), 159 (100), 162 (41), 210 (41), 237 (73), 351 (13, M$^+$−85), 436 (2, M$^+$).

REFERENCE EXAMPLE 29

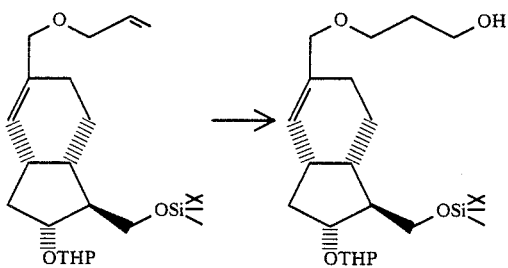

Under an argon atmosphere, 3-allyloxymethyl-7-exo-t-butyldimethylsilyloxymethyl-8-endo-tetrahydropyranyloxy-cis-bicyclo[4,3,0]nona-2-ene (286 mg, 0.655 mmol) was dissolved in THF (2 ml). Then, a THF solution (7 ml) of 9-BBN (190 mg, 0.786 mmol) was dropwise added thereto at −10° C., and the mixture was stirred at room temperature for one hour and 30 minutes. Further, the mixture was cooled with ice, and 0.54 ml of a 6N sodium hydroxide aqueous solution and 0.4 ml of a 30% hydrogen peroxide aqueous solution were added, and the mixture was stirred at room temperature for 2 hours. Then, the mixture was extracted with ethyl ether, and the extract was washed with a saturated sodium thiosulfate aqueous solution and a saturated sodium chloride aqueous solution, and then dried over anhydrous magnesium sulfate. Then, the solvent was dissolved off to obtain a colorless oily substance.

The purification was conducted by silica gel column chromatography to obtain 273 mg (91.3%) of 3-(2-oxa-5-hydroxypentyl)-7-exo-t-butyldimethylsilyloxymethyl-8-endo-tetrahydropyranyloxy-cis-bicyclo[4,3,0]nona-2-ene as a colorless oily substance.

IR$\nu$max (neat): 3480, 2950, 2860, 1465, 1440, 1380, 1360, 1250, 1200, 1100, 1080, 1030, 980, 910, 840, 780 cm$^{-1}$.

NMR (CDCl$_3$) $\delta$: 0.05 (6H, s), 0.90 (9H, s), 1.35–2.60 (18H, m), 3.35–4.25 (11H, m), 4.66 (1H, br-s), 5.66 (1H, br-s).

MASS (m/z) (%): 85 (100), 91 (39), 145 (65), 159 (56), 210 (33), 237 (24), 370 (5, M$^+$−84).

REFERENCE EXAMPLE 30

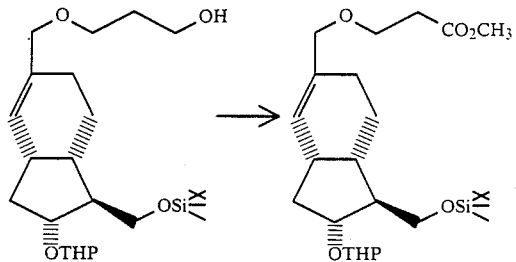

Under an argon atmosphere, 3-(2-oxa-5-hydroxypentyl)-7-exo-t-butyldimethylsilyloxymethyl-8-endo-tetrahydropyranyl-cis-bicyclo[4,3,0]nona-2-ene (271 mg, 0.596 mmol) was dissolved in dimethylsulfoxide (3 ml). Then, 0.833 ml (5.96 mmol) of triethylamine and 948 mg (5.96 mmol) of a sulfur trioxide-pyridine complex dissolved in 4 ml of dimethysulfoxide, were dropwise added thereto at room temperature, and the mixture was stirred at the same temperature for one hour. Then, after an addition of 30 ml of ice water, the mixture was extracted with ethyl acetate. The extract was washed with water and a saturated sodium chloride aqueous solution, and dried over anhydrous magnesium sulfate. Then, the solvent was distilled off to obtain a yellow oily substance. This yellow oily substance was dissolved in 2.8 ml of a mixture of methanol-THF (1:1). The solution was added to room temperature to a mixture comprising 272 mg (1.6 mmol) of silver nitrate, 0.74 ml of water and 0.61 ml of a 5N sodium hydroxide aqueous solution, and the mixture was stirred at the same temperature for 2 hours. After an addition of 10 ml of ethyl ether, the mixture was adjusted to pH4 with 10% hydrochloric acid, and extracted with ethyl ether. The extract was washed with a saturated sodium chloride aqueous solution, and dried over anhydrous magnesium sulfate. The solvent was distilled off to obtain a colorless oily substance. This colorless oily substance was treated with diazomethane to obtain 138 mg (48.0%) of 3-(2-oxa-4-methoxycarbonylbutyl)-7-exo-t-butyldimethylsilyloxymethyl-8-endo-tetrahydropyranyloxy-cis-bicyclo[4,3,0]nona-2-ene as a light yellow oily substance.

IR$\nu$max (neat): 2950, 2880, 1750, 1470, 1440, 1360, 1260, 1200, 1180, 1110, 1080, 1030, 915, 840, 780 cm$^{-1}$.

NMR (CDCl$_3$) $\delta$: 0.05 (6H, s), 0.90 (9H, s), 1.15–2.70 (15H, m), 2.60 (2H, t, J=6 Hz), 3.30–4.25 (7H, m), 3.70 (3H, s), 3.89 (2H, s), 4.66 (1H, br-s), 5.66 (1H, br-s).

MASS (m/z) (%): 85 (100) 145 (100), 159 (100), 162 (29), 237 (55), 277 (12), 398 (8, M$^+$−84).

REFERENCE EXAMPLE 31

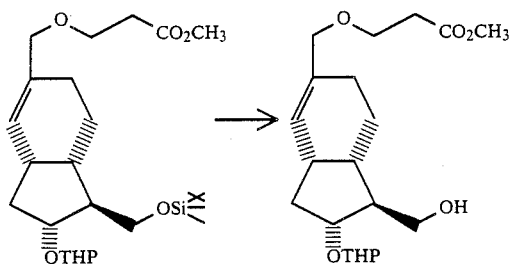

In the same manner as in Reference Example 14, 3-(2-oxa-4-methoxycarbonylbutyl)-7-exo-hydroxymethyl-8-endo-tetrahydropyranyloxy-cis-bicyclo[4,3,0]nona-2-ene (52 mg, 49.7%) was prepared.

IRνmax (neat): 3500, 2950, 2880, 1740, 1440, 1360, 1260, 1200, 1180, 1120, 1075, 1025, 975, 910, 870, 810, 750, 700 cm$^{-1}$.

NMR (CDCl$_3$) δ: 1.05–2.70 (16H, m), 2.60 (2H, t, J=6 Hz), 3.30–4.25 (7H, m), 3.72 (3H, s), 3.89 (2H, s), 4.50–4.80 (1H, m), 5.65 (1H, m).

MASS (m/z) (%): 85 (100), 91 (77), 105 (63), 145 (77), 162 (60), 180 (27), 195 (53), 266 (15), 284 (45), 368 (2, M$^+$).

REFERENCE EXAMPLE 32

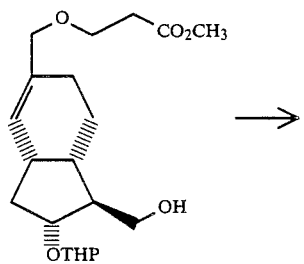

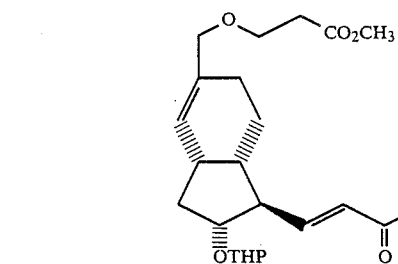

In the same manner as in Reference Example 15, 3-(2-oxa-4-methoxycarbonylbutyl)-7-exo-(3-oxo-4,8-dimethyl-1-trans-octen-6-ynyl)-8-endo-tetrahydropyranyloxy-cis-bicyclo[4,3,0]nona-2-ene (41.5 mg, 62.7%) was prepared by the reaction with (2-oxo-3,7-dimethyl-5-heptynyl)phosphonate.

IRνmax (neat): 2950, 1740, 1700, 1670, 1620, 1440, 1360, 1320, 1200, 1180, 1130, 1080, 1030, 975, 915, 870, 815, 750, 700 cm$^{-1}$.

NMR(CDCl$_3$) δ: 0.80–3.20 (28H, m), 3.20–4.40 (5H, m), 3.73 (3H, s), 3.90 (2H, s), 4.40–4.75 (1H, m), 5.63 (1H, br-s), 6.30 (1H, d, d, J=15 Hz, 3 Hz), 6.70–7.10 (1H, m).

MASS (m/z) (%): 85 (100), 91 (27), 105 (16), 210 (15), 231 (6), 298 (7), 402 (3, M$^+$ −84).

SYNTHESIS EXAMPLE 22

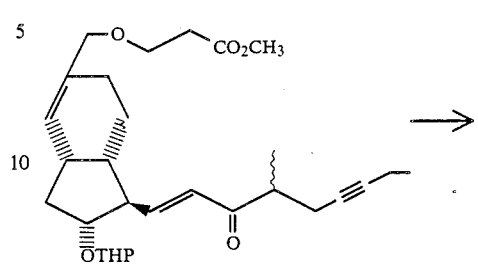

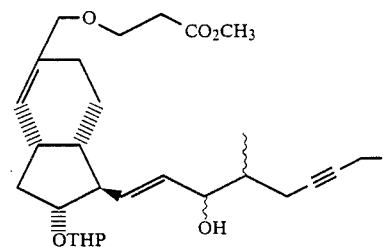

In the same manner as in Synthesis Example 1, 3-(2-oxa-4-methoxycarbonylbutyl)-7-exo-(3-hydroxy-4,8-dimethyl-1-trans-octen-6-ynyl)-8-endo-tetrahydropyranyloxy-cis-bicyclo[4,3,0]nona-2-ene (33.8 mg, 82.1%) was prepared.

IRνmax (neat): 3500, 2940, 1740, 1440, 1355, 1325, 1260, 1200, 1180, 1125, 1075, 1030, 975, 915, 870, 810 cm$^{-1}$.

NMR (CDCl$_3$) δ: 0.85–2.70 (27H, m), 2.60 (2H, t, J=6 Hz), 3.35–4.30 (6H, m), 3.72 (3H, s), 3.86 (2H, s), 4.69 (1H, br-s), 5.50–5.75 (3H, m).

MASS (m/z) (%): 85 (100), 107 (74), 145 (31), 174 (39), 215 (19), 342 (38), 372 (4), 386 (4, M$^+$ −102).

SYNTHESIS EXAMPLE 23

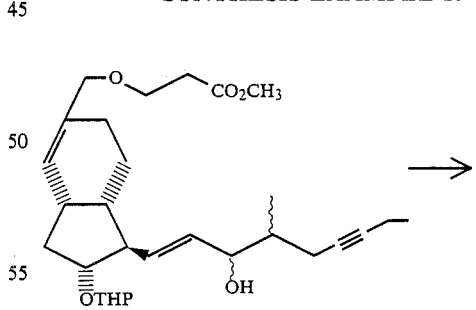

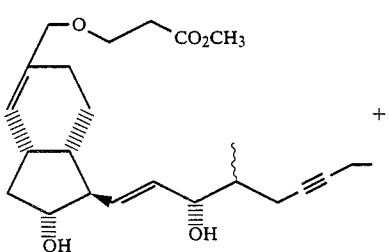

+

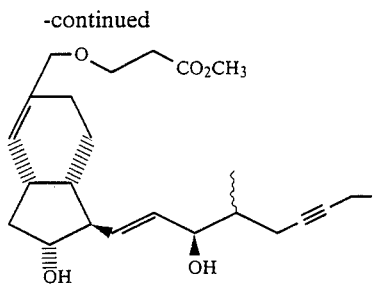

In the same manner as in Synthesis Example 3, 3-(2-oxo-4-methoxycarbonylbutyl)-7-exo-3α-hydroxy-4,8-dimethyl-1-trans-octen-6-ynyl)-8-endo-hydroxy-cis-bicyclo[4,3,0]nona-2-ene (7.1 mg, 25.4%) and its β-epimer (1 mg, 3.6%) were prepared.

The spectrum data of the α-isomer are as shown below. The spectrum data of the β-isomer are substantially the same.

IRνmax (neat): 3450, 2940, 1740, 1435, 1360, 1320, 1260, 1200, 1180, 1100, 1070, 1015, 970, 850 cm$^{-1}$.

NMR (CDCl$_3$) δ: 0.80–2.40 (22H, m), 2.60 (2H, t, J=6 Hz), 3.35–4.30 (4H, m), 3.73 (3H, s), 3.89 (2H, s), 5.50–5.75 (3H, m).

MASS (m/z) (%): 91 (100), 105 (87), 107 (82), 117 (39), 131 (51), 145 (50), 159 (29), 187 (29), 195 (26), 215 (11), 342 (16), 386 (2, M$^+$−18).

SYNTHESIS EXAMPLE 24

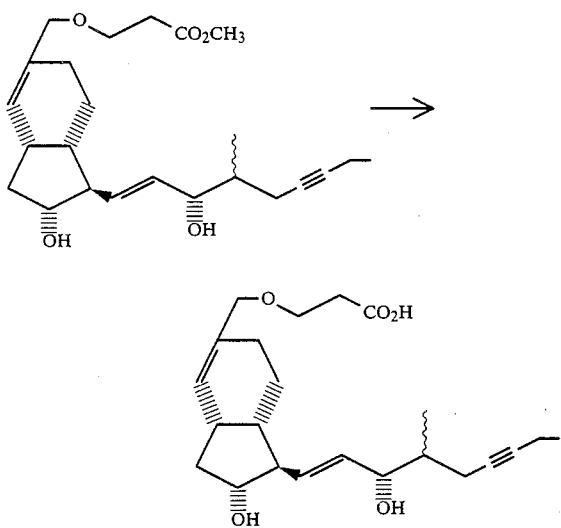

In the same manner as in Synthesis Example 5, 3-(2-oxa-4-carboxybutyl)-7-exo-(3α-hydroxy-4,8-dimethyl-1-trans-octen-6-ynyl)-8-endo-hydroxy-cis-bicyclo[4,3,0]nona-2-ene (7.1 mg, 100%) was prepared.

IRνmax (neat): 3450, 2950, 1730, 1440, 1380, 1355, 1320, 1270, 1190, 1100, 1070, 970, 840 cm$^{-1}$.

NMR (CDCl$_3$) δ: 0.80–1.40 (6H, m), 1.40–2.80 (18H, m), 3.60–4.40 (2H, m), 3.70 (2H, t, J=6 Hz), 3.91 (2H, s), 5.56–5.75 (3H, m).

MASS (m/z) (%): 41 (100), 55 (78), 67 (74), 79 (78), 91 (94), 107 (76), 131 (42), 145 (42), 187 (35), 205 (25), 328 (10), 372 (3, M$^+$−18).

REFERENCE EXAMPLE 13

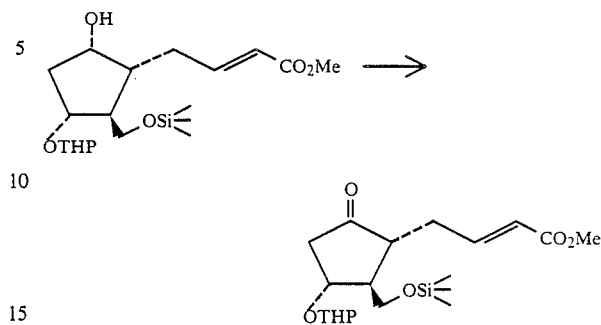

In the same manner as in Reference Example 4, 2=-(3-methoxycarbonyl-2-propenyl)-3β-t-butyldimethylsilyl-oxymethyl-4α-tetrahydropyranyloxy-1-cyclopentanone (2.78 g, 91%) was prepared from 2α-(3-ethoxycarbonyl)-2-propenyl)-3β-t-butyldimethylsilyloxymethyl-4α-tetrahydropyranyloxy-1α-cyclopentanol (3.08 g, 7.2 mmol).

IR(neat): 2950, 2850, 1750, 1730, 1660, 1470, 1430, 1260, 1200, 840 cm$^{-1}$

NMR (CDCl$_3$) δ: 6.92 (m, 1H), 5.90 (d, J=16.5 Hz, 1H), 4.70 (bs, 1H), 3.73 (s, 3H), 0.90 (s, 9H), 0.05 (s, 6H)

Mass m/z (%): b 267 (38), 159 (28), 133 (19), 105 (16), 89 (59), 85 (100), 75 (40), 73 (46), 56 (20), 41 (28)

REFERENCE EXAMPLE 34

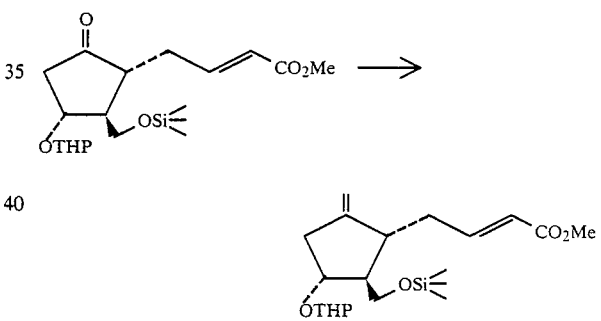

In the same manner as in Reference Example 5, 2α-(3-methoxycarbonyl-2-propenyl)-3β-t-butyldimethyl-silyloxymethyl-4α-tetrahydropyranyloxy-1-cyclopentylidene (1.23 g, 78%) was prepared from 2α-(3-methoxycarbonyl-2-propenyl)-3β-t-butyldimethyl-silyloxymethyl-4α-tetrahydropyranyloxy-1-cyclopentanone (1.6 g, 3.7 mmol).

IR(neat): 2950, 2860, 1730, 1660, 1480, 1440, 1260, 1200, 840 cm$^{-1}$

NMR(CDCl$_3$) δ: 6.93(m, 1H), 5.86(d, J=16.5 Hz, 1 H), 4.90(d, J=9 Hz, 2H), 4.60(bs, 1H), 3.70(s, 3H), 0.90(s, 9H), 0.05(s, 6H)

Mass m/z (%): 340 (M$^+$−84, trace), 265 (20), 191(17), 159(100), 131(66), 89(60), 85(100), 75(94), 73(86), 43(36)

REFERENCE EXAMPLE 35

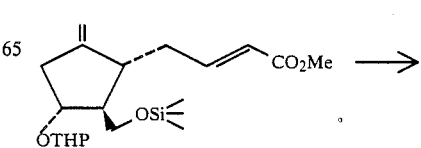

-continued

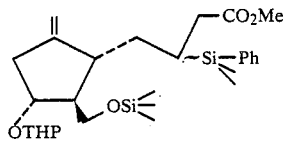

Under an argon atmosphere, cuprous cyanide (504 g, 5.66 mmol) was suspended in THF (5 ml), and a THF solution of phenyldimethylsilyllithium (1.83M, 6.1 ml, 11.32 mmol) was dropwise added thereto at 0° C. The mixture was stirred at 0° C. for 25 minutes. Then, a THF solution (5 ml) of 2α(3-methoxycarbonyl-2-propenyl)-3β-t-butyldimethylsilyloxymethyl-4α-tetrahydropyranyloxy-1-cyclopentylidene (1.2 g, 2.83 mmol) was dropwise added thereto at 0° C., and the mixture was further stirred at 0° C. for 30 minutes. After an addition of a saturated ammonium chloride aqueous solution, the reaction solution was diluted with ethyl ether. The mixture was stirred at room temperature until the aqueous layer became blue, and then extracted with ethyl ether. The organic layer was washed with a saturated sodium chloride aqueous solution, and dried over anhydrous magnesium sulfate. The solvent was distilled off, and the residue was purified by silica gel column chromatography (ethyl ether:n-hexane=1:8) to obtain 2α-(3-methoxy-carbonyl-2-phenyldimethylsilylpropyl)-3β-t-butyldimethyl-silyloxymethyl-4α-tetrahydropyranyloxy-1-cyclopentylidene (1.56 g, 99%).

IR(neat): 3000, 2950, 2860, 1740, 1660, 1470, 1430, 1250, 1200, 840 cm$^{-1}$

NMR(CDCl$_3$)δ: 7.46(m, 5H), 4.86(d, J=9 Hz, 2H), 4.60(bs, 1H), 3.56(s, 3H), 0.90(s, 9H), 0.30(s, 6H), 0.05(s, 6H)

Mass m/z (%): 560(M$^+$, trace), 235(51), 167(46), 159(64), 135(100), 89(73), 85(100), 75(61), 43(41)

REFERENCE EXAMPLE 36

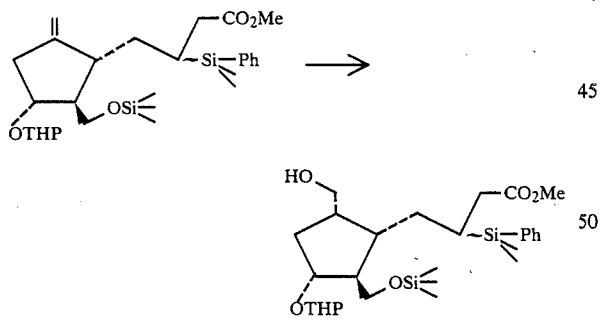

In the same manner as in Reference Example 6, 1-hydroxymethyl-2α-(3-methoxycarbonyl-2-phenyldimethylsilylpropyl)-3β-t-butyldimethylsilyloxymethyl-4α-tetrahydropyranyloxycyclopentanone (2.2 g, 92%) was prepared from 2α-(3-methoxycarbonyl-2-phenyldimethylsilylpropyl)-3β-t-butyldimethylsilyloxymethyl-4α-tetrahydropyranyloxy-1-cyclopentylidene (2.32 g, 4.14 mmol).

IR(neat): 3500, 3100, 2970, 2860, 1740, 1480, 1440, 1260, 1200, 850 cm$^{-1}$

NMR(CDCl$_3$)δ: 7.50(m, 5H), 4.75(bs, 1H), 3.68, 3.62(each s, 3H), 0.90 (s, 9H), 0.30(s, 6H)

Mass m/z (%): 493(M$^+$ −85, 24), 235(20), 159(77), 135(100), 89(53), 85(100), 75(76), 73(60), 43(31), 41(33)

REFERENCE EXAMPLE 37

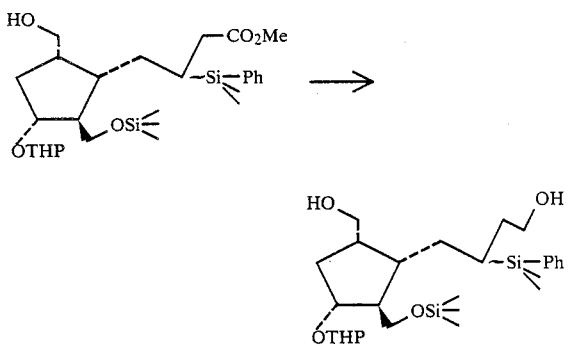

In the same manner as in Reference Example 7, 1α-hydroxymethyl-2α-(4-hydroxy-2-phenyldimethylsilylbutyl)-3β-t-butyldimethylsilyloxymethyl-4α-tetrahydropyranyloxycyclopentanone (2.06 g, 98%) was prepared from 1α-hydroxymethyl-2α-(3β-methoxycarbonyl-2-phenyldimethylsilylpropyl)-3β-t-butyldimethylsilyloxymethyl-4α-tetrahydropyranyloxycyclopentane (2.2 g, 3.8 mmol).

IR(neat): 3400, 3050, 2950, 2870, 1480, 1430, 1260, 1200, 840 cm$^{-1}$

NMR(CDCl$_3$)δ: 7.46(m, 5H), 4.70(bs, 1H), 0.90(s, 9H), 0.30(s, 6H), 0.05(t, 6H)

Mass m/z (%): 239(8), 159(37), 147(57), 135(100), 89(33), 85(100), 75(92), 73(58), 43(37), 41(34)

REFERENCE EXAMPLE 38

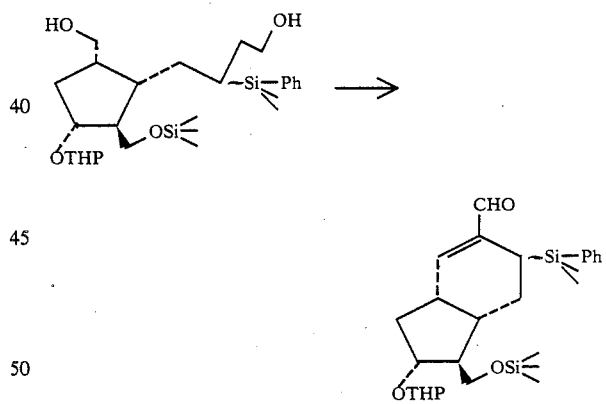

In the same manner as in Reference Example 8, 3-formyl-4-phenyldimethylsilyl-7-exo-t-butyldimethylsilyloxymethyl-8-endo-tetrahydropyranyloxy-cis-bicyclo[4,3,0]nona-2-ene (370 mg, 70%) was prepared from 1α-hydroxymethyl-2α-(4-hydroxy-2-phenyldimethylsilylbutyl)-3β-t-butyldimethylsilyloxymethyl)-4α-tetrahydropyranyloxycyclopentane (550 mg, 1 mmol).

IR(neat): 3100, 2980, 2880, 1690, 1620, 1470, 1260, 1200, 840 cm$^{-1}$

NMR(CDCl$_3$)δ: 9.36(s, 7/10H), 9.30 (s, 3/10H), 7.40(m, 5H), 6.72(bs, 3/10H), 6.60(bs, 7/10H), 4.60(bs, 1H), 0.90, 0.82(each s, total 9H), 0.30(m, 6H), 0.05(m, 6H)

Mass m/z (%): 444(M$^+$ −84, 6), 135(78), 85(100), 75(36), 73(42), 43(21)

REFERENCE EXAMPLE 39

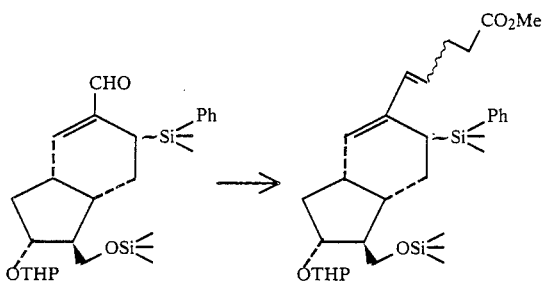

In the same manner as in Reference Example 17, 3-(4-methoxycarbonyl-1-butenyl)-4-phenyldimethylsilyl-7-exo-t-butyldimethylsilyloxymethyl-8-endo-tetrahydropyranyloxy-cis-bicyclo[4,3,0]nona-2-ene (1.46 g, 73%) was prepared from 3-formyl-4-phenyldimethylsilyl-7-exo-t-butyldimethylsilyloxymethyl-8-endo-tetrahydropyranyloxy-cis-bicyclo[4,3,0]nona-2-ene (1.73 g, 3.27 mmol).

IR(neat): 3050, 2910, 2830, 1740, 1460, 1430, 1240, 1200, 820 cm$^{-1}$

NMR(CDCl$_3$)δ: 7.43(m, 5H), 6.00(d, J=15 Hz, $\frac{1}{3}$H), 5.64(d, J=12 Hz, $\frac{2}{3}$H), 5.52(bs, 1H), 5.25(m, 1H), 4.63(bs, 1H), 3.70(s, 3H), 0.90(s, 9H), 0.30(s, 6H), 0.05(s, 6H), Mass m/z (%): 612(M$^+$, trace), 159(35), 135(100), 89(39), 85(100), 73(58), 43(38), 41(25)

REFERENCE EXAMPLE 40

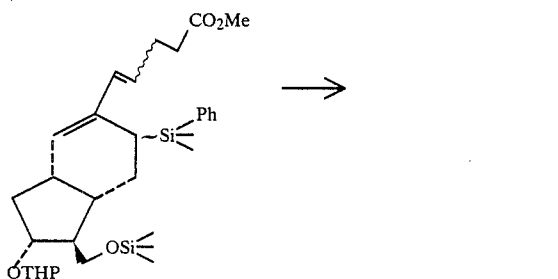

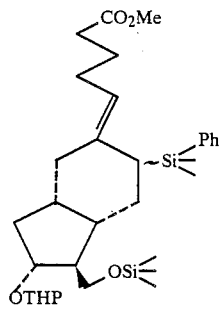

Under an argon atmosphere, 3-(4-methoxycarbonyl-1-butenyl)-4-phenyldimethylsilyl-7-exo-t-butyldimethylsilyloxymethyl-8-tetrahydropyranyloxy-cis-bicyclo[4,3,0]nona-2-ene (100 mg, 0.16 mmol) and a naphthalene-tricarbonyl chromium complex (13 mg, 0.048 mmol) were dissolved in THF (10 ml). Then, freezing by liquid nitrogen-vacuuming by a pump-melting was repeated 5 times for dearation. The mixture was transferred to a glass container in an autoclave, and filled with hydrogen under 100 kg/cm$^2$. The mixture was stirred at 50° C. for 12 hours. After cooling, the reaction solution was taken out, and the solvent was distilled off.

The residue thus obtained was purified by silica gel column chromatography (ethyl ether:n-hexane=1:6) to obtain 3-(4-methoxycarbonyl-(E)-butylidene)-4-phenyldimethylsilyl-7-exo-t-butyldimethylsilyloxymethyl-8-endo-tetrahydropyranyloxy-cis-bicyclo[4,3,0]nonane (97 mg, 97%).

IR(neat): 3100, 2960, 2880, 1740, 1470, 1430, 1260, 1200, 1030, 840 cm$^{-1}$

NMR(CDCl$_3$)δ: 7.40(m, 5H), 4.96(t, 1H), 4.60(bs, 1H), 3.66(s, 3H), 0.90(s, 9H), 0.30(s, 6H), 0.05(s, 6H)

Mass m/z (%): 614(M$^+$, trace), 159(43), 135(100), 85(100), 73(53), 43(43), 41(29)

REFERENCE EXAMPLE 41

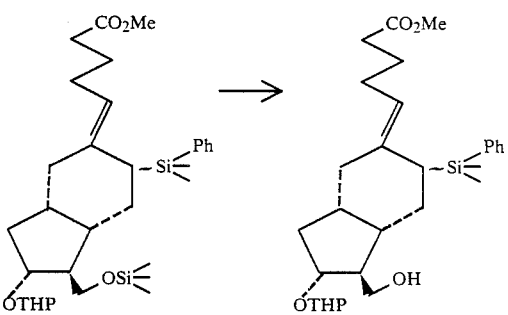

In the same manner as in Reference Example 14, 3-(4-methoxycarbonyl-(E)-butylidene)4-phenyldimethylsilyl-7-exo-hydroxymethyl-8-endo-tetrahydropyranyloxy-cis-bicyclo[4,3,0]nonane (40 mg, 80%) was prepared from 3-(4-methoxycarbonyl-(E)-butylidene)-4-phenyldimethylsilyl-7-exo-t-butyldimethylsilyloxymethyl-8-endo-tetrahydropyranyloxy-cis-bicyclo[4,3,0]nonane (61 mg, 0.1 mmol).

IR(neat): 3450, 3050, 2950, 2850, 1740, 1440, 1240, 1200, 830 cm$^{-1}$

NMR(CDCl$_3$)δ: 7.42(m, 5H), 5.02(t, 1H), 4.66(bs, 1H), 3.70(s, 3H), 0.30(s, 6H),

Mass m/z (%): 500(M$^+$, trace), 416(M$^+$ −84, 5) 415(M$^+$ −85, 4), 159(11), 135(100), 85(100), 57(25), 43(31), 41(30)

REFERENCE EXAMPLE 42

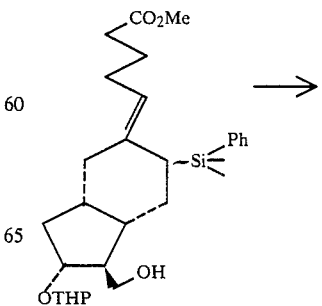

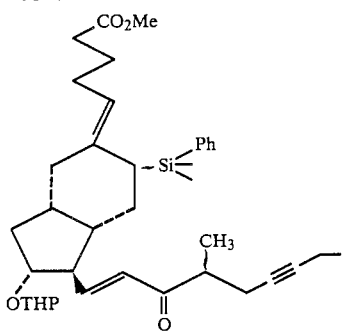

-continued

In the same manner as in Reference Example 15, 3-(4-methoxycarbonyl-(E)-butylidene)-4-phenyldimethylsilyl-7-exo-(3-oxo-4,8-dimethyl-1-trans-octen-6-ynyl)-8-endo-tetrahydropyranyloxy-cis-bicyclo[4,3,0-]nonane (32 mg, 86%) was prepared from 3-(4-methoxycarbonyl-(E)-butylidene)-4-phenyldimethylsilyl-7-exo-hydroxymethyl-8-endo-tetrahydropyranyloxy-cis-bicyclo[4,3,0]nonane (30 mg, 0.06 mmol) by the reaction with dimethyl(2-oxo-3,7-dimethyl-5-heptynyl)phosphonate.

IR(neat): 3050, 2950, 2890, 1740, 1690, 1670, 1620, 1450, 1440, 1250, 1200, 1030 830 cm$^{-1}$ NMR(CDCl$_3$)δ: 7.42(m, 5H), 6.80(m, 1H), 6.20(d*d, J=16.5, 4.5 Hz, 1H), 5.06(t, 1H), 4.60(m, 1H), 3.70(s, 3H), 1.13(m, 6H), 0.30(s, 6H)

Mass m/z (%): 534(M$^+$−84, 5), 533(M$^+$−85, 5), 516(15), 135(100), 91(20), 85(100), 67(25), 57(19), 43(24), 41(24)

REFERENCE EXAMPLE 43

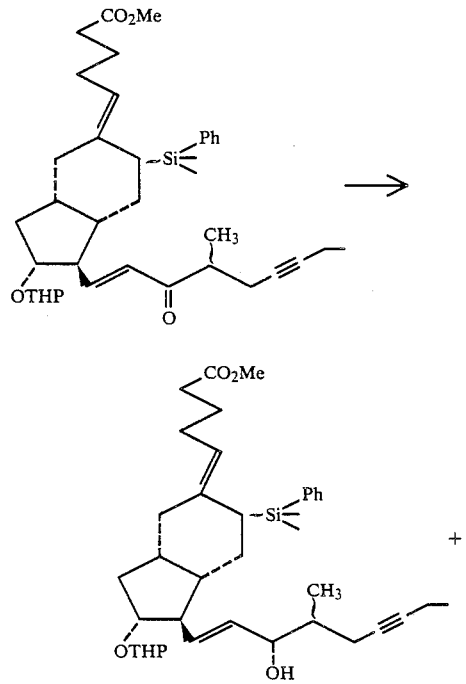

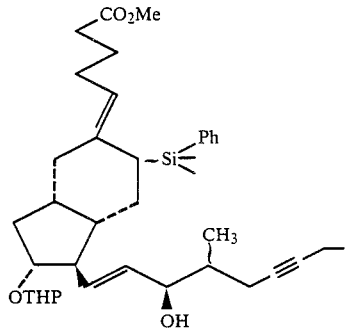

-continued

In the same manner as in Synthesis Example 1, 3-(4-methoxycarbonyl-(E)-butylidene)-4-phenyldimethylsilyl-7-exo-(3α-hydroxy-4,8-dimethyl-1-trans-octen-6-ynyl)-8-endo-tetrahydropyranyloxy-cis-bicyclo[4,3,0-]nonane (15.4 mg, 48%) and its β-epimer (14.7 mg, 46%) were prepared from 3-(4-methoxycarbonyl-(E)-butylidene)-4-phenyldimethylsilyl-7-exo-(3-oxo-4,8-dimethyl-1-trans-octen-6-ynyl)-8-endo-tetrahydropyranyloxy-cis-bicyclo[4,3,0]nonane (32 mg, 0.052 mmol). The spectrum data of the α-epimer are as shown below. The spectrum data of the β-epimer were substantially the same.

IR(neat): 3470, 3020, 2950, 2880, 1740, 1450, 1430, 1240, 1200, 1020, 830, 810 cm$^{-1}$ NMR(CDCl$_3$)δ: 7.42(m, 5H), 5.53(m, 2H), 5.06(t, 1H), 4.66(bs, 1H), 3.70(s, 3H), 1.10(m, 6H), 0.3(s, 6H), Mass m/z (%): 517(M$^+$−85-H$_2$O, 8), 254(10), 221(24), 135(100), 91(25), 85(100), 67(40), 57(35), 43(37), 41(35)

SYNTHESIS EXAMPLE 25

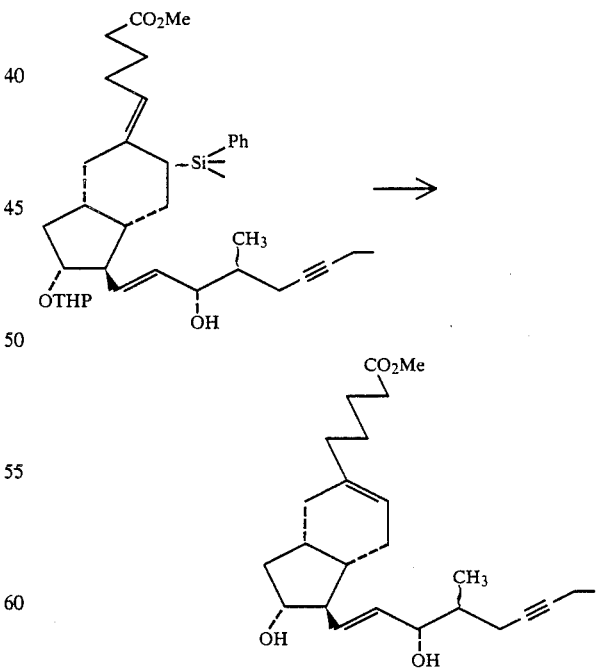

3-(4-methoxycarbonyl-(E)-butylidene)-4-phenyldimethylsilyl-7-exo-(3α-hydroxy-4,8-dimethyl-1-trans-octen-6-ynyl)-8-endo-tetrahydropyranyloxy-cis-bicyclo[4,3,0]-nonane (22 mg, 0.035 mmol) was dissolved in a mixture of acetonitrile:water (1 ml) (volume ratio of 98:2). Then, p-toluenesulfonic acid monohydrate (7 mg, 0.035 mmol) was added thereto, and the mixture was stirred at room temperature for one day and night. The mixture was neutralized at 0° C. with a saturated sodium bicarbonate aqueous solution, and acetonitrile was distilled off under reduced pressure. The residual aqueous layer was extracted with ethyl acetate, and the extract was washed with a saturated sodium chloride aqueous solution, and dried over anhydrous magnesium sulfate. Then, the solvent was distilled off, and the residue thus obtained was purified by silica gel column chromatography (ethyl ether:n-hexane=5:1) to obtain 3-(4-methoxycarbonylbutyl)-7-exo-(3α-hydroxy-4,8-dimethyl-1-trans-octen-6-ynyl)-8-endo-hydroxybicyclo[4,3,0-]nona-3-ene (9.9 mg, 70%) as a high polarity fraction.

A low polarity fraction (6.7 mg) was dissolved in a mixture of acetic acid:THF:water (0.3 ml) (volume ratio of 3:1:1), and the solution was stirred at 60° C. for 3 hours. After cooling, the mixture was diluted with ethyl acetate, and neutralized with a saturated sodium bicarbonate aqueous solution. The ethyl acetate layer was washed with a saturated sodium chloride aqueous solution, and dried over anhydrous magnesium sulfate. Then, the solvent was distilled off, and the residue thus obtained was purified by silica gel column chromatography (ethyl ether:n-hexane=5:1) to obtain 3-(4-methoxycarbonylbutyl)-7-exo-(3α-hydroxy-4,8-dimethyl-1-trans-octen-6-ynyl)-8-endo-hydroxy-cis-bicyclo[4,3,0]nona-3-ene (2.3 mg).

The spectrum data of the 15β-epimer are substantially the same.

IR(neat): 3400, 2930, 2850, 1740, 1450, 1430, 1010, 810 cm$^{-1}$

NMR (CDCl$_3$) δ: 5.56 (m, 1H), 4.10 (m, 2H), 3.70 (s, 3H), 1.13 (t, 3H), 0.98 (q, 3H)

Mass m/z (%): 384(M$^+$-H$_2$O, 7), 317(21), 161(88), 145(49), 131(57), 91(95), 81(100), 79(71), 55(87), 43(41), 41(85)

SYNTHESIS EXAMPLE 26

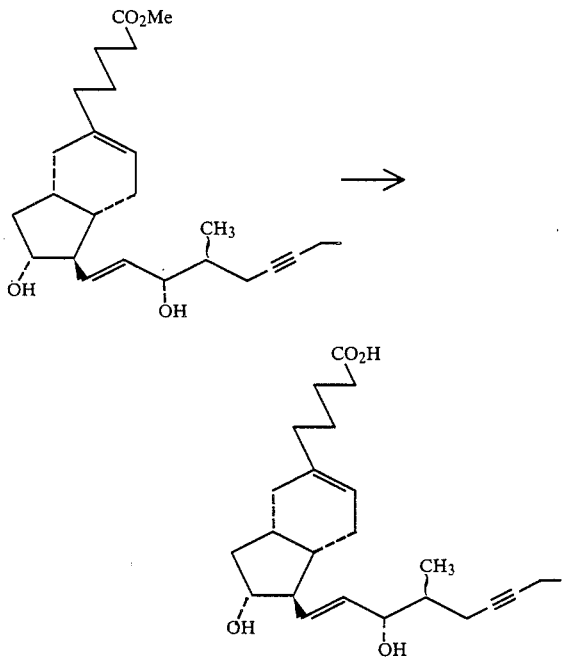

In the same manner as in Synthesis Example 5, 3-(4-carboxybutyl)-7-exo-(3α-hydroxy-4,8-dimethyl-1-trans-octen-6-ynyl)-8-endo-hydroxy-cis-bicyclo[4,3,0-]nona-3-ene (Compound a) (18.3 mg, 94%) was prepared from 3-(4-methoxycarbonylbutyl)-7-exo-(3α-hydroxy-4,8-dimethyl-1-trans-octen-6-ynyl)-8-endo-hydroxy-cis-bicyclo[4,3,0]nona-3-ene (20.1 mg, 0.05 mmol). In the same manner, the 15β-epimer was obtained by the hydrolysis to obtain 3-(4-carboxybutyl)-7-exo-(3β-hydroxy-4,8-dimethyl-1-trans-octen-6-ynyl)-8-endo-hydroxy-cis-bicyclo[4,3,0]nona-3-ene. The spectrum data of the 15β-epimer are as shown below. The spectrum data of the 15β-epimer are substantially the same.

IR(neat): 3400, 2930, 1710, 1450, 1100, 970 cm$^{-1}$

NMR (CDCl$_3$)δ: 5.53 (m, 3H), 4.52 (bs, 3H), 4.00 (m, 2H), 1.20 (t, 3H), 1.06 (q, 3H)

Mass m/z (%): 370(M$^+$-H$_2$O, 5), 229(10), 161(57), 145(40), 107(68), 91(94), 81(97), 79(72), 55(99), 41(100)

Now, Test Examples 1 to 8 will be given by using the following compounds as test compounds:

(a) 3-(3-carboxypropyl)-7-exo-(3α-hydroxy-trans-1-octenyl)-8-endo-hydroxy-cis-bicyclo[4,3,0]nona-2-ene (b) 3-(3-carboxypropyl)-7-exo-(3α-hydroxy-4,8-dimethyl-trans-1-octen-6-ynyl)-8-endo-hydroxy-cis-bicyclo[4,3,0]nona-2-ene (c) 3-(4-carboxy-1-butenyl)-7-exo-(3α-hydroxy-trans-1-octenyl)-8-endo-hydroxy-cis-bicyclo[4,3,0]nona-2-ene (d) 3-(4-carboxy-1-butenyl)-7-exo-(3α-hydroxy-4,8-dimethyl-trans-1-octen-6-ynyl)-8-endo-hydroxy-cis-bicyclo[4,3,0]nona-2-ene (e) 3-(4-carboxybutyl)-7-exo-(3α-hydroxy-trans-1-octenyl)-8-enodo-hydroxy-cis-bicyclo[4,3,0]nona-2-ene (f) 3-(4-carboxybutyl)-7-exo-(3α-hydroxy-4,8-dimethyl-trans-1-octen-6-ynyl)-8-endo-hydroxy-cis-bicyclo[4,3,0]nona-2-ene (g) 3(3-oxa-4-carboxybutyl)-7-exo-(3α-hydroxy-4,8-dimethyl-1-trans-octen-6-ynyl)-8-endo-hydroxy-cis-bicyclo[4,3,0]nona-2-ene (h) 3(2-oxa-4-carboxybutyl)-7-exo-(3α-hydroxy-4,8-dimethyl-1-trans-octen-6-ynyl-8-endo-hydroxy-cis-bicyclo[4,3,0]nona-2-ene (i) 3-(4-carboxybutyl)-7-exo-(3α-hydroxy-4,8-dimethyl-1-trans-octen-6-ynyl-8-endo-hydroxy-cis-bicyclo[4,3,0]nona-3-ene

TEST EXAMPLE 1

Blood platelet aggutination inhibiting activity

Japanese white male rabbits having a weight of from 2.0 to 2.5 kg were used.

Under anesthesia with sodium Pentobarbital, blood was sampled from the carotid artery, and mixed with a 1/7 volume of an anticoagulant citric acid dextrose solution. Then, the mixture was subjected to centrifugal separation at 140×g for 15 minutes, whereupon the supernatant (platelet rich plasma:PRP) was obtained. PRP was subjected to centrifugal separation at 1,300×g for 7 minutes. The blood platelet pellets thus obtained were washed with a HEPES buffer solution (pH 6.5) for washing blood platelets, and subjected to centrifugal separation at 1,300×g for 7 minutes. The blood platelet pellets washed twice under such condition, were suspended in a suspending liquid (a buffer solution for washing blood platelets, which contains 0.1% of human fibrinogen, 1.8 mM of CaCl$_2$ and 1.2 mM of MgCl$_2$) to obtain a blood platelet suspension having a concentration of from $5\times 10^8$ to $8\times 10^8$ platelets/ml.

The platelet agglutination ability was measured by means of an agglutination meter. To 380 μl of the platelet suspension, 10 μl of a test compound or a solvent as the control, was added. Three minutes later, 10 μl of a platelet agglutinating substance (10 μM of ADP or 1 μg/ml of collagen, as the final concentration) was added thereto to induce agglutination.

The blood platelet agglutination inhibiting activity of each test compound was represented by $ED_{50}$ (i.e. the concentration of the test compound where the platelet agglutination is suppressed to 50%). The results are shown in column (A) in Table 1.

TEST EXAMPLE 2

Blood flow-increasing activity in the coronary artery

A crossbred adult dog having a weight of from 9 to 15 kg was anesthetized with sodium Pentobarbital and subjected to thoractomy under artificial respiration. After pericardiectomy, the frontal descending branch of the left coronary artery was separated from the surrounding tissues, and a blood flow-measuring probe was attached thereto under sodium heparin treatment. The coronary blood flow was measured by using an electromagnetic flow meter. The test compound was injected into the coronary artery by near arterial injection, and the blood flow-increasing activity in the coronay artery was represented by $ED_{50}$ (i.e. the dose of a test compound at which the blood flow increases by 50%, as evaluated on the basis that the blood flow increase by the reactive hyperemia caused by releasing the blood flow of the coronary artery after blocking it for 15 seconds, is evaluated to be 100%). The results are shown in the column (B) in Table 1.

TEST EXAMPLE 3

Blood flow-increasing activity in the vertebral artery

A made or female crossbred adult dog having a weight of from 8 to 13 kg was anesthetized by intravenous administration of sodium Pentobarbital and subjected to thoractomy along the mediam line under artificial respiration to expose the left vertebral artery. Under sodium peparin treatment, a polyethylene cannula was inserted into the vertebral artery, and a blood flow-measuring probe was attached to its other end, to which a blood circulation tube led from the left femoral artery was connected, whereby the blood flow in the vertebral artery was measured by using an electromagnetic flow meter. The test compound was injected into the vertebral artery by near arterial injection, and the blood flow-increasing activity in the vertebral artery was represented by $ED_{50}$ (i.e. the dose of a test compound at which the blood flow increases by 50%, as evaluated on the basis that the blood flow increase (representing substantially the maximum reaction) by the administration of 100 μg/kg papaverine hydrochloride into the vertebral artery, is evaluated to be 100%). The results are shown in the column (C) in Table 1.

TEST EXAMPLE 4

Blood flow-increasing activity in the femoral artery

A male or female crossbred adult dog having a weight of from 8 to 13 kg, was anesthetized by intravenous administration of sodium Pentobarbital. Then, a tracheal cannula was inserted, and artificial respiration was conducted. The blood flow in the femoral artery was measured by inserting the annula into the left femoral artery under sodium heparin treatment and providing a blood flow measuring probe at it other end, and by using an electromagnetic flow meter. The test compound was injected into the femoral artery by near arterial injection, and the blood flow-increasing activity in the femoral artery was represented by $ED_{50}$ (i.e. the dose of a test compound at which the blood flow increases by 50%, as evaluated on the bais that the blood flow increase (representing substantially the maximum reaction) by the administration of 100 μg/kg of papaveline hydrochloride into the femoral artery, is evaluted to be 100%). The results are shown in the column (D) in Table 1.

TEST EXAMPLE 5

Hypotensive activity

A male or female crossbred adult dog having a weight of from 9 to 14 kg was anesthetized by intraveous administration of sodium Pentobarbital. Then, the left carotid was exposed under artificial respiration, and the blood pressure was measured by using an electric blood pressure meter. The test compound was administered from the left femoral vein, and the hypotensive activity was represented by $ED_{50}$ (i.e. the dose at which the diastolic blood pressure is reduced by 50 mmHg). The results are shown in the column (E) in Table 1.

TEST EXAMPLE 6

Ethanol ulcer inhibiting activity

Male wister rats having a weight of from 170 to 270 g were put into individual cages and starved for 24 hours. During this starvation period, the rats were allowed to drink water freely. A test compound or $PGE_2$ as a comparative compound was orally administered in an amount of 3, 10 or 30 μg/kg, and 30 minutes later, 1 ml of 99.5% ethanol was orally administered to each rat. One hour after the ethanol administration, each rat was filled by cervical vertebral luxation, and the stomach was taken out. A 1% formaline solution was injected into the stomach in an amount of about 8 ml, and the stomach was fixed in the formaline solution for 30 minutes. After the fixing, the stomach was severed along the greater curvature, and the mucous membrane surface of the stomach was gently washed with flowing water. Then, the total length of damages appearing on the gastric glandular portion was obtained and used as the ulcer index.

The ethanol ulcer inhibiting activity of a test compound was represented by $ED_{50}$ (i.e. the dose of the test compound at which the ulcer was inhibited by 50% relative to the ulcer index of the non-treated group). The results are shown in column (A) in Table 2. To the non-treated group, the solvent was administered.

TEST EXAMLE 7

Hydrochloric acid ulcer inhibiting activity

Male wister rabits having a weight of from 190 to 240 g were used. The rats were starved in the same manner as in Test Example 6, and the test compounds and $PGE_2$ were, respectively, orally administered in an amount of 30 μg/kg, and 30 minutes later, 1 ml of 0.6N hydrochloric acid was orally administered. Thirty minutes after the hydrochloric acid administration, each rat was killed by cervical vertebral luxation. Then, the stomach was taken out and fixed, and the ulcer index was obtained, in the same manner as in Test Example 6. The hydrochloric acid ulcer inhibiting activity of a test compound was represented by the inhibiting percentage (i.e. the percentage of the ulcer index of the treated group to the ulcer index of the non-treated group). The results are shown in the column (B) in Table 2. To the non-treated group, the solvent was administered.

TEST EXAMPLE 8

Indomethacine ulcer inhibiting activity

Male wister rats having a weight of from 210 to 270 g were used. The rats were starved in the same manner as in Test Example 6. Then, 60 μg/kg of a test compound or 30 μg/kg of $PGE_2$ was orally administered to each rat, and 30 minutes later, 60 mg/kg of indomethacine was hypodermically administered. Three hours after the indomethacine administration, the test compound or PGE2 was again orally administered in the same amount. Six hours after the first administration of indomethacine, each rat was killed by cervical bertebral luxation. The stomach was taken out and fixed, and the ulcer index was obtained, in the same manner as in Test Example 6.

The indomethacine ulcer inhibiting activity of a test compound was represented by the inhibiting percentage (i.e. the inhibiting percentage of the ulcer index of the treated group to the ulcer index of the non-treated group). The results are shown in the column (C) in Table 2. To the non-treated group, the solvent was administered.

Now, Formulation Examples for the formulation of compounds used in the preceding Test Examples, will be given.

Formulation Example 1

Compound: 500 mg
Patato starch: 150 mg
Silicic anhydride: 50 mg
Magnesium stearate: 10 mg
Lactose: Balance to the total of 1,000 mg The above ingredients were uniformly mixed and filled into hard capsules in an amount of 200 mg each.

Formulation Example 2

Compound: 500 mg
Potato starch: 100 mg
Crystalline cellulose: 60 mg
Silicic anhydride: 50 mg
Hydroxypropyl cellulose: 30 mg
Magnesium stearate: 15 mg
Lactose: Balance to the total of 1,000 mg The active ingredients, lactose, potato starch, crystalline cellulose and silicic anhydride were mixed. After an addition of a methanol solution containing 10% of hydroxypropyl cellulose was added thereto, and the mixture was kneaded and granulated. Then, it was extruded through a screen having openings with a diameter of 0.8 mm, to obtain granules. After drying the granules, the magnesium stearate was added thereto, followed by compression molding to obtain tablets each having a weight of 200 mg.

Formulation Example 3

Compound: 500 mg
Propylene glycol: Balance to the total of 10 ml

The active ingredient was dissolved in propylene glycol, and the solution was asceptically filtered and then filled into ampules in an amount of 0.2 ml each.

Formulation Example 4

Compound: 250 mg
Polyethylene glycol 1,500: 3,000 mg
Polyethylene glycol 6,000: Balance to the total of 5,000 mg The above ingredients were heat-melted at 60° C. and uniformly mixed, and the mixture was poured into a plastic mold and cooled to obtain a suppository of 1 g.

TABLE 1

| Compound (Compound No.) | (A) Platelet agglutination inhibiting activity $ED_{50}$ (M) (Activity ratio) | (B) Blood flow-increasing activity in coronary artery $ED_{50}\%$ (μg/kg) (Activity ratio) | (C) Blood flow-increasing activity in vertebral artery $ED_{50}\%$ (μg/kg) (Activity ratio) | (D) Blood flow-increasing activity in femoral artery $ED_{50}\%$ (μg/kg) (Activity ratio) | (E) Hypotensive activity $ED_{50}$ mmHg (μg/kg) (Activity ratio) |
|---|---|---|---|---|---|
| Prostacyclin 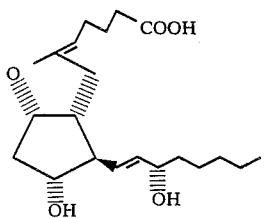 | ADP agglutination: $2.9 \times 10^{-9}$ (1) Collagen agglutination $3.4 \times 10^{-9}$ (1) | 0.010 (1) | 0.044 (1) | 0.024 (1) | 0.024 (1) |
| (a) | ADP agglutination: | 37.6% increase | 0.44 (1/10) | 0.19 (1/8) | 20 mmHg |

TABLE 1-continued

| Compound (Compound No.) | (A) Platelet agglutination inhibiting activity ED$_{50}$ (M) (Activity ratio) | (B) Blood flow-increasing activity in coronary artery ED$_{50}$% (μg/kg) (Activity ratio) | (C) Blood flow-increasing activity in vertebral artery ED$_{50}$% (μg/kg) (Activity ratio) | (D) Blood flow-increasing activity in femoral artery ED$_{50}$% (μg/kg) (Activity ratio) | (E) Hypotensive activity ED$_{50}$ mmHg (μg/kg) (Activity ratio) |
|---|---|---|---|---|---|
| (a) | $1.3 \times 10^{-6}$ (1/455) Collagen agglutination: $9.7 \times 10^{-7}$ (1/285) | at 3 μg/kg (About 1/500) | | | decrease at 10 μg/kg (About 1/192) |
| (b) | ADP agglutination: $7.7 \times 10^{-8}$ (1/27) Collagen agglutination: $4.4 \times 10^{-8}$ (1/12) | 1.20 (1/120) | 0.75 (1/17) | 0.35 (1/15) | 27.9 mmHg decrease at 10 μg/kg (About 1/125) |
| (c) | ADP agglutination: $5.0 \times 10^{-8}$ (1/17) Collagen agglutination: $7.3 \times 10^{-8}$ (1/21) | 2.10 (1/210) | 36.9% increase at 3 μg/kg (About 1/120) | 0.56 (1/23) | 27.9 mmHG decrease at 10 μg/kg (About 1/125) |
| (d) | ADP agglutination: $8.7 \times 10^{-9}$ (1/3) Collagen agglutination $4.9 \times 10^{-9}$ (1/1.4) | 0.38 (1/38) | 1.9 (1/43) | 0.90 (1/38) | 8.7 (1/36) |
| (e) | ADP agglutination: $2.9 \times 10^{-7}$ (1/100) Collagen agglutination: $2.8 \times 10^{-7}$ (1/82) | 3.80 (1/380) | 2.50 (1/57) | 0.46 (1/19) | 17.9 mmHg decrease at 10 μg/kg (About 1/213) |
| (f) | ADP agglutination: | 1.75 (1/269) | 0.57 (1/13) | 0.56 (1/23) | 33 mmHg |

TABLE 1-continued

| Compound (Compound No.) | (A) Platelet agglutination inhibiting activity ED$_{50}$ (M) (Activity ratio) | (B) Blood flow-increasing activity in coronary artery ED$_{50}$% ($\mu$g/kg) (Activity ratio) | (C) Blood flow-increasing activity in vertebral artery ED$_{50}$% ($\mu$g/kg) (Activity ratio) | (D) Blood flow-increasing activity in femoral artery ED$_{50}$% ($\mu$g/kg) (Activity ratio) | (E) Hypotensive activity ED$_{50}$ mmHg ($\mu$g/kg) (Activity ratio) |
|---|---|---|---|---|---|
| [structure] | $2.3 \times 10^{-8}$ (1/8) Collagen agglutination: $2.7 \times 10^{-8}$ (1/8) | | | | decrease at 10 $\mu$g/kg (About 1/77) |
| (g) [structure] | ADP agglutination: $3.8 \times 10^{-8}$ (1/13) Collagen agglutination $2.9 \times 10^{-8}$ (1/8.5) | 0.55 (1/55) | 2.0 (1/45) | 0.72 (1/30) | 16.0 (1/67) |
| (h) [structure] | ADP agglutination: $3.0 \times 10^{-6}$ < Collagen agglutination: $3.0 \times 10^{-6}$ < | 25% increase at 3 $\mu$g/kg | 28.5% increase at 3 $\mu$g/kg | 31.7% increase at 3 $\mu$g/kg | 15 mmHg decrease at 10 $\mu$g/kg |
| (i) [structure] | ADP agglutination: $2.2 \times 10^{-8}$ (1/7.6) Collagen agglutination: $2.4 \times 10^{-8}$ (1/7) | 3.6 (1/360) | 0.8 (1/18) | 0.56 (1/23) | 24.5 mmHg decrease at 10 $\mu$g/kg (About 1/152) |

TABLE 2

| Compound (Compound No.) | (A) Ethanol ulcer inhibiting activity ED50% (μg/kg, P.O.) (Activity ratio) | (B) Hydrochloric acid inhibiting activity Inhibiting rate (%) | (C) Indomethacine ulcer inhibiting activity Inhibiting rate (%) | (D) Hypotensive activity ED50 mmHg (μg/kg, i.v.) |
|---|---|---|---|---|
| PGE2 | 9.03 | 61.6 | 98.3% inhibition by oral administration 30 μg/kg twice | |
| Prostacyclin | No inhibiting activity observed by oral administration of 30 μg/kg | No inhibiting activity observed by oral administration of 30 μg/kg | No inhibiting activity observed by oral administration of 60 μg/kg twice. | |
| (a) | 20.0% inhibition by oral administration of 30 μg/kg | 15.3% inhibiting by oral administration of 30 μg/kg | Certain inhibition observed by oral administration of 60 μg/kg twice. | |

TABLE 2-continued

| Compound (Compound No.) | (A) Ethanol ulcer inhibiting activity ED50% (μg/kg, P.O.) (Activity ratio) | (B) Hydrochloric acid inhibiting activity Inhibiting rate (%) | (C) Indomethacine ulcer inhibiting activity Inhibiting rate (%) | (D) Hypotensive activity ED50 mmHg (μg/kg, i.v.) |
|---|---|---|---|---|
| (b) | 2.79 | 54.8 | 99.4% inhibition by oral administration of 60 μg/kg twice | |
| (c) | 31.7% inhibition by oral administration of 30 μg/kg | 13.5% inhibition by oral administration of 30 μg/kg | Certain inhibition observed by oral administration of 60 μg/kg twice. | |
| (d) | 2.55 | 24.1 | 73.5% inhibition by oral administration of 60 μg/kg twice | |

TABLE 2-continued

| Compound (Compound No.) | (A) Ethanol ulcer inhibiting activity ED$_{50}$% (μg/kg, P.O.) (Activity ratio) | (B) Hydrochloric acid inhibiting activity Inhibiting rate (%) | (C) Indomethacine ulcer inhibiting activity Inhibiting rate (%) | (D) Hypotensive activity ED$_{50}$ mmHg (μg/kg, i.v.) |
|---|---|---|---|---|
| (e) | 28.5% inhibition by oral administration of 30 μg/kg | 18.3% inhibition by oral administration of 30 μg/kg | Certain inhibition observed by oral administration of 60 μg/kg twice | |
| (f) | 2.92 | 20.5 | 38.8% inhibition by oral administration of tion of 60 μg/kg twice. | |
| (g) | 5.38 | 42.1 | 57.3% inhibition by oral administration of 60 μg/kg twice | 16.1 |

TABLE 2-continued

| Compound (Compound No.) | (A) Ethanol ulcer inhibiting activity ED$_{50}$% (μg/kg, P.O.) (Activity ratio) | (B) Hydrochloric acid inhibiting activity Inhibiting rate (%) | (C) Indomethacine ulcer inhibiting activity Inhibiting rate (%) | (D) Hypotensive activity ED$_{50}$ mmHg (μg/kg, i.v.) |
|---|---|---|---|---|
| (h) | 32.5% inhibition by oral administration of 30 μg/kg | 21.3% inhibition by oral administration of 30 μg/kg | Certain inhibition observed by oral administration of 60 μg/kg twice | 15 mmHg decrease at 10 μg/kg |
| (i) | 5.89 | 17.4 | 49.5% inhibition by oral administration of tion of 10 μg/kg twice. | 24.5 mmHg decrease at 60 μg/kg |

We claim:
1. A prostacyclin analogue having the formula:

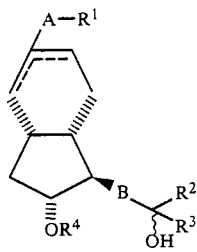
(I)

wherein $R^1$ is —$CO_2R^5$ (wherein $R^5$ is a hydrogen atom, a straight chain or branched alkyl group having from 1 to 12 carbon atoms, an aralkyl group having from 7 to 12 carbon atoms, a cycloalkyl group having from 4 to 7 carbon atoms and unsubstituted or substituted by at least one alkyl group having form 1 to 4 carbon atoms, a substituted or unsubstituted phenyl group, or one equivalent of a cation), or —$CONR^6R^7$ (wherein each of $R^6$ and $R^7$ is a hydrogen atom or a alkyl group having from 1 to 10 carbon atoms, or $R^6$ and $R^7$ together with the adjacent nitrogen atom, form a 5- or 6-membered substituted or unsubstituted hetero ring which may contain a hetero atom other than said nitrogen atom); A is —$CH_2CH_2CH_2$—, $CH_2$—O—$CH_2CH_2$—, —$CH_2CH_2CH_2CH_2$—, —$CH_2CH_2$—OH—$CH_2$— or —CH=$CHCH_2CH_2$—; B is trans —CH=CH— or —C≡C—; $R^2$ is a straight chain or branched alkyl group having from 3 to 10 carbon atoms, a cycloalkyl group having from 4 to 7 carbon atoms and unsubstituted or substituted by at least one alkyl group having from 1 to 4 carbon atoms, a straight chain or branched alkenyl group having form 3 to 12 carbon atoms, a straight chain or branched alkynyl group having from 3 to 8 carbon atoms, or an alkyl group having from 1 to 3 carbon atoms substituted by a substituted or unsubstituted phenyl or phenyoxy group, by an alkoxy group having from 1 to 6 carbon atoms or by a cycloalkyl group having from 5 to 8 carbon atoms; $R^3$ is a hydrogen atom, a methyl group or a vinyl group; and $R^4$ is a hydrogen atom, an acyl group having from 1 to 7 carbon atoms, a tri-$C_1$-$C_7$ hydrocarbon-silyl group or a group capable of forming an acetal bond together with the oxygen atom of a hydroxyl group; provided that the double bond in a substituent for A is E or Z, or a mixture thereof; the asymmetric center in a substituent for $R^2$ assumes a R-conformation or a S-conformation, or a mixture thereof; and the bonds shown by dotted lines at the 2–3 and 3–4 positions mean that either one of them is a double bond.

2. The prostacyclin analogue according to claim 1, wherein $R^1$ is carboxyl, methoxycarbonyl or ethoxycarbonyl, $R^2$ is n-pentyl, 2-methylpentyl, 1,1-dimethylpentyl, 1-methylhexyl, 2-methylhexyl, 2,6-dimethyl-5-heptenyl, 1-methyl-3-pentynyl, 1-methyl-3-hexynyl, 2-methyl-3-hexynyl, (2-ethoxy-1-methyl)ethyl, cyclopentyl, cyclohexyl, 2-cyclohexylethyl, 1-cyclohexylethyl or phenethyl, and $R^4$ is hydrogen, tert-butyl-dimethylsilyl, tert-butyl-diphenylsilyl, 2-tetrahydropyranyl, acetyl, 4-(4-methoxytetrahydropyranyl), 6,6-dimethyl-3-oxa-2-oxobicyclo[3,4,0]hex-4-yl or dimethyl(2,4,6-tri-tert-butylphenoxy)silyl.

3. A blood circulation improving agent comprising an effective amount of the prostacyclin analogue as defined in claim 1 and a pharmaceutically acceptable carrier.

4. An anti-ulcer composition comprising an effective amount of the prostacyclin analogue as defined in claim 1 and a pharmaceutically acceptable carrier.

* * * * *